United States Patent
Taniko et al.

(10) Patent No.: US 9,663,463 B2
(45) Date of Patent: May 30, 2017

(54) 3-AZABICYCLO[3.1.0]HEXANE DERIVATIVE AND USE THEREOF FOR MEDICAL PURPOSE

(71) Applicants: SANWA KAGAKU KENKYUSHO CO., LTD., Nagoya-shi, Aichi (JP); UBE INDUSTRIES, LTD., Ube-shi, Yamaguchi (JP)

(72) Inventors: Kaori Taniko, Inabe (JP); Toshiyuki Miyazawa, Inabe (JP); Tatsuroh Kaneko, Toride (JP); Daisuke Kurumazuka, Inabe (JP); Satoko Harada, Inabe (JP); Toru Izuchi, Inabe (JP); Morio Okabe, Kariya (JP); Ryo Iwamura, Ube (JP); Yasunori Tsuzaki, Ube (JP); Hiroyuki Setoguchi, Ube (JP); Yuuki Imura, Ube (JP); Hiroto Akaza, Ube (JP); Motohisa Shimizu, Ube (JP); Tomio Kimura, Tokyo (JP)

(73) Assignees: SANWA KAGAKU KENKYUSHO CO., LTD., Aichi (JP); UBE INDUSTRIES, LTD., Yamaguchi (JP)

(*) Notice: Subject to any disclaimer, the term of this patent is extended or adjusted under 35 U.S.C. 154(b) by 0 days.

(21) Appl. No.: 15/035,923

(22) PCT Filed: Nov. 19, 2014

(86) PCT No.: PCT/JP2014/080681
§ 371 (c)(1),
(2) Date: May 11, 2016

(87) PCT Pub. No.: WO2015/076310
PCT Pub. Date: May 28, 2015

(65) Prior Publication Data
US 2016/0280645 A1    Sep. 29, 2016

(30) Foreign Application Priority Data
Nov. 20, 2013    (JP) .................... 2013-239460

(51) Int. Cl.
*C07D 209/52*    (2006.01)
*C07D 401/06*    (2006.01)
*C07D 403/06*    (2006.01)

(52) U.S. Cl.
CPC ......... *C07D 209/52* (2013.01); *C07D 401/06* (2013.01); *C07D 403/06* (2013.01)

(58) Field of Classification Search
CPC ... C07D 209/52; C07D 401/06; C07D 405/06
See application file for complete search history.

(56) References Cited

U.S. PATENT DOCUMENTS 6,313,312 B1    11/2001    Banks et al.
7,049,335 B2    5/2006    McHardy et al.
(Continued)

FOREIGN PATENT DOCUMENTS

JP    2005511545 A    4/2005
JP    2006522797 A    10/2006
(Continued)

OTHER PUBLICATIONS

McHardy, Med Chem COmmun, vol. 2, 1001-1005, 2011.*
(Continued)

*Primary Examiner* — D M Seaman
(74) *Attorney, Agent, or Firm* — Oliff PLC

(57) ABSTRACT

The object of the present invention is to provide a compound having an antagonistic action against μ-opioid receptors, which causes less side effects and thus is highly safe.
A compound represented by the general formula (I), or a pharmacologically acceptable salt thereof:

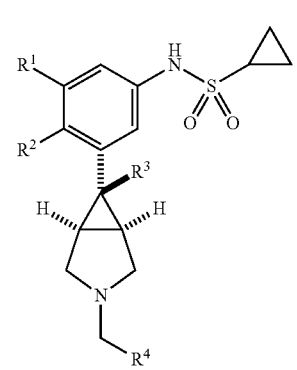

(I)

wherein
R¹ and R² are the same or different, and each represents a hydrogen atom or a halogen atom, provided that R¹ and R² are not simultaneously halogen atoms,
R³ represents a $C_1$-$C_3$ alkyl group or a vinyl group, and
R⁴ represents the formula (II):

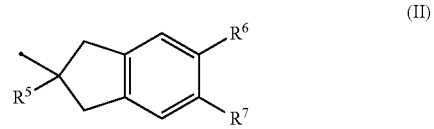

(II)

wherein R⁵ represents a hydroxy group or a $C_1$-$C_3$ alkoxy group, and R⁶ and R⁷ are the same or different, and each represents a hydrogen atom or a halogen atom;

(Continued)

or the formula (III):

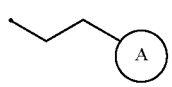

(III)

wherein Ring A represents a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group.

15 Claims, No Drawings

(56) References Cited

U.S. PATENT DOCUMENTS

| | | |
|---|---|---|
| 7,056,930 B2 | 6/2006 | Coe et al. |
| 2002/0025948 A1 | 2/2002 | Banks et al. |
| 2003/0087898 A1 | 5/2003 | McHardy et al. |
| 2005/0043327 A1 | 2/2005 | Coe et al. |
| 2005/0043345 A1 | 2/2005 | Coe et al. |
| 2005/0075387 A1 | 4/2005 | Tickner et al. |
| 2005/0113437 A1 | 5/2005 | McHardy et al. |

FOREIGN PATENT DOCUMENTS

| | | | |
|---|---|---|---|
| WO | 01/98267 | * | 12/2001 |
| WO | 01/98267 A1 | | 12/2001 |
| WO | 2005/014552 A1 | | 2/2005 |
| WO | 2008/075162 A2 | | 6/2008 |
| WO | 2008/142454 A1 | | 11/2008 |
| WO | 2009/027293 A1 | | 3/2009 |
| WO | 2013/074386 A2 | | 5/2013 |

OTHER PUBLICATIONS

Micheli et al., "1-(Aryl)-6-[alkoxyalkyl]-3-azabicyclo[3.1.0]hexanes and 6-(Aryl)-6-[alkoxyalkyl]-3-azabicyclo[3.1.0]hexanes: A New Series of Potent and Selective Triple Reuptake Inhibitors" Journal of Medicinal Chemistry, 2010, vol. 63, pp. 2534-2551.

Satoh et al., "1-Chloroalkyl p-Tolyl Sulfoxides as Useful Agents for Homologation of Carbonyl Compounds: Conversion of Carbonyl Compounds to α-Hydroxy Acids, Esters, and Amides and α,α'-Dihydroxy Ketones", Journal of Organic Chemistry, vol. 56, 1991, pp. 4129-4134.

Atemnkeng et al., "Protection for the Carboxyl Group", T.W. Greene & P.G.M Wuts, Protective Groups in Organic Synthesis, pp. 582 and 725.

Sheridan et al., "Diastereoisomers of 2-benzyl-2, 3-dihydro-2-(1H-inden-2-yl)-1H-inden-1-ol: Potential antinflammatory agents", Bioorganic and Medicinal Chemistry Letters, vol. 19, 2009, pp. 5927-5930.

Lunn, G. et al., "SAR and biological evaluation of 3-azabicyclo[3.1.0]hexane derivatives as μ opioid ligands", Bioorganic & Medicinal Chemistry Letters, 2012, vol. 22, pp. 2200-2203.

Feb. 17, 2015 International Search Report issued in International Application No. PCT/JP2014/080681.

Lunn, G. et al., "Discovery and synthesis of a new class of opioid ligand having a 3-azabicyclo[3.1.0]hexane core. An example of a 'magic methyl' giving a 35-fold improvement in binding", Bioorganic & Medicinal Chemistry Letters, 2011, pp. 4608-4611.

Gonzalez et al., "A Review of its Pharmacodynamic and Pharmacokinetic Properties and Therapeutic Efficacy in the Management of Opioid Dependence", ADIS Drug Information Services, 1988, pp. 192-213.

McHardy et al., "Discovery of CP-866,087, a mu opioid receptor antagonist for the treatment of alcohol abuse and dependence", Medicinal Chemistry Communications, vol. 2, 2011, pp. 1001-1005.

* cited by examiner

3-AZABICYCLO[3.1.0]HEXANE DERIVATIVE AND USE THEREOF FOR MEDICAL PURPOSE

TECHNICAL FIELD

The present invention relates to novel 3-azabicyclo[3.1.0] hexane derivatives that are useful as medicaments, and the medicinal uses thereof. The compounds have various medicinal uses as μ-opioid receptor antagonist drugs.

BACKGROUND ART

Opioid is a collective term for synthesis or endogenous peptides having alkaloid and morphine-like activities such as narcotic analgesics and related synthetic analgesics thereof. For the opioid receptors that are involved in the expression of the action of opioids, four kinds of subtypes of μ, κ, δ and ORL-1 are currently known. Among these, μ-opioid receptors are receptors that are the most relevant to the action of morphine, and besides morphine, fentanyl, and methionine enkephalin and β-endorphin, which are endogenous opioids, also act.

By administering morphine or fentanyl, which is a μ-opioid receptor agonist, itchiness occurs. Also in animal experiments, morphine induces scratching motions in spinal intrathecal administration in monkeys, administration from medullary dorsal horn in rats, and intracisternal administration in mice. Furthermore, since the itchiness in refractory pruritus diseases is ameliorated by μ-opioid receptor antagonist drugs, it is considered that the activation of μ opioid receptors by methionine enkephalin and β-endorphin, which are endogenous opioids, is involved in the occurrence of itchiness.

Since it has been confirmed in various clinical tests that μ-opioid receptor antagonist drugs such as naltrexone suppress itchiness in patients on dialysis and patients with cholestatic liver cirrhosis, the development of μ-opioid receptor antagonist drugs as anti-pruritus drugs is expected, but there has been no approved drug until now. In addition, side effects such as nausea, vomit, hyperalgesia such as stomach ache, and diarrhea are recognized in naltrexone, and thus naltrexone is not necessarily satisfiable as an anti-pruritus drug (Non Patent Literature 1). Therefore, creation of a μ-opioid receptor-selective medicament that causes less side effects and thus is highly safe is desired.

Until now, many 3-azabicyclo[3.1.0]hexane derivatives having a μ-opioid receptor-antagonistic activity have been reported (Patent Literatures 1 to 15, and Non Patent Literatures 2 to 4), but any of the compounds disclosed in these documents are different from the compounds of the present invention in structure.

CITATIONS LIST

Patent Literatures

Patent Literature 1: WO2000/039089
Patent Literature 2: U.S. Pat. No. 6,313,312
Patent Literature 3: WO2001/098267
Patent Literature 4: US2002/0025948
Patent Literature 5: WO2003/035622
Patent Literature 6: US2003/0087898
Patent Literature 7: WO2005/018645
Patent Literature 8: US2005/0043327
Patent Literature 9: WO2005/018670
Patent Literature 10: US2005/0043345
Patent Literature 11: WO2005/033080
Patent Literature 12: US2005/0075387
Patent Literature 13: WO2005/037790
Patent Literature 14: US2005/0113437
Patent Literature 15: WO2008/075162

Non-Patent Literatures

Non Patent Literature 1: Drugs, 35, 192-213 (1988)
Non Patent Literature 2: Bioorganic & Medicinal Chemistry Letters, 21 (2011) 4608-4611
Non Patent Literature 3: Medicinal Chemistry Communications, 2 (2011) 1001-1005
Non Patent Literature 4: Bioorganic & Medicinal Chemistry Letters, 22 (2012) 2200-2203

SUMMARY OF INVENTION

Technical Problems

The object of the present invention is to provide a compound having an antagonistic action against μ-opioid receptors, which causes lesser side effects and thus is highly safe, or a pharmacologically acceptable salt thereof, and to provide an agent for preventing or treating pruritus based on an antagonistic action against μ-opioid receptors.

Solutions to Problems

Based on the above-mentioned points, in order to solve the above-mentioned problems, many intensive studies were done with aiming at creating a μ-opioid receptor antagonist drug having a novel structure. Consequently, it was found that a compound having the following general formula (I) and a pharmacologically acceptable salt thereof have a very excellent μ-opioid receptor antagonistic action, and the present invention was completed.

That is, according to the present invention, compounds each having the following general formula (I) or pharmacologically acceptable salts thereof are provided, and these compounds and pharmacologically acceptable salts thereof will be referred to as "compound (s) of the present invention" herein. The present invention can be represented as exemplary embodiments of the following (1) to (15), and the like.

(1) A compound represented by the general formula (I), or a pharmacologically acceptable salt thereof:

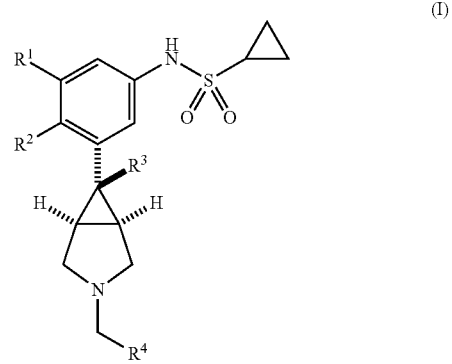

wherein
$R^1$ and $R^2$ are the same or different, and each represents a hydrogen atom or a halogen atom, provided that $R^1$ and $R^2$ are not simultaneously halogen atoms,
$R^3$ represents a $C_1$-$C_3$ alkyl group or a vinyl group, $R^4$ represents the formula (II):

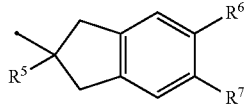

wherein $R^5$ represents a hydroxy group or a $C_1$-$C_3$ alkoxy group, and $R^6$ and $R^7$ are the same or different, and each represents a hydrogen atom or a halogen atom;

or the formula (III):

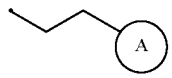

wherein Ring A represents a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group.

(2) The compound or a pharmacologically acceptable salt thereof according to (1), wherein $R^1$ is a hydrogen atom in the general formula (I).

(3) The compound or a pharmacologically acceptable salt thereof according to (1), wherein $R^3$ is a methyl group, an ethyl group or a vinyl group in the general formula (I).

(4) The compound or a pharmacologically acceptable salt thereof according to (1), wherein $R^4$ is the formula (II) in the general formula (I):

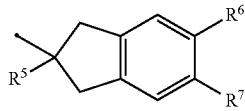

wherein $R^5$ represents a hydroxy group or a $C_1$-$C_3$ alkoxy group, and $R^6$ and $R^7$ are the same or different, and each represents a hydrogen atom or a halogen atom.

(5) The compound or a pharmacologically acceptable salt thereof according to (4), wherein $R^5$ is a hydroxy group or a methoxy group, and $R^6$ and $R^7$ are each a hydrogen atom in the formula (II).

(6) The compound or a pharmacologically acceptable salt thereof according to (5), wherein $R^1$ is a hydrogen atom, $R^2$ is a hydrogen atom or a fluorine atom, and $R^3$ is an ethyl group in the general formula (I).

(7) The compound or a pharmacologically acceptable salt thereof according to (1), wherein $R^4$ is the formula (III):

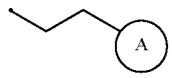

wherein Ring A is a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group.

(8) The compound or a pharmacologically acceptable salt thereof according to (7), wherein Ring A is a fluorine atom(s)-substituted cyclohexyl group which is optionally substituted by a $C_1$-$C_3$ alkoxy group, or a fluorine atom(s)-substituted 5- to 6-membered nitrogen-containing saturated heterocyclic group in the formula (III).

(9) The compound or a pharmacologically acceptable salt thereof according to (8), wherein Ring A is any group selected from the following group:

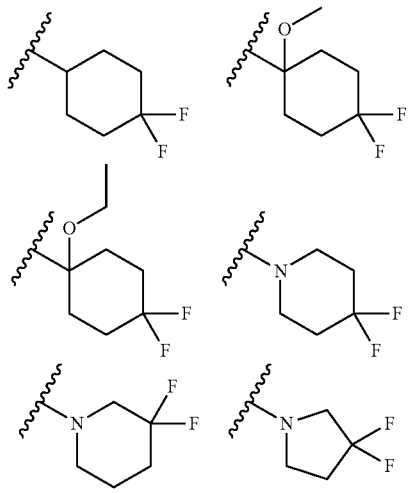

in the formula (III).

(10) The compound or a pharmacologically acceptable salt thereof according to (8), wherein $R^1$ is a hydrogen atom, $R^2$ is a hydrogen atom or a fluorine atom, and $R^3$ is an ethyl group in the general formula (I).

(11) The compound or a pharmacologically acceptable salt thereof according to (9), wherein $R^1$ is a hydrogen atom, $R^2$ is a hydrogen atom or a fluorine atom, and $R^3$ is an ethyl group in the general formula (I).

(12) The compound or a pharmacologically acceptable salt thereof according to (4), which is selected from the group consisting of:

N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)cyclopropanesulfonamide, N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide, N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide, N-(3-{(1R,5S,6r)-6-ethyl-3-[(2-hydroxy-2,3-dihydro-1H-inden-2-yl)methyl]-3-azabicyclo[3.1.0]hexan-6-yl}-5-fluorophenyl)cyclopropanesulfonamide, N-(3-{(1R,5S,6r)-6-ethyl-3-[(2-methoxy-2,3-dihydro-1H-inden-2-yl)methyl]-3-azabicyclo[3.1.0]hexan-6-yl}-4-fluorophenyl)cyclopropanesulfonamide, N-(3-{(1R,5S,6r)-6-ethyl-3-[(2-methoxy-2,3-dihydro-1H-inden-2-yl)methyl]-3-azabicyclo[3.1.0]hexan-6-yl}-5-fluorophenyl)cyclopropanesulfonamide, N-(3-{(1R,5S,6r)-3-[(2-ethoxy-2,3-dihydro-1H-inden-2-yl)methyl]-6-ethyl-3-azabicyclo[3.1.0]hexan-6-yl}phenyl)cyclopropanesulfonamide, N-(3-{(1R,5S,6r)-3-[(2-hydroxy-2,3-dihydro-1H-inden-2-yl)methyl]-6-methyl-3-azabicyclo[3.1.0]hexan-6-yl}phenyl)cyclopropanesulfonamide, N-(3-{(1R,5S,6r)-3-[(2-methoxy-2,3-dihydro-1H-inden-2-yl)methyl]-6-methyl-3-azabicyclo[3.1.0]hexan-6-yl}phenyl)cyclopropanesulfonamide, N-(3-{(1R,5S,6r)-3-[(2-hydroxy-2,3-dihydro-1H-inden-2-yl)methyl]-6-vinyl-3-azabicyclo[3.1.0]hexan-6-yl}phenyl)cyclopropanesulfonamide, and N-(3-{(1R,5S,6r)-3-[(5,6-difluoro-2-hydroxy-2,3-dihydro-1H-inden-2-yl)methyl]-6-ethyl-3-azabicyclo[3.1.0]hexan-6-yl}phenyl)cyclopropanesulfonamide.

(13) The compound or a pharmacologically acceptable salt thereof according to (7), which is selected from the group consisting of:

N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide, N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide, N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide, N-(3-{(1R,5S,6r)-3-[3-(4,4-difluoropiperidin-1-yl)propyl]-6-ethyl-3-azabicyclo[3.1.0]hexan-6-yl}phenyl)cyclopropanesulfonamide, N-(3-{(1R,5S,6r)-3-[3-(3,3-difluoropyrrolidin-1-yl)propyl]-6-ethyl-3-azabicyclo[3.1.0]hexan-6-yl}phenyl)cyclopropanesulfonamide, N-(3-{(1R,5S,6r)-3-[3-(3,3-difluoropyrrolidin-1-yl)propyl]-6-ethyl-3-azabicyclo[3.1.0]hexan-6-yl}-4-fluorophenyl)cyclopropanesulfonamide, N-(3-{(1R,5S,6r)-3-[1-ethoxy-(4,4-difluorocyclohexyl)propyl]-6-ethyl-3-azabicyclo[3.1.0]hexan-6-yl}phenyl)cyclopropanesulfonamide, N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide, and N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide.

(14) A medicament containing the compound or a pharmacologically acceptable salt thereof according to any one of (1) to (13) as an active ingredient.

(15) The medicament according to (14) for use in prevention or treatment of pruritus.

Advantageous Effects of Invention

The compound of the present invention has an excellent μ-opioid receptor antagonistic action, and thus is useful as an agent for preventing or treating pruritus. In addition, since the major compounds of the present invention are antagonistic agents having little agonistic action on μ-opioid receptors and also having high μ-opioid receptor selectivity, the compounds provide safe and useful medicaments with lesser side effects.

DESCRIPTION OF EMBODIMENTS

The compound of the present invention is a compound represented by the following general formula (I), or a pharmacologically acceptable salt thereof. The respective substituents and the preferable embodiments thereof will be described below. In addition, unless otherwise specifically mentioned, Me represents a methyl group, and Et represents an ethyl group.

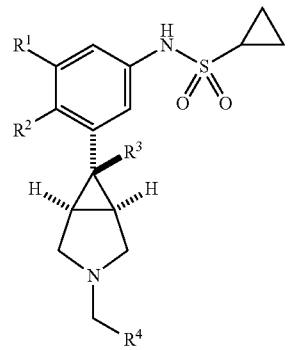

(I)

$R^1$ and $R^2$ are the same or different, and each represents a hydrogen atom or a halogen atom, provided that $R^1$ and $R^2$ are not simultaneously halogen atoms. As the halogen atom for $R^1$ and $R^2$, a fluorine atom is preferable. Furthermore, for $R^1$, a hydrogen atom is preferable.

In a specific embodiment of the general formula (I) of the present invention, each of $R^1$ and $R^2$ is a hydrogen atom.

In a specific embodiment of the general formula (I) of the present invention, $R^1$ is a fluorine atom, and $R^2$ is a hydrogen atom.

In a specific embodiment of the general formula (I) of the present invention, $R^1$ is a hydrogen atom, and $R^2$ is a fluorine atom.

$R^3$ is a $C_1$-$C_3$ alkyl group or a vinyl group, preferably a methyl group, an ethyl group, or a vinyl group, more preferably an ethyl group.

$R^4$ is the formula (II):

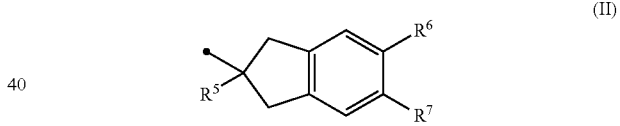

(II)

wherein $R^5$ represents a hydroxy group or a $C_1$-$C_3$ alkoxy group, and $R^6$ and $R^7$ are the same or different, and each represents a hydrogen atom or a halogen atom;

or the formula (III):

(III)

wherein Ring A is a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group.

$R^5$ in the formula (II) is preferably a hydroxy group or a methoxy group.

Each of $R^6$ and $R^7$ in the formula (II) is preferably a hydrogen atom or a fluorine atom, more preferably a hydrogen atom.

The formula (II) is preferably a 2-hydroxy-2,3-dihydro-1H-inden-2-yl group, a 2-methoxy-2,3-dihydro-1H-inden-2-yl group, a 2-ethoxy-2,3-dihydro-1H-inden-2-yl group, or a 5,6-difluoro-2-hydroxy-2,3-dihydro-1H-inden-2-yl group, more preferably a 2-hydroxy-2,3-dihydro-1H-inden-2-yl group, or a 2-methoxy-2,3-dihydro-1H-inden-2-yl group.

In a specific embodiment of the general formula (I) of the present invention, the formula (II) is a 2-hydroxy-2,3-dihydro-1H-inden-2-yl group.

In a specific embodiment of the general formula (I) of the present invention, the formula (II) is a 2-methoxy-2,3-dihydro-1H-inden-2-yl group.

The formula (III) is preferably a 2-(4,4-difluorocyclohexyl)ethyl group, a 2-(4,4-difluoro-1-methoxycyclohexyl)ethyl group, a 2-(1-ethoxy-4,4-difluorocyclohexyl)ethyl group, a 2-(3,3-difluoropyrrolidin-1-yl)ethyl group, a 2-(3,3-difluoropiperidin-1-yl)ethyl group, or a 2-(4,4-difluoropiperidin-1-yl)ethyl group.

The formula (III) is more preferably a 2-(4,4-difluorocyclohexyl)ethyl group, a 2-(4,4-difluoro-1-methoxycyclohexyl)ethyl group, a 2-(3,3-difluoropyrrolidin-1-yl)ethyl group, or a 2-(4,4-difluoropiperidin-1-yl)ethyl group. Further, more preferably, the formula (III) is a 2-(4,4-difluorocyclohexyl)ethyl group or a 2-(4,4-difluoro-1-methoxycyclohexyl)ethyl group.

In a specific embodiment of the general formula (I) of the present invention, the formula (III) is a 2-(4,4-difluorocyclohexyl)ethyl group.

In a specific embodiment of the general formula (I) of the present invention, the formula (III) is a 2-(4,4-difluoro-1-methoxycyclohexyl)ethyl group.

The definitions of the terms used herein are as follows.

"$C_1$-$C_3$ alkyl group" means a straight or branched alkyl group having 1 to 3 carbon atom(s), and examples include a methyl group, an ethyl group, a propyl group, and an isopropyl group.

"$C_5$-$C_7$ cycloalkyl group" means a cyclic saturated aliphatic hydrocarbon group having 5 to 7 carbon atoms, and examples include a cyclopentyl group, a cyclohexyl group, and a cycloheptyl group.

"$C_1$-$C_3$ alkoxy group" means an oxy group to which "$C_1$-$C_3$ alkyl group" defined above is bonded, and examples include a methoxy group, an ethoxy group, a propoxy group, and an isopropoxy group.

"Halogen atom" means a fluorine atom, a chlorine atom, a bromine atom, or an iodine atom.

"5- to 7-membered saturated heterocyclic group" means a saturated heterocyclic group of a 5- to 7-membered ring containing at least one hetero atom(s) such as nitrogen, oxygen, sulfur, and the like, and examples include a tetrahydrofuryl group, a 1,3-dioxolanyl group, a pyrrolidinyl group, a tetrahydropyranyl group, a 1,3-dioxanyl group, a 1,4-dioxanyl group, a piperidinyl group, a piperazinyl group, a morpholinyl group, a thiomorpholinyl group, an azepanyl group, and the like.

"5- to 6-membered nitrogen-containing saturated heterocyclic group" means a saturated heterocyclic group of a 5- to 6-membered ring containing at least one nitrogen atom(s), and examples include a pyrrolidinyl group, a piperidinyl group, a piperazinyl group, a morpholinyl group, and the like.

In the case that an optical isomer, a geometric isomer or a rotational isomer is present in the compound of the present invention represented by the general formula (I), those isomers are also encompassed in the scope of the present invention, and in the case that proton tautomerism is present, those tautomers are also encompassed in the scope of the present invention.

The compound of the present invention represented by the general formula (I) may be formed into a pharmacologically acceptable acidic salt by treating with an acid. Examples of such salt include inorganic acid salts such as a hydrochloride, a hydrobromide, a hydroiodide, a nitrate, a sulfate, a phosphate, and the like; and organic acid salts such as an acetate, a trifluoroacetate, a benzoate, an oxalate, a malonate, a succinate, a maleate, a fumarate, a tartrate, a citrate, a methanesulfonate, an ethanesulfonate, a trifluoromethanesulfonate, a benzenesulfonate, a p-toluenesulfonate, a glutamate, an aspartate, and the like.

The compound of the present invention represented by the general formula (I) may also be formed into a pharmacologically acceptable basic salt by treating with a base. Examples of such salt include metal salts such as a sodium salt, a potassium salt, a calcium salt, a magnesium salt, and the like; inorganic salts such as an ammonium salt and the like; and organic amine salts such as a triethylamine salt, a guanidine salt, and the like.

Furthermore, the compound of the present invention represented by the general formula (I) or a pharmacologically acceptable salt thereof can be present as a hydrate or a solvate, and those are also encompassed in the scope of the present invention.

A general method for producing the compound of the present invention will be represented below. The individual specific method for producing the compound of the present invention will be explained in detail in the Examples described below.

Production Method 1

"Production Method 1" is a method for producing the compound of the present invention represented by the general formula (I).

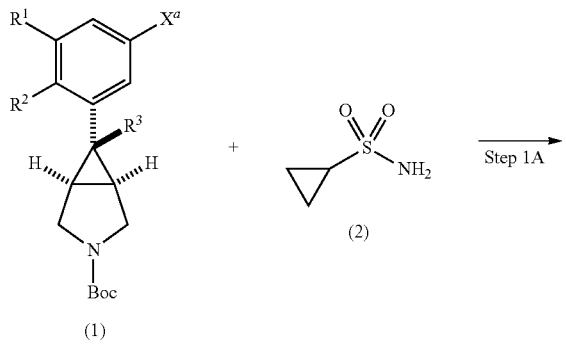

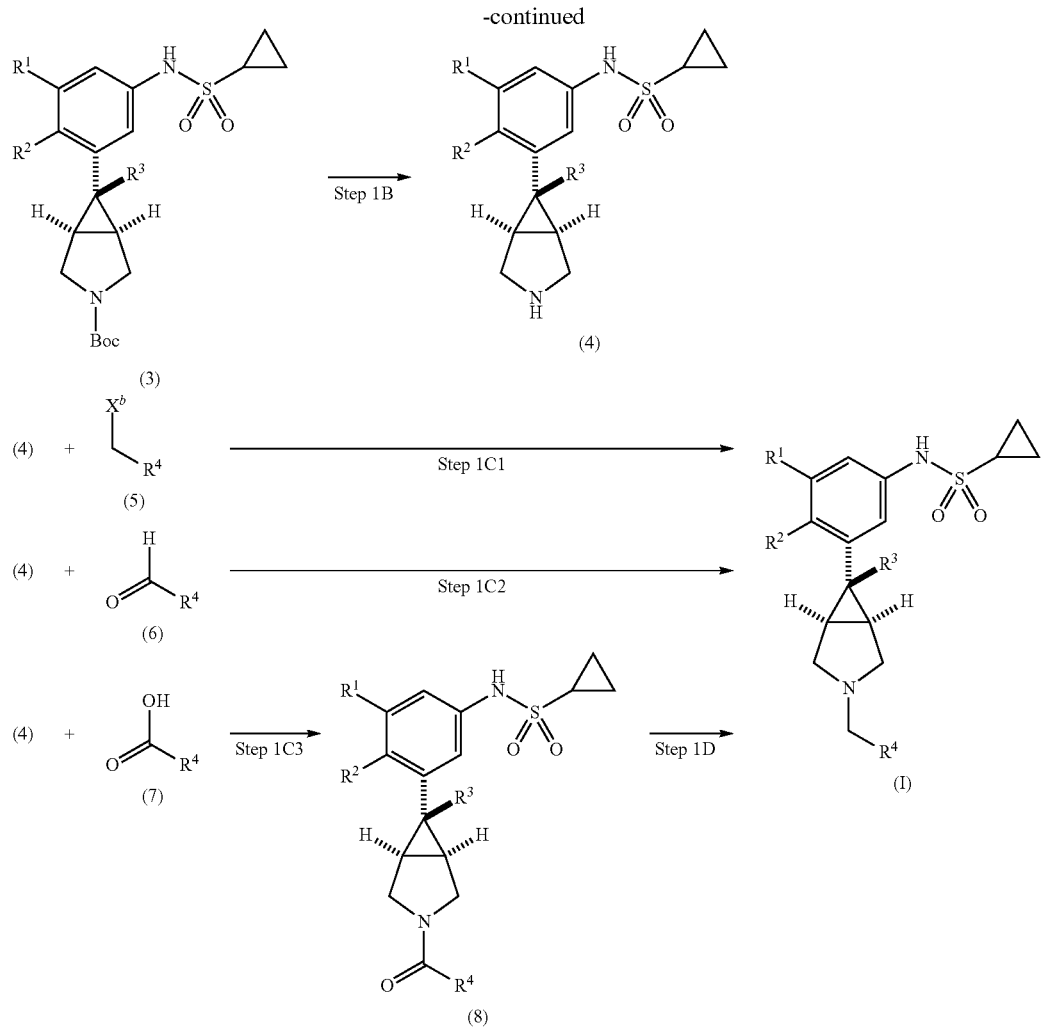

wherein $R^1$, $R^2$, $R^3$ and $R^4$ are as defined above, $X^a$ represents a chlorine atom, a bromine atom, an iodine atom, or a trifluoromethanesulfonyloxy group, $X^b$ represents a chlorine atom, a bromine atom, an iodine atom, a methanesulfonyloxy group, a benzenesulfonyloxy group, a p-toluenesulfonyloxy group, or a trifluoromethanesulfonyloxy group, and Boc represents a tert-butoxycarbonyl group.

"Step 1A" is a step for producing a compound (3) by reacting a compound (1) and a compound (2) under an inert gas atmosphere in an inert solvent in the presence of a palladium catalyst, an organic phosphine compound and a base. The compound (1) and the compound (2) are known, or can be produced from known compounds according to known methods (the compound (1) can be produced with reference to, for example, the method described in Patent Literature 1, Patent Literature 5, WO 2009/027293, Journal of Medicinal Chemistry, 53 (2010) 2534-2551, or the like).

Examples of the inert gas used include helium, nitrogen, argon, and the like.

The inert solvent used is not specifically limited as long as it is an inert solvent that does not inhibit the reaction and dissolves the raw material substances to some extent, and examples include aromatic hydrocarbons such as benzene, toluene, xylene, and the like; ethers such as 1,2-dimethoxyethane, tetrahydrofuran, 2-methyltetrahydrofuran, 1,4-dioxane, and the like; amides such as N,N-dimethylformamide, N,N-dimethylacetamide, N-methylpyrrolidone, and the like; sulfoxides such as dimethylsulfoxide and the like; optional mixed solvents thereof, and the like, and toluene, 2-methyltetrahydrofuran, 1,4-dioxane, or optional mixed solvents thereof are preferable.

Examples of the palladium catalyst used include organic palladium complexes such as tetrakis(triphenylphosphine)palladium, tris(dibenzylideneacetone)dipalladium, dichlorobis(triphenylphosphine) palladium, bis(η3-allyl-μ-chloropalladium), and the like; palladium salts such as dichloropalladium, diacetoxypalladium, and the like, and bis(η3-allyl-μ-chloropalladium) is preferable. The used amount of the palladium catalyst is generally from 0.0001 to 1-fold molar amount, preferably from 0.005 to 0.3-fold molar amount relative to 1 mol of the compound (1).

Examples of the organic phosphine compound used include tri-n-butylphosphine, tri-tert-butylphosphine, tricyclohexylphosphine, butyldi-1-adamantylphosphine, triphenylphosphine, tri(o-tolyl)phosphine, 1,3-bis(diphenylphosphino)propane, 2-(di-tert-butylphosphino)biphenyl, 2-(dicyclohexylphosphino)-2',6'-dimethoxy-1,1'-biphenyl (hereinafter abbreviated as SPhos), 2-(dicyclohexylphosphino)-2',4',6'-triisopropyl-1,1'-biphenyl (hereinafter abbreviated as XPhos), 2-(di-tert-butylphosphino)-2',4',6'-triisopropyl-1,1'-biphenyl (hereinafter abbreviated as tert-butyl XPhos), 2-(di-tert-butylphosphino)-3,4,5,6-tetramethyl-2',4',6'-triisopropyl-1,1'-biphenyl, 1,1'-bis(diphenylphosphino)ferrocene, 1,2,3,4,5-pentaphenyl-1'-(di-tert-butylphosphino)ferrocene, 9,9-dimethyl-4,5-bis(diphenylphosphino)xanthene, and the like, and tert-butyl Xphos or 2-(di-tertbutylphosphino)-3,4,5,6-tetramethyl-2',4',6'-triisopropyl-1,1'-biphenyl is preferable. The used amount of the organic phosphine compound is generally from 0.5 to 5-fold molar amount, preferably from 1 to 3-fold molar amount relative to 1 mol of the palladium.

Examples of the base used include alkali metal acetates such as, sodium acetate, potassium acetate, and the like; alkali metal carbonates such as sodium carbonate, potassium carbonate, cesium carbonate, and the like; alkali metal phosphates such as trisodium phosphate, tripotassium phosphate, and the like; alkali metal alkoxides such as sodium tert-butoxide, potassium tert-butoxide, and the like; and alkali metal hydrides such as sodium hydride, potassium hydride, and the like, and potassium carbonate or cesium carbonate is preferable. The used amount of the base is generally from 0.5 to 10-fold molar amount, preferably from 1 to 5-fold molar amount relative to 1 mol of the compound (1).

In this step, a fluoride may be added so as to promote the reaction. Examples of the fluoride used include potassium fluoride, cesium fluoride, tetramethylammonium fluoride, tetraethylammonium fluoride, tetrabutylammonium fluoride, and the like. The used amount of the fluoride is generally from 0.5 to 10-fold molar amount, preferably from 1 to 5-fold molar amount relative to 1 mol of the compound (1).

The used amount of the compound (2) is generally from 0.5 to 10-fold molar amount, preferably from 1 to 5-fold molar amount relative to 1 mol of the compound (1).

The reaction temperature differs depending on the kinds, used amounts, and the like of the raw materials, solvent, and the like, and is generally from 0° C. to 150° C., preferably from 50° C. to 120° C.

The reaction time differs depending on the reaction temperature and the like, and is generally from 10 minutes to 120 hours, preferably from 30 minutes to 48 hours.

"Step 1B" is a step for producing a compound (4) by removing the Boc group in the compound (3). This step can be carried out by referring to a published document (see T. W. Greene & P. G. M. Wuts, Protective Groups in Organic Synthesis 4th Ed., John Wiley & Sons, Inc., pages 582 and 725), and is carried out by, for example, treating the compound (3) with an acid in an inert solvent, but the step is not limited to this method.

The inert solvent used is not specifically limited as long as it is an inert solvent that does not inhibit the reaction and dissolves the raw material substances to some extent, and examples include ethers such as diethyl ether, 1,2-dimethoxyethane, tetrahydrofuran, 1,4-dioxane, and the like; halogenated aliphatic hydrocarbons such as methylene chloride, chloroform, 1,2-dichloroethane, and the like; water; optional mixed solvents thereof, and the like, and tetrahydrofuran, 1,4-dioxane, methylene chloride, water, or optional mixed solvents thereof are preferable.

Examples of the acid used include hydrogen chloride, hydrochloric acid, hydrobromic acid, hydroiodic acid, sulfuric acid, phosphoric acid, methanesulfonic acid, p-toluenesulfonic acid, trifluoroacetic acid, and the like, and hydrogen chloride, hydrochloric acid, or trifluoroacetic acid is preferable. The used amount of the acid is generally a 1 to 200-fold molar amount, preferably a 5 to 100-fold molar amount relative to 1 mol of the compound (3), or can be used in a large excess amount as a solvent.

In this step, an anisole compound such as anisole, thioanisole, and the like may be added so as to promote the reaction. The used amount of the anisole compound is generally from a 1 to 200-fold molar amount, preferably from a 2 to 100-fold molar amount relative to 1 mol of the compound (3).

The reaction temperature differs depending on the kinds, used amounts, and the like of the raw materials, solvent, and the like, and is generally from −30° C. to 150° C., preferably from 0° C. to 100° C.

The reaction time differs depending on the reaction temperature and the like, and is generally from 10 minutes to 48 hours, preferably from 30 minutes to 24 hours.

"Step 1C1" is a step for producing the compound of the present invention represented by the general formula (I) by reacting the compound (4) and a compound (5) in an inert solvent in the presence of a base. The compound (5) is known, or can be produced from known compounds according to a known method.

The inert solvent used is not specifically limited as long as it is an inert solvent that does not inhibit the reaction and dissolves the raw material substances to some extent, and examples include aromatic hydrocarbons such as benzene, toluene, xylene, and the like; ethers such as diethyl ether, 1,2-dimethoxyethane, tetrahydrofuran, 1,4-dioxane, and the like; halogenated aliphatic hydrocarbons such as methylene chloride, chloroform, 1,2-dichloroethane, and the like; amides such as N,N-dimethylformamide, N,N-dimethylacetamide, N-methylpyrrolidone, and the like; nitriles such as acetonitrile, propionitrile, and the like; alcohols such as methanol, ethanol, propanol, isopropanol, and the like; optional mixed solvents thereof, and the like, and ethanol is preferable.

Examples of the base used include organic bases such as triethylamine, diisopropylethylamine, pyridine, and the like; inorganic bases such as sodium hydrogen carbonate, potassium hydrogen carbonate, sodium carbonate, potassium carbonate, and the like, and triethylamine or diisopropylethylamine is preferable. The used amount of the base is generally from 0.5 to 20-fold molar amount, preferably from 1 to 10-fold molar amount relative to 1 mol of the compound (4).

The used amount of the compound (5) is generally from 0.2 to 10-fold molar amount, preferably from 0.5 to 3-fold molar amount relative to 1 mol of the compound (4).

The reaction temperature differs depending on the kinds, used amounts, and the like of the raw materials, solvent, and the like, and is generally from −30° C. to 200° C., preferably from 0° C. to 150° C.

The reaction time differs depending on the reaction temperature and the like, and is generally from 10 minutes to 120 hours, preferably from 30 minutes to 48 hours.

"Step 1C2" is a step for producing the compound of the present invention represented by the general formula (I), by reacting the compound (4) and a compound (6) in an inert solvent in the presence or absence of a dehydration agent to form an imine form, and then reducing the imine form by using a hydrogenated boron compound. The compound (6) is known, or can be produced from known compounds according to a known method.

The inert solvent used is not specifically limited as long as it is an inert solvent that does not inhibit the reaction and dissolves the raw material substances to some extent, and examples include halogenated aliphatic saturated hydrocarbons such as methylene chloride, chloroform, 1,2-dichloroethane, and the like; alcohols such as methanol, ethanol, propanol, isopropanol, and the like, and methylene chloride or 1,2-dichloroethane is preferable.

Examples of the dehydration agent used include Molecular Sieve (trade name), anhydrous magnesium sulfate, and the like. The used amount of the dehydration agent is generally from 50 g to 2,000 g, preferably from 100 g to 1,000 g relative to 1 mol of the compound (4).

The used amount of the compound (6) is generally from 0.2 to 10-fold molar amount, preferably from 0.5 to 3-fold molar amount relative to 1 mol of the compound (4). In the case when the compound (4) is an acid addition salt (for example, a hydrochloride or the like), a base may be added, and in such case, examples of the base used include trimethylamine, diisopropylethylamine, and the like. The used amount of the base is generally from 0.2 to 10-fold molar amount, preferably from 0.5 to 3-fold molar amount relative to 1 mol of the compound (4).

The reaction temperature differs depending on the kinds, used amounts, and the like of the raw materials, solvent, and the like, and is generally from −30° C. to 150° C., preferably from 0° C. to 100° C.

The reaction time differs depending on the reaction temperature and the like, and is generally from 10 minutes to 48 hours, preferably from 30 minutes to 24 hours.

The obtained imine form is reduced by using a hydrogenated boron compound after being isolated or without being isolated. Examples of the borohydride compound used include sodium borohydride, sodium cyanoborohydride, sodium triacetoxyborohydride and the like, and sodium triacetoxyborohydride is preferable. The used amount of the borohydride compound is generally from 0.5 to 10-fold molar amount, preferably from 1 to 5-fold molar amount relative to 1 mol of the compound (4).

In this step, the reaction for the synthesis of the imine form and the subsequent reduction reaction can be continuously performed in the same system without isolating the imine form, and in the case when the obtained imine form is isolated, the inert solvent used in the reduction reaction is not specifically limited as long as it is an inert solvent that does not inhibit the reaction and dissolves the raw material substances to some extent, and examples include halogenated aliphatic hydrocarbons such as methylene chloride, chloroform, 1,2-dichloroethane, and the like; and alcohols such as methanol, ethanol, propanol, isopropanol, and the like, and methylene chloride or 1,2-dichloroethane is preferable.

The reaction temperature differs depending on the kinds, used amounts, and the like of the raw materials, solvent, and the like, and is generally from −30° C. to 150° C., preferably from 0° C. to 100° C.

The reaction time differs depending on the reaction temperature and the like, and is generally from 10 minutes to 48 hours, preferably from 30 minutes to 24 hours.

"Step 1C3" is a step of producing a compound (8) by converting the carboxy group in a compound (7) to "an active form of a carboxy group" such as an acid chloride, a mixed acid anhydride, an imidazolide, or the like by using an agent for activating a carboxy group in an inert solvent, and reacting the active form with the compound (4) in the presence of a base. The "active form of a carboxy group" can be used in the reaction with the compound (4) without being isolated. The compound (7) is known, or can be produced from known compounds according to a known method.

The inert solvent used is not specifically limited as long as it is an inert solvent that does not inhibit the reaction and dissolves the raw material substances to some extent, and examples include aromatic hydrocarbons such as benzene, toluene, xylene, and the like; ethers such as diethyl ether, 1,2-dimethoxyethane, tetrahydrofuran, 1,4-dioxane, and the like; halogenated aliphatic hydrocarbons such as methylene chloride, chloroform, 1,2-dichloroethane, and the like; amides such as N,N-dimethylformamide, N,N-dimethylacetamide, N-methylpyrrolidone, and the like; nitriles such as acetonitrile, propionitrile, and the like; optional mixed solvents thereof, and the like, and methylene chloride, tetrahydrofuran, N,N-dimethylformamide, acetonitrile, or optional mixed solvents thereof are preferable.

The agent for activating a carboxy group used include chlorides such as thionyl chloride, oxalyl chloride, phosphorus oxychloride, phosphorus pentachloride, and the like; condensing agents such as dicyclohexylcarbodiimide (hereinafter abbreviated as DCC), 1-ethyl-3-(3-dimethylaminopropyl)carbodiimide (hereinafter abbreviated as EDC), O-(benzotriazol-1-yl)-N,N,N',N'-tetramethyluronium hexafluorophosphate (hereinafter abbreviated as HBTU), O-(benzotriazol-1-yl)-N,N,N',N'-tetramethyluronium tetrafluoroborate (hereinafter abbreviated as TBTU), O-(7-azabenzotriazol-1-yl)-N,N,N',N'-tetramethyluronium hexafluorophosphate (hereinafter abbreviated as HATU), (1-cyano-2-ethoxy-2-oxoethylideneaminooxy)dimethylaminomorpholinocarbenium hexafluorophosphate (hereinafter abbreviated as COMU), 1,1-carbonyldiimidazole (hereinafter abbreviated as CDI), and the like; as well as chloroformate esters such as methyl chloroformate, ethyl chloroformate, and the like, and thionyl chloride or a condensing agent is preferable. The used amount of the activating agent is generally from 0.5 to 10-fold molar amount, preferably from 1 to 5-fold molar amount relative to 1 mol of the compound (7).

Examples of the base used include organic bases such as triethylamine, diisopropylethylamine, N,N-dimethylaminopyridine, and the like; inorganic bases such as sodium hydrogen carbonate, potassium hydrogen carbonate, sodium carbonate, potassium carbonate, and the like, and triethylamine, diisopropylethylamine, or N,N-dimethylaminopyridine is preferable. The used amount of the base is generally from 0.5 to 10-fold molar amount, preferably from 1 to 5-fold molar amount relative to 1 mol of the compound (4).

The used amount of the compound (7) is generally from 0.2 to 10-fold molar amount, preferably from 0.5 to 3-fold molar amount relative to 1 mol of the compound (4).

The reaction temperature differs depending on the kinds, used amounts, and the like of the raw materials, solvent, and the like, and is generally from −30° C. to 200° C., preferably from 0° C. to 150° C.

The reaction time differs depending on the reaction temperature and the like, and is generally from 10 minutes to 48 hours, preferably from 30 minutes to 24 hours.

"Step 1D" is a step of producing the compound of the present invention represented by the general formula (I) by reducing the compound (8) in an inert solvent.

The inert solvent used is not specifically limited as long as it is an inert solvent that does not inhibit the reaction and dissolves the raw material substances to some extent, and examples include aromatic hydrocarbons such as benzene, toluene, xylene, and the like; ethers such as diethyl ether, 1,2-dimethoxyethane, tetrahydrofuran, 1,4-dioxane, and the like; halogenated aliphatic hydrocarbons such as methylene chloride, chloroform, 1,2-dichloroethane, and the like; optional mixed solvents thereof, and the like, and tetrahydrofuran is preferable.

Examples of the reducing agent used include alkali metal borohydride compounds such as lithium borohydride, sodium borohydride, and the like; borans such as borantetrahydrofuran complex, N,N-dimethylanilineboran and borane dimethyl sulfide, and the like; lithium aluminum hydride, and the like, and sodium borohydride, borantetrahydrofuran complex, or lithium aluminum hydride is preferable. The used amount of the reducing agent is generally from 0.5 to 20-fold molar amount, preferably from 1 to 10-fold molar amount relative to 1 mol of the compound (8).

In the case when sodium borohydride is used as the reducing agent, it is preferable to add a boron trifluoride-diethyl ether complex. The used amount of the boron trifluoride-diethyl ether complex is generally from 0.2 to 10-fold molar amount, preferably from 0.5 to 3-fold molar amount relative to 1 mol of the sodium borohydride.

The reaction temperature differs depending on the kinds, used amounts, and the like of the raw materials, solvent, and the like, and is generally from −30° C. to 150° C., preferably from 0° C. to 100° C.

The reaction time differs depending on the reaction temperature and the like, and is generally from 10 minutes to 48 hours, preferably from 30 minutes to 24 hours.

Production Method 2

"Production Method 2" is another method for producing the above-mentioned compound (3).

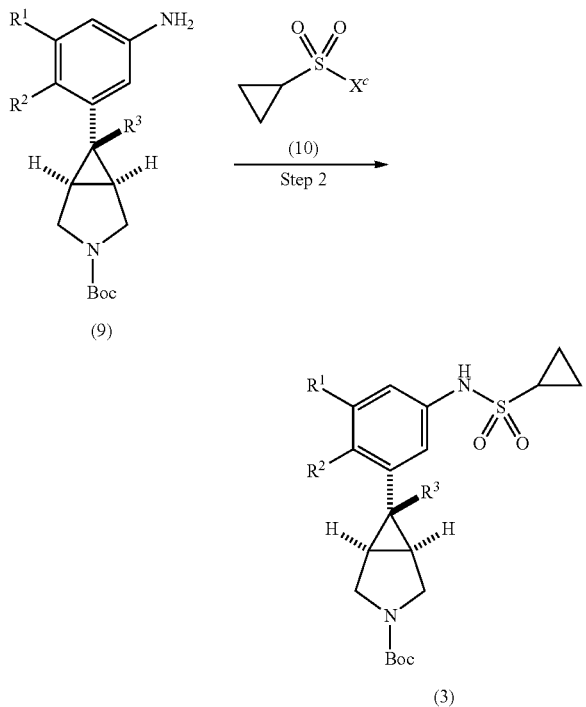

wherein $R^1$, $R^2$, $R^3$ and Boc are as defined above, and $X^c$ represents a chlorine atom, a fluorine atom, or a trifluoromethanesulfonyloxy group.

"Step 2" is a step for producing the compound (3) by reacting a compound (9) and a compound (10) in an inert solvent in the presence of a base. The compound (9) and the compound (10) are known, or can be produced from known compounds according to a known method (the compound (9) can be produced by referring to the method described in, for example, Patent Literature 1, Patent Literature 5, WO2009/027293, Journal of Medicinal Chemistry, 53 (2010) 2534-2551, or the like).

The inert solvent used is not specifically limited as long as it is an inert solvent that does not inhibit the reaction and dissolves the raw material substances to some extent, and examples include aromatic hydrocarbons such as benzene, toluene, xylene, and the like; ethers such as diethyl ether, 1,2-dimethoxyethane, tetrahydrofuran, 1,4-dioxane, and the like; halogenated aliphatic hydrocarbons such as methylene chloride, chloroform, 1,2-dichloroethane, and the like; amides such as N,N-dimethylformamide, N,N-dimethylacetamide, N-methylpyrrolidone, and the like; optional mixed solvents thereof, and the like, and methylene chloride is preferable.

Examples of the base used includes organic bases such as triethylamine, diisopropylethylamine, pyridine, N,N-dimethylaminopyridine, 1,8-diazabicyclo[5.4.0]undec-7-ene (hereinafter abbreviated as DBU), and the like; and inorganic bases such as sodium hydrogen carbonate, potassium hydrogen carbonate, sodium carbonate, potassium carbonate, and the like, and triethylamine or pyridine is preferable. The used amount of the base is generally from 0.5 to 10-fold molar amount, preferably from 1 to 5-fold molar amount relative to 1 mol of the compound (9). In the case when pyridine is used as the base, the pyridine can be used in a large excess amount as the solvent.

The used amount of the compound (10) is generally from 0.2 to 10-fold molar amount, preferably from 0.5 to 3-fold molar amount relative to 1 mol of the compound (9).

The reaction temperature differs depending on the kinds, used amounts, and the like of the raw materials, solvent, and the like, and is generally from −30° C. to 200° C., preferably from 0° C. to 150° C.

The reaction time differs depending on the reaction temperature and the like, and is generally from 10 minutes to 48 hours, preferably from 30 minutes to 24 hours.

Production Method 3

"Production Method 3" is another method for producing the compound of the present invention represented by the general formula (I).

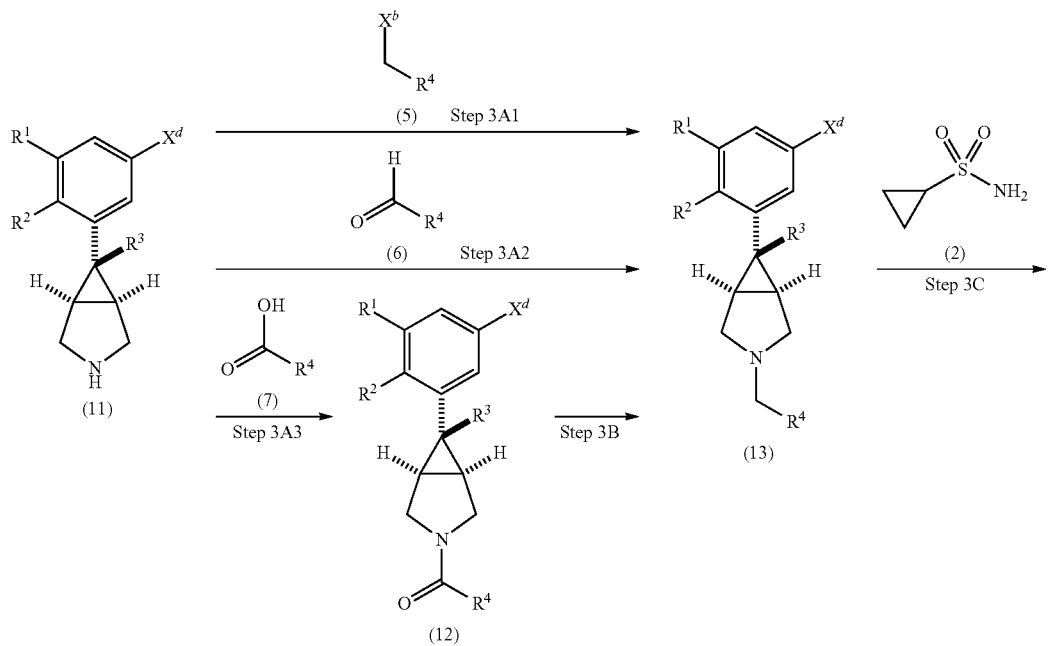

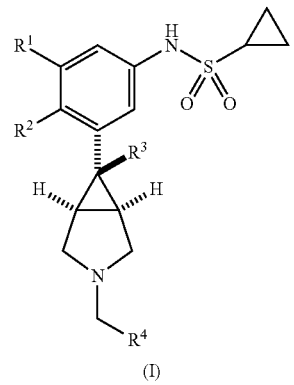

(I)

wherein R¹, R², R³, R⁴, X^b and Boc are as defined above, and X^d represents a chlorine atom, a bromine atom, or an iodine atom.

"Step 3A1" is a step for producing compound (13) by reacting a compound (11) and the above-mentioned compound (5) in an inert solvent in the presence of a base. The compound (11) is known, or can be produced from known compounds according to a known method (the compound (11) can be produced by referring to, for example, Patent Literature 1, Patent Literature 5, WO2009/027293, Journal of Medicinal Chemistry, 53 (2010) 2534-2551, or the like). This step is performed according to the above-mentioned "Step 1C1" except that the compound (11) is used instead of the compound (4).

"Step 3A2" is a step for producing a compound (13) by reacting the compound (11) and the above-mentioned compound (6) in an inert solvent in the presence or absence of a dehydration agent to form an imine form, and reducing the imine form by using a borohydride compound. This step is performed according to the above-mentioned "Step 1C2" except that the compound (11) was used instead of the compound (4).

"Step 3A3" is a step for producing a compound (12) by converting the carboxy group in the above-mentioned compound (7) to "an active form of a carboxy group" such as an acid chloride, a mixed acid anhydride, an imidazolide, or the like by using an agent for activating a carboxy group in an inert solvent, and reacting the active form with the compound (11) in the presence of a base. This step is performed according to the above-mentioned "Step 1C3" except that the compound (11) is used instead of the compound (4).

"Step 3B" is a step for producing a compound (13) by reducing the compound (12) in an inert solvent. This step is performed according to the above-mentioned "Step 1D" except that the compound (12) is used instead of the compound (8).

"Step 3C" is a step for producing the compound of the present invention represented by the general formula (I) by reacting the compound (13) and the above-mentioned compound (2) under an inert gas atmosphere in an inert solvent in the presence of a palladium catalyst, an organic phosphine compound and a base. This step is performed according to the above-mentioned "Step 1A", except that the compound (13) is used instead of the compound (1).

Production Method 4

"Production Method 4" is another method for producing the compound of the present invention represented by the general formula (I).

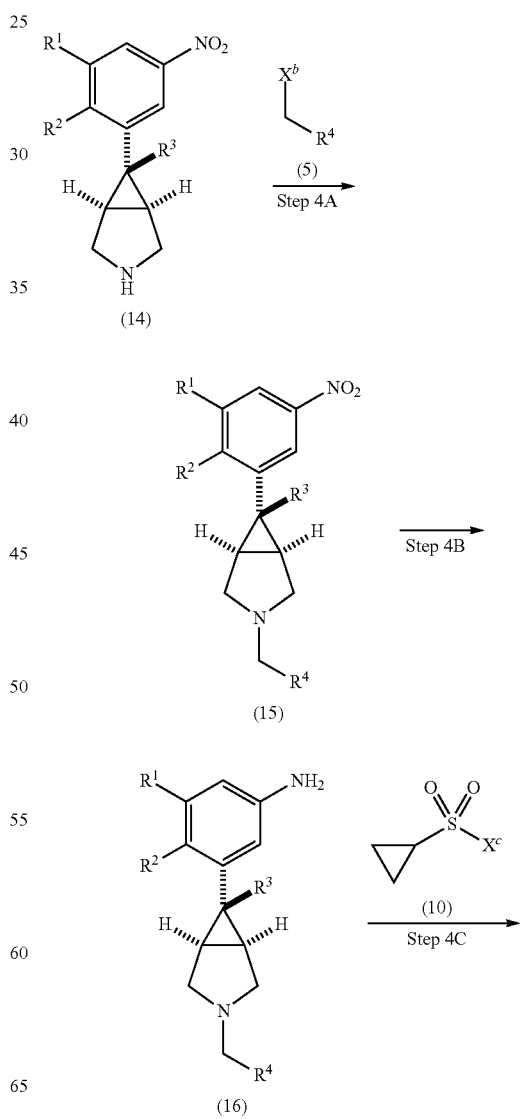

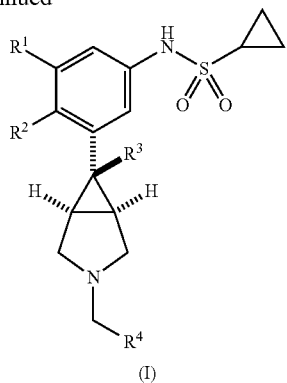

wherein $R^1$, $R^2$, $R^3$, $R^4$, $X^b$ and $X^c$ are defined as above.

"Step 4A" is a step for producing a compound (15) by reacting a compound (14) and the above-mentioned compound (5) in an inert solvent in the presence of a base. The compound (14) is known, or can be produced from known compounds according to a known method (the compound (14) can be produced by referring to the method described in, for example, Patent Literature 1, Patent Literature 5, WO2009/027293, Journal of Medicinal Chemistry, 53 (2010) 2534-2551, or the like). This step is performed according to the above-mentioned "Step 1C1" except that the compound (14) is used instead of the compound (4).

"Step 4B" a step for producing a compound (16) by reducing the compound (15) in an inert solvent.

The inert solvent used is not specifically limited as long as it is an inert solvent that does not inhibit the reaction and dissolves the raw material substances to some extent, and examples include alcohols such as methanol, ethanol, propanol, isopropanol, and the like; water; optional mixed solvents thereof, and the like, and ethanol, water or optional mixed solvents thereof are preferable. The reduction method can be performed, for example, by using a hydrogen gas in the presence of palladium/carbon, platinum/carbon, platinum black, or the like, or by using reduced iron and ammonium chloride.

The reaction temperature differs depending on the kinds, used amounts, and the like of the raw materials, solvent, and the like, and is generally from 0° C. to 150° C., preferably from 0° C. to 100° C.

The reaction time differs depending on the reaction temperature and the like, and is generally from 10 minutes to 48 hours, preferably from 30 minutes to 24 hours.

"Step 4C" is a step for producing the compound of the present invention represented by the general formula (I) by reacting the compound (16) and the above-mentioned compound (10) in an inert solvent in the presence of a base. This step is performed according to the above-mentioned "Step 2" except that the compound (16) was used instead of the compound (9).

Production Method 5

"Production Method 5" is another method for producing the above-mentioned compound (16).

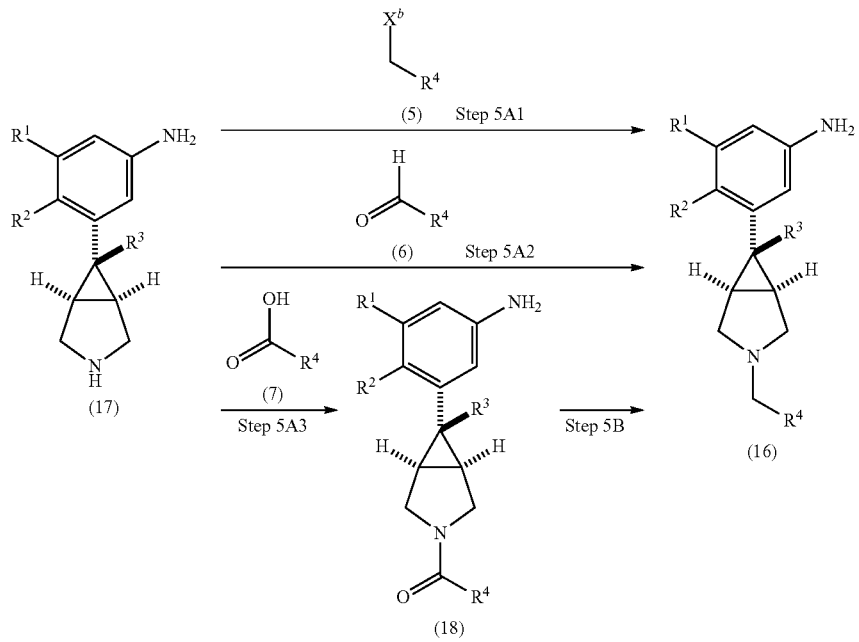

wherein $R^1$, $R^2$, $R^3$, $R^4$ and $X^b$ are defined as above.

"Step 5A1" is a step for producing the compound (16) by reacting a compound (17) and the above-mentioned compound (5) in an inert solvent in the presence of a base. The compound (17) is known, or can be produced from known compounds according to a known method (the compound (17) can be produced by referring to the method described in, for example, Patent Literature 1, Patent Literature 5, WO2009/027293, Journal of Medicinal Chemistry, 53 (2010) 2534-2551, or the like). This step is performed according to the above-mentioned "Step 1C1" except that the compound (17) is used instead of the compound (4).

"Step 5A2" is a step for producing the compound (16) by reacting the compound (17) and the above-mentioned compound (6) in an inert solvent in the presence or absence of a dehydration agent to form an imine form, and reducing the imine form by using a borohydride compound. This step is performed according to the above-mentioned "Step 1C2" except that the compound (17) is used instead of the compound (4).

"Step 5A3" is a step for producing a compound (18) by converting the carboxy group in the above-mentioned compound (7) to "an active form of a carboxy group" such as an acid chloride, a mixed acid anhydride, an imidazolide, or the like by using an agent for activating a carboxy group in an inert solvent, and reacting the active form with the compound (17) in the presence of a base. This step is performed according to the above-mentioned "Step 1C3" except that the compound (17) is used instead of the compound (4)

"Step 5B" is a step for producing the compound (16) by reducing the compound (18) in an inert solvent. This step is performed according to the above-mentioned "Step 1D" except that the compound (18) is used instead of the compound (8).

The compound of the present invention produced by such a way acts as a μ-opioid receptor antagonist drug, and thus can be used as a medicament for preventing or treating pruritus. In addition, the major compounds of the compound of the present invention selectively act on μ-opioid receptors, and show a broad difference between the non protein-binding drug concentration in blood plasma and the $IC_{50}$ value of the hERG inhibitory activity, which represents an anti-itching action, and thus are advantageous in view of side effects.

Examples of specific diseases for which pruritus is to be treated include heat rash, hives, scabies, body trichophytia, atopic dermatitis, contact dermatitis, nummular dermatitis, asteatotic dermatitis, bullous pemphigoid, lichen planus, drug-induced hepatic disorders, hand eczema, tinea pedis, pustulosis palmoplantaris, condylomata acuminata, skin pruritus, primary biliary cirrhosis, cholestasis, hepatitis, diabetes mellitus, chronic renal failure, renal dialysis, chronic conjunctivitis, allergic conjunctivitis, blepharospasm, external otitis, allergic rhinitis, vulval candidiasis, senile vulvitis, vaginal trichomoniasis, anal pruritus, hyperthyroidism, hypothyroidism, malignant tumors, mental disorders, xeroderma, psoriasis, itchiness during infection with HIV, itchiness associated with use of antibody medicaments, and the like. Furthermore, similar effects are expected in mammals other than human.

Furthermore, since the compound of the present invention has a μ-opioid receptor antagonistic action, an effect as an agent for preventing or treating side effects of μ-opioid receptor agonists such as constipation, nausea and vomit, and idiopathic constipation, postoperative ileus, paralytic ileus, irritable bowel syndrome, and the like can be expected. Furthermore, since the compound of the present invention has a μ-opioid receptor antagonistic action, it can be expected that the compound is also useful for the treatment of drug dependence, substance dependence, depression, excess ingestion of opiates, schizophrenia and obesity.

As the dosage form in the case when the compound of the present invention is used as a medicament, various dosage forms described in The General Rules for Preparations of "The Japanese Pharmacopoeia" can be selected depending on the purpose. For example, in forming into a form of a pill agent, it is sufficient to select an orally-ingestible component that is used in the art. Examples include excipients such as lactose, crystalline cellulose, white sugar, potassium phosphate, and the like. Furthermore, if desired, various additives that are generally used in the field of formulation such as a binder, a disintegrator, a lubricant, a deflocculating agent, and the like may be combined.

The amount of the compound of the present invention contained as an active ingredient in the formulation of the present invention is not specifically limited, and is suitably selected from a broad range. The dose of the compound of the present invention is suitably determined depending on the intended use thereof, the age, sex and other conditions of a patient, and the degree of a disease, and in the case of oral administration, a suitable amount per day of the compound of the present invention is from 1 μg to 20 mg, preferably from 10 μg to 2 mg per 1 kg of body weight, and this dose can be suitably administered by dividing into 1 to 4 portions per day. However, the dose and frequency are determined with consideration for relevant circumstances including the degree of a symptom to be treated, selection of a compound to be administered and the selected administration pathway, and thus the above-mentioned range of the dose and frequency do not limit the scope of the present invention.

EXAMPLES

The present invention will further be explained in more detail with indicating Examples (Examples 1 to 20), Reference Examples (Reference Examples 1 to 16) and Test Examples below, but these exemplifications are for better understanding of the present invention and not for limiting the scope of the present invention. In addition, DUIS in an ionization mode of a mass spectrum is a mix mode of ESI and APCI.

Example 1

N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)cyclopropanesulfonamide

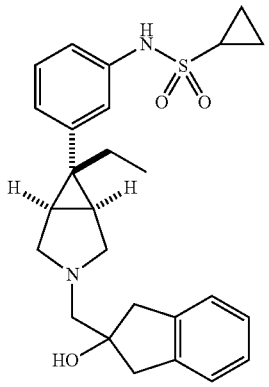

Example 1-(a)

N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)cyclopropanesulfonamide (free form)

120 mg (0.495 mmol) of (2-hydroxy-2,3-dihydro-1H-inden-2-yl)methyl methanesulfonate, which was obtained by a similar method to that of Reference Example 2-(b), and 350 μl (2.51 mmol) of triethylamine were added to a solution of 200 mg (0.583 mmol) of N-{3-[(1R,5S,6r)-6-ethyl-3-azabicyclo[3.1.0]hexan-6-yl]

phenyl}cyclopropanesulfonamide hydrochloride, which was obtained by a similar method to that of Reference Example 1-(d), in 10 ml of ethanol, and the resultant was stirred at room temperature for 21 hours. After the reaction was completed, water was added to the reaction solution, the resultant was extracted by methylene chloride, and the extract was dried over anhydrous sodium sulfate and concentrated under a reduced pressure. The residue was subjected to silica gel column chromatography (elution solvent; toluene:ethyl acetate=50:50 (V/V)), and the fraction containing the objective product was concentrated under a reduced pressure to obtain 98 mg of a colorless oil. This colorless oil was dissolved in 1 ml of ethyl acetate, the solution was subjected to a ultrasonic treatment, a small amount of hexane was added thereto, the solution was stirred, and the precipitated solid was collected by filtration. The obtained solid was dried at 40° C. under a reduced pressure to give 53.5 mg of the titled compound as a white solid. (Yield 24%)

Mass spectrum (CI, m/z): 453[M$^+$+1].

$^1$H-NMR spectrum (400 MHz, DMSO-d$_6$) δppm: 9.58 (0.9H, br s), 7.20 (1H, dd, J=7.8, 7.8 Hz), 7.19-7.06 (5H, m), 7.05-6.99 (1H, m), 6.99-6.94 (1H, m), 4.52 (1H, s), 3.14 (2H, d, J=9.8 Hz), 2.99 (2H, d, J=16.2 Hz), 2.95-2.85 (2H, m), 2.80 (2H, d, J=16.2 Hz), 2.64 (2H, s), 2.55 (1H, tt, J=7.6, 5.2 Hz), 1.90 (2H, q, J=7.4 Hz), 1.72-1.66 (2H, m), 0.92-0.86 (4H, m), 0.77 (3H, t, J=7.4 Hz).

Example 1-(b)

N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)cyclopropanesulfonamide hydrochloride Under an argon airflow, 60 μl (0.24 mmol) of a 4 N hydrogen chloride/1,4-dioxane solution was added to a solution of 86 mg (0.19 mmol) of N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)cyclopropanesulfonamide, which was obtained by a similar method to that of Example 1-(a), in 2.0 ml of ethyl acetate, and the resultant was stirred at 40° C. and then stirred at room temperature for 30 minutes. After the reaction was completed, the reaction solution was concentrated under a reduced pressure. 2.0 ml of acetone was added to the residue, the resultant was stirred at room temperature for 1 hour, and the precipitated solid was collected by filtration and dried under a reduced pressure to give 82 mg of a white solid. 40 mg of the obtained white solid was dissolved in 0.5 ml of methanol, 1.5 ml of ethyl acetate was added thereto, and the resultant was stirred at 40° C. for 10 minutes. The reaction solution was concentrated under a reduced pressure, a small amount of ethyl acetate was added thereto, and the resultant was stirred at room temperature for 20 minutes. The precipitated solid was collected by filtration to give 27 mg of the titled compound as a white solid. (Yield 60%, calculated as a monohydrochloride)

Mass spectrum (CI, m/z): 453[M$^+$+1].

$^1$H-NMR spectrum (400 MHz, CD$_3$OD) δppm: 7.29 (1H, dd, J=7.8, 7.8 Hz), 7.28-7.21 (3H, m), 7.21-7.15 (2H, m), 7.15-7.07 (2H, m), 4.62-3.90 (2H, m), 3.64-3.43 (2H, m), 3.27-3.00 (2H, m), 3.21 (2H, d, J=16.1 Hz), 3.06 (2H, d, J=16.1 Hz), 2.52 (1H, tt, J=7.9, 4.9 Hz), 2.42-2.26 (2H, m), 1.83 (2H, q, J=7.3 Hz), 1.06-0.84 (4H, m), 0.89 (3H, t, J=7.3 Hz).

Example 2

N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide

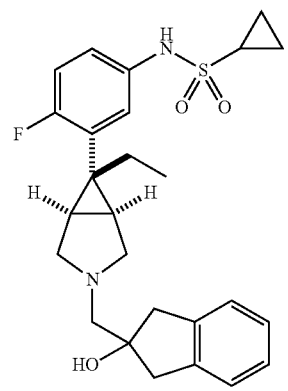

Example 2-(a)

N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide (free form)

620 mg (1.72 mmol) of N-{3-[(1R,5S,6r)-6-ethyl-3-azabicyclo[3.1.0]hexan-6-yl]-4-fluorophenyl}cyclopropanesulfonamide hydrochloride, which was obtained by a similar method to that of Reference Example 3-(d), and 570 μl (4.10 mmol) of triethylamine were added to a solution of 500 mg (2.06 mmol) of (2-hydroxy-2,3-dihydro-1H-inden-2-yl)methyl methanesulfonate, which was obtained by a similar method to that of Reference Example 2-(b), in 12 ml of ethanol, and the resultant was refluxed under heating for 14 hours. After the reaction was completed, the reaction solution was concentrated under a reduced pressure. A saturated aqueous sodium hydrogen carbonate solution was added to the residue, and the resultant was extracted by ethyl acetate, dried over anhydrous sodium sulfate and concentrated under a reduced pressure. The residue was subjected to silica gel column chromatography (DIOL type (manufactured by Fuji Silycia Chemical Ltd.), elution solvent; hexane:ethyl acetate=90:10→50:50 (V/V)), and the fraction containing the objective product was concentrated under a reduced pressure to give 691 mg of the titled compound as a colorless oil. (Yield 86%)

Mass spectrum (CI, m/z): 471[M$^+$+1].

$^1$H-NMR spectrum (400 MHz, CDCl$_3$) δppm: 7.24-7.13 (5H, m), 7.08 (1H, ddd, J=8.8, 4.3, 2.8 Hz), 6.98 (1H, dd, J=9.3, 8.8 Hz), 6.17 (0.8H, br s), 3.43 (0.7H, br s), 3.27 (2H, d, J=9.7 Hz), 3.12-3.05 (2H, m), 3.00 (2H, d, J=16.9 Hz), 3.00 (2H, d, J=16.9 Hz), 2.83 (2H, s), 2.42 (1H, tt, J=8.0, 4.8 Hz), 1.93-1.80 (2H, m), 1.88 (2H, q, J=7.5 Hz), 1.17-1.10 (2H, m), 0.99-0.92 (2H, m), 0.89-0.82 (3H, m).

Example 2-(b)

N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide hydrochloride 1.37 ml (5.48 mmol) of a 4 N hydrogen chloride/ethyl acetate solution was added to a solution of 1.29 g (2.74 mmol) of N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide, which was obtained in a similar method to that of Example 2-(a), in 20 ml of ethyl acetate, and the resultant was stirred at room temperature for 10 minutes. After the reaction was completed, reaction solution was concentrated under a reduced pressure. 10 ml of acetone was added to the residue, the resultant was stirred at 50° C. and then stirred at room temperature for 1 hour, and the precipitated solid was collected by filtration. The obtained solid was dried at 50° C. under a reduced pressure to give 1.32 g of the titled compound as a white solid. (Yield 95%, calculated as a monohydrochloride)

Mass spectrum (CI, m/z): 471[M$^+$+1].

$^1$H-NMR spectrum (400 MHz, CD$_3$OD) δppm: 7.27-7.15 (6H, m), 7.07 (1H, dd, J=9.9, 8.8 Hz), 4.70-3.95 (2H, m), 3.56 (2H, s), 3.26-3.01 (2H, m), 3.21 (2H, d, J=16.2 Hz), 3.07 (2H, d, J=16.2 Hz), 2.49 (1H, tt, J=7.7, 5.0 Hz), 2.42-2.28 (2H, m), 1.81 (2H, q, J=7.3 Hz), 1.02-0.87 (4H, m), 0.91 (3H, t, J=7.3 Hz).

Example 3

N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide

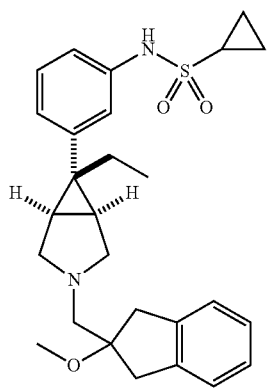

Example 3-(a)

N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide (free form)

150 mg (0.437 mmol) of N-{3-[(1R,5S,6r)-6-ethyl-3-azabicyclo[3.1.0]hexan-6-yl]phenyl}cyclopropane sulfonamide hydrochloride, which was obtained in a similar method to that of Reference Example 1-(d), and 61 μl (0.44 mmol) of triethylamine were added to a solution of 123 mg (0.698 mmol) of 2-methoxy-2,3-dihydro-1H-indene-2-carboaldehyde, which was obtained in Reference Example 4-(b), in 2.0 ml of methylene chloride, and the resultant was stirred at room temperature for 10 minutes. 222 mg (1.05 mmol) of sodium triacetoxyborohydride was then added thereto, and the resultant was stirred at room temperature for 3 hours. After the reaction was completed, water and a saturated aqueous sodium hydrogen carbonate solution were added to the reaction solution, and the resultant was extracted with methylene chloride. The organic layer was dried over anhydrous magnesium sulfate and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 89 mg of the titled compound as a colorless oil. (Yield 44%)

$^1$H-NMR spectrum (400 MHz, CDCl$_3$) δppm: 7.23 (1H, dd, J=7.8, 7.8 Hz), 7.20-7.11 (5H, m), 7.11-7.07 (1H, m), 7.04 (1H, ddd, J=7.8, 2.3, 1.0 Hz), 6.23 (0.8H, br s), 3.24 (3H, s), 3.17 (2H, d, J=9.5 Hz), 3.11 (2H, d, J=16.6 Hz), 3.00-2.92 (2H, m), 3.00 (2H, d, J=16.6 Hz), 2.74 (2H, s), 2.45 (1H, tt, J=8.0, 4.8 Hz), 1.95 (2H, q, J=7.4 Hz), 1.80-1.65 (2H, m), 1.19-1.12 (2H, m), 0.99-0.91 (2H, m), 0.82 (3H, t, J=7.4 Hz).

Example 3-(b)

N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide hydrochloride 68 μl (0.27 mmol) of a 4 N hydrogen chloride/1,4-dioxane solution was added to a solution of 85 mg (0.18 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide, which was obtained in Example 3-(a), in 1.0 ml of 1,4-dioxane, and the resultant was stirred at room temperature for 10 minutes. After the reaction was completed, the reaction solution was concentrated under a reduced pressure. 1.0 ml of ethanol was added to the residue, and the precipitated solid was collected by filtration and dried at 50° C. under a reduced pressure to give 97 mg of the titled compound as a white solid quantitatively. (Calculated as a monohydrochloride)

Mass spectrum (FAB, m/z): 467[M$^+$+1].

$^1$H-NMR spectrum (400 MHz, CD$_3$OD) δppm: 7.29 (1H, dd, J=8.0, 7.9 Hz), 7.28-7.16 (5H, m), 7.13 (1H, ddd, J=8.0, 2.2, 0.9 Hz), 7.12-7.06 (1H, m), 4.67-3.90 (2H, m), 3.67-3.54 (2H, m), 3.28-3.04 (6H, m), 3.14 (3H, s), 2.52 (1H, tt, J=7.9, 4.9 Hz), 2.43-2.24 (2H, m), 1.84 (2H, q, J=7.3 Hz), 1.05-0.85 (4H, m), 0.88 (3H, t, J=7.3 Hz).

Example 4

N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide

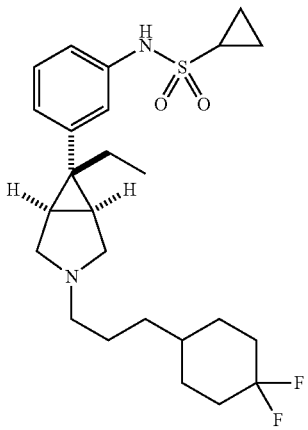

Example 4-(a)

N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide (free form)

924 mg (2.69 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), 380 μl (2.70 mmol) of triethylamine, and 1.43 g (6.75 mmol) of sodium triacetoxyborohydride were added to a solution of 550 mg (3.12 mmol) of 3-(4,4-difluorocyclohexyl)propanal, which was obtained in Reference Example 5-(d), in 12 ml of methylene chloride, and the resultant was stirred at room temperature for 2 hours. After the reaction was completed, a saturated aqueous sodium hydrogen carbonate solution was added to the reaction solution, and the resultant was extracted with ethyl acetate. The organic layer was dried over anhydrous sodium sulfate and then concentrated under a reduced pressure. The residue was subjected to silica gel column chromatography (DNH type (manufactured by Fuji Silycia Chemical Ltd.), elution solvent; hexane:ethyl acetate=96:4→52:48 (V/V)), and the fraction containing the objective product was concentrated under a reduced pressure to give 1.11 g of the titled compound as a colorless oil. (Yield 88%)

$^1$H-NMR spectrum (400 MHz, CDCl$_3$) δppm: 7.23 (1H, dd, J=7.8, 7.8 Hz), 7.15 (1H, dd, J=2.0, 1.8 Hz), 7.12-7.07 (1H, m), 7.03 (1H, ddd, J=7.8, 2.0, 1.0 Hz), 6.21 (0.6H, br s), 2.97 (2H, d, J=9.5 Hz), 2.82-2.73 (2H, m), 2.49-2.38 (3H, m), 2.13-2.00 (2H, m), 1.95 (2H, q, J=7.4 Hz), 1.82-1.19 (13H, m), 1.19-1.12 (2H, m), 0.98-0.91 (2H, m), 0.81 (3H, t, J=7.4 Hz).

Example 4-(b)

N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide hydrochloride 1.5 ml (6.0 mmol) of a 4 N hydrogen chloride/ethyl acetate solution was added to a solution of 1.42 g (3.04 mmol) of N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide, which was obtained in Example 4-(a), in 15 ml of ethyl acetate, and the resultant was stirred at room temperature for 15 minutes. After the reaction was completed, the reaction solution was concentrated under a reduced pressure. 15 ml of acetone was added to the residue, and the resultant was concentrated under a reduced pressure. Furthermore, 15 ml of acetone was added to the residue, and the resultant was stirred at room temperature for 2 hours. The precipitated solid was collected by filtration, and dried at 45° C. under a reduced pressure to give 1.10 g of the titled compound as a white solid. (Yield 72%, calculated as a monohydrochloride)

Mass spectrum (CI, m/z): 467[M$^+$+1].

$^1$H-NMR spectrum (400 MHz, CD$_3$OD) δppm: 7.28 (1H, dd, J=7.9, 7.8 Hz), 7.24 (1H, dd, J=2.0, 1.9 Hz), 7.12 (1H, ddd, J=7.9, 2.0, 1.0 Hz), 7.10-7.06 (1H, m), 4.61-3.73 (2H, m), 3.40-2.85 (4H, t), 2.51 (1H, tt, J=7.8, 4.9 Hz), 2.37-2.28 (2H, m), 2.10-1.97 (2H, m), 1.88-1.65 (8H, m), 1.51-1.19 (5H, m), 1.04-0.85 (4H, m), 0.87 (3H, t, J=7.3 Hz).

Example 5

N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide

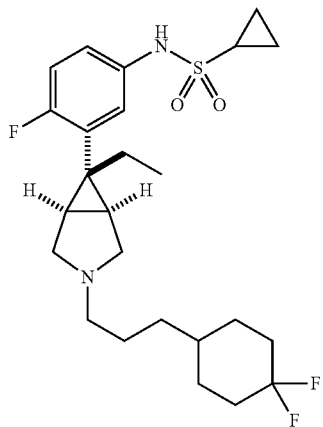

Example 5-(a)

N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide (free form)

343 mg (0.950 mmol) of N-{3-[(1R,5S,6r)-6-ethyl-3-azabicyclo[3.1.0]hexan-6-yl]-4-fluorophenyl}cyclopropane sulfonamide hydrochloride, which was obtained in a similar method to that of Reference Example 3-(d), 133 μl (0.954 mmol) of triethylamine and 503 mg (2.37 mmol) of sodium triacetoxyborohydride were added to a solution of 175 mg (0.993 mmol) of 3-(4,4-difluorocyclohexyl)propanal, which was obtained in a similar method to that of Reference Example 5-(d), in 4.0 ml of methylene chloride, and the resultant was stirred at room temperature for 24 hours. After the reaction was completed, a saturated aqueous sodium hydrogen carbonate solution was added to the reaction solution, and the resultant was extracted with ethyl acetate. The organic layer was dried over anhydrous magnesium sulfate and concentrated under a reduced pressure. The residue was subjected to silica gel column chromatography (DIOL type (manufactured by Fuji Silycia Chemical Ltd.), elution solvent; hexane:ethyl acetate=50:50 (V/V)), and the fraction containing the objective product was concentrated under a reduced pressure to give 370 mg of the titled compound as a colorless oil. (Yield 80%)

$^1$H-NMR spectrum (400 MHz, CDCl$_3$) δppm: 7.16 (1H, dd, J=6.3, 2.8 Hz), 7.07 (1H, ddd, J=8.7, 4.3, 2.8 Hz), 6.96 (1H, dd, J=9.5, 8.7 Hz), 6.16 (0.7H, br s), 3.02 (2H, d, J=9.7 Hz), 2.81-2.71 (2H, m), 2.46-2.36 (3H, m), 2.13-2.00 (2H, m), 1.93 (2H, q, J=7.5 Hz), 1.82-1.18 (13H, m), 1.15-1.08 (2H, m), 0.99-0.91 (2H, m), 0.84-0.77 (3H, m).

Example 5-(b)

N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide hydrochloride 1.0 ml (4.0 mmol) of 4 N hydrogen chloride/ethyl acetate solution was added to a solution of 360 mg (0.743 mmol) of N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide, which was obtained in Example 5-(a), in 5.0 ml of ethyl acetate, and the resultant was stirred at room temperature for 10 minutes. After the reaction was completed, the reaction solution was concentrated under a reduced pressure. 5.0 ml of ethyl acetate was added to the residue, and the resultant was stirred at room temperature for 12 hours. The precipitated solid was collected by filtration and dried at 45° C. under a reduced pressure to give 335 mg of the titled compound as a white solid. (Yield 87%, calculated as a monohydrochloride)

Mass spectrum (CI, m/z): 485[M$^+$+1].

$^1$H-NMR spectrum (400 MHz, CD$_3$OD) δppm: 7.23 (1H, dd, J=6.4, 2.7 Hz), 7.18 (1H, ddd, J=8.8, 4.4, 2.7 Hz), 7.07 (1H, dd, J=9.9, 8.8 Hz), 4.62-3.75 (2H, m), 3.45-2.90 (4H, m), 2.48 (1H, tt, J=7.8, 5.0 Hz), 2.38-2.28 (2H, m), 2.10-1.97 (2H, m), 1.88-1.65 (8H, m), 1.50-1.20 (5H, m), 1.00-0.87 (4H, m), 0.90 (3H, t, J=7.3 Hz).

Example 6

N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide

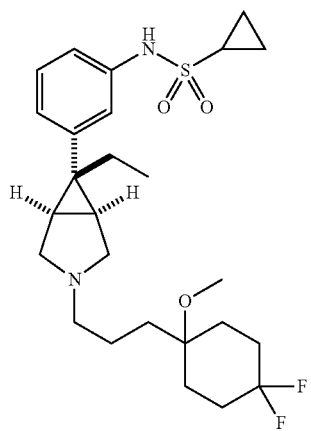

Example 6-(a)

N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide (free form)

400 mg (1.17 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), 165 µl (1.18 mmol) of triethylamine and 600 mg (2.83 mmol) of sodium triacetoxyborohydride 600 mg (2.83 mmol) were added to a solution of 241 mg (1.17 mmol) of 3-(4,4-difluoro-1-methoxycyclohexyl)propanal, which was obtained in a similar method to that of Reference Example 6-(d), in 4.0 ml of methylene chloride, and the resultant was stirred at room temperature for 1 hour. After the reaction was completed, 1.0 ml of methanol and 1.0 ml of 2 N hydrochloric acid were then added to the reaction solution, and the resultant was stirred at room temperature for 30 minutes. A saturated aqueous sodium hydrogen carbonate solution was then added thereto, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=26:74→5:95 (V/V)), the fraction containing the objective product was concentrated under a reduced pressure, the obtained residue was further subjected to silica gel column chromatography (DNH type (manufactured by Fuji Silycia Chemical Ltd.), elution solvent; hexane:ethyl acetate=78:22→57:43 (V/V)), and the fraction containing the objective product was concentrated under a reduced pressure to give 570 mg of the titled compound as a colorless oil. (Yield 98%)

Mass spectrum (CI, m/z): 497[M$^+$+1].

$^1$H-NMR spectrum (400 MHz, CDCl$_3$) δppm: 7.23 (1H, dd, J=7.8, 7.8 Hz), 7.16 (1H, dd, J=2.1, 1.9 Hz), 7.12-7.07 (1H, m), 7.03 (1H, ddd, J=7.8, 2.1, 1.1 Hz), 6.17 (0.7H, br s), 3.15 (3H, s), 3.01 (2H, d, J=9.4 Hz), 2.81-2.71 (2H, m), 2.49-2.41 (3H, m), 2.08-1.82 (8H, m), 1.79-1.73 (2H, m), 1.60-1.39 (6H, m), 1.19-1.13 (2H, m), 0.98-0.91 (2H, m), 0.81 (3H, t, J=7.4 Hz).

Example 6-(b)

N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide hydrochloride 861 µl (3.44 mmol) of a 4 N hydrogen chloride/ethyl acetate solution was added to a solution of 570 mg (1.15 mmol) of N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide, which was obtained in Example 6-(a), in 3.0 ml of ethyl acetate, and the resultant was stirred at room temperature for 30 minutes. After the reaction was completed, the reaction solution was concentrated under a reduced pressure. 1.0 ml of acetone was added to the residue, and the resultant was stirred for 1 hour. The precipitated solid was collected by filtration and dried under a reduced pressure to give 475 mg of the titled compound as a white solid.
(Yield 78%, calculated as a monohydrochloride)
Mass spectrum (CI, m/z): 497[M$^+$+1].

¹H-NMR spectrum (400 MHz, CD₃OD) δppm: 7.28 (1H, dd, J=8.0, 7.8 Hz), 7.25 (1H, dd, J=2.0, 1.9 Hz), 7.12 (1H, ddd, J=8.0, 2.0, 1.1 Hz), 7.1 (1H, ddd, J=7.8, 1.9, 1.1 Hz), 4.10-3.75 (2H, m), 3.30-2.97 (4H, m), 3.18 (3H, s), 2.51 (1H, tt, J=7.9, 4.9 Hz), 2.36-2.27 (2H, m), 2.06-1.45 (14H, m), 1.05-0.85 (4H, m), 0.88 (3H, t, J=7.3 Hz).

Example 7

N-(3-{(1R,5S,6r)-3-[3-(4,4-difluoropiperidin-1-yl) propyl]-6-ethyl-3-azabicyclo[3.1.0]hexan-6-yl}phenyl)cyclopropanesulfonamide

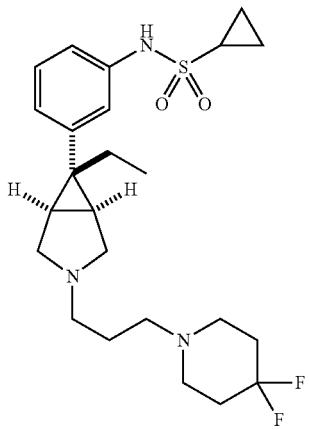

Example 7-(a)

N-(3-{(1R,5S,6r)-3-[3-(4,4-difluoropiperidin-1-yl) propyl]-6-ethyl-3-azabicyclo[3.1.0]hexan-6-yl}phenyl)cyclopropanesulfonamide (free form)

2.44 ml (17.5 mmol) of triethylamine was added to a solution of 1.17 g (4.83 mmol) of 1-(3-bromopropyl)-4,4-difluoropiperidine, which was obtained in Reference Example 7-(a), and 1.50 g (4.37 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), in 3.0 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (DNH type (manufactured by Fuji Silycia Chemical Ltd.), elution solvent; hexane:ethyl acetate=65:35→44:56 (V/V)), and the fraction containing the objective product was concentrated under a reduced pressure to give 2.3 g of the titled compound as a colorless oil quantitatively.

¹H-NMR spectrum (400 MHz, CDCl₃) δppm: 7.23 (1H, dd, J=7.8, 7.9 Hz), 7.16 (1H, dd, J=2.0, 1.6 Hz), 7.09 (1H, ddd, J=7.8, 1.6, 1.1 Hz), 7.03 (1H, ddd, J=7.9, 2.0, 1.1 Hz), 6.25 (0.5H, br s), 3.00 (2H, d, J=9.5 Hz), 2.78-2.76 (2H, m), 2.62-2.38 (9H, m), 2.06-1.90 (6H, m), 1.80-1.73 (2H, m), 1.66-1.64 (2H, m), 1.18-1.13 (2H, m), 0.97-0.92 (2H, m), 0.81 (3H, t, J=7.4 Hz).

Example 7-(b)

N-(3-{(1R,5S,6r)-3-[3-(4,4-difluoropiperidin-1-yl) propyl]-6-ethyl-3-azabicyclo[3.1.0]hexan-6-yl}phenyl)cyclopropanesulfonamide hydrochloride 3.69 ml (14.8 mmol) of a 4 N hydrogen chloride/1,4-dioxane solution was added to a solution of 2.3 g (4.92 mmol) of N-(3-{(1R,5S,6r)-3-[3-(4,4-difluoropiperidin-1-yl)propyl]-6-ethyl-3-azabicyclo[3.1.0]hexan-6-yl}phenyl)cyclopropanesulfonamide, which was obtained in Example 7-(a), in 10 ml of 1,4-dioxane, and the resultant was stirred at room temperature for 10 minutes. After the reaction was completed, the reaction solution was concentrated under a reduced pressure. 2.0 ml of ethanol was added to the residue, and the precipitated solid was collected by filtration and dried at 50° C. under a reduced pressure to give 1.74 g of the titled compound as a white solid. (Yield 65%, calculated as a dihydrochloride)

Mass spectrum (CI, m/z): 468[M⁺+1].

¹H-NMR spectrum (400 MHz, CD₃OD) δppm: 7.29 (1H, dd, J=8.0, 7.8 Hz), 7.25 (1H, dd, J=2.0, 1.6 Hz), 7.13 (1H, ddd, J=8.0, 2.0, 1.1 Hz), 7.09 (1H, ddd, J=7.8, 1.6, 1.1 Hz), 4.30-3.50 (4H, m), 3.45-2.90 (8H, m), 2.58-2.16 (8H, m), 2.51 (1H, tt, J=7.8, 4.9 Hz), 1.87-1.70 (2H, m), 1.05-0.85 (4H, m), 0.88 (3H, t, J=7.3 Hz).

Example 8

N-(3-{(1R,5S,6r)-3-[3-(3,3-difluoropyrrolidin-1-yl) propyl]-6-ethyl-3-azabicyclo[3.1.0]hexan-6-yl}phenyl)cyclopropanesulfonamide

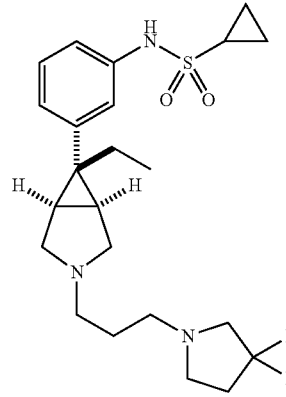

Example 8-(a)

N-(3-{(1R,5S,6r)-3-[3-(3,3-difluoropyrrolidin-1-yl) propyl]-6-ethyl-3-azabicyclo[3.1.0]hexan-6-yl}phenyl)cyclopropanesulfonamide (free form)

0.30 g (0.88 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), and 360 μl (2.6 mmol) of triethylamine were added to a solution of 0.33 g (1.36 mmol) of 3-(3,3-difluoropyrrolidin-1-yl)propylmethanesulfonate obtained in Reference Example 8-(b), in 3.0 ml of ethanol, and the resultant was stirred at 90° C. for 5 hours. After the reaction was completed, a saturated aqueous ammonium chloride solution was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=80:20→60:40 (V/V)), and the fraction containing the objective product was concentrated under a reduced pressure to give 250 mg of the titled compound as a colorless oil. (Yield 63%)

Mass spectrum (CI, m/z): 454[M⁺+1].

¹H-NMR spectrum (400 MHz, CDCl₃) δppm: 7.23 (1H, dd, J=7.8, 7.8 Hz), 7.15 (1H, dd, J=2.1, 1.9 Hz), 7.12-7.07 (1H, m), 7.04 (1H, ddd, J=7.8, 2.1, 1.1 Hz), 6.18 (0.8H, br s), 3.00 (2H, d, J=9.5 Hz), 2.89 (2H, t, J=13.3 Hz), 2.81-2.70 (2H, m), 2.72 (2H, t, J=7.0 Hz), 2.53-2.41 (5H, m), 2.27 (2H, tt, J=14.6, 7.4 Hz), 1.95 (2H, q, J=7.4 Hz), 1.80-1.72 (2H, m), 1.62 (2H, tt, J=7.4, 7.4 Hz), 1.19-1.13 (2H, m), 0.98-0.91 (2H, m), 0.81 (3H, t, J=7.4 Hz).

Example 8-(b)

N-(3-{(1R,5S,6r)-3-[3-(3,3-difluoropyrrolidin-1-yl)propyl]-6-ethyl-3-azabicyclo[3.1.0]hexan-6-yl}phenyl)cyclopropanesulfonamide hydrochloride 413 μl (1.65 mmol) of a 4 N hydrogen chloride/ethyl acetate solution was added to a solution of 250 mg (0.551 mmol) of N-(3-{(1R,5S,6r)-3-[3-(3,3-difluoropyrrolidin-1-yl)propyl]-6-ethyl-3-azabicyclo[3.1.0]hexan-6-yl}phenyl)cyclopropanesulfonamide, which was obtained in Example 8-(a), in 2.5 ml of ethyl acetate, and the resultant was stirred at room temperature for 30 minutes. After the reaction was completed, the reaction solution was concentrated under a reduced pressure. 2.0 ml of ethanol was added to the residue, and the resultant was stirred at room temperature for 3 hours stirring. The precipitated solid was collected by filtration to give 235 mg of the titled compound as a white solid. (Yield 81%, calculated as a dihydrochloride)

Mass spectrum (CI, m/z): 454[M⁺+1].

¹H-NMR spectrum (400 MHz, CD₃OD) δppm: 7.29 (1H, dd, J=8.0, 7.9 Hz), 7.25 (1H, dd, J=2.0, 1.8 Hz), 7.12 (1H, ddd, J=8.0, 2.0, 1.0 Hz), 7.12-7.06 (1H, m), 4.20-3.00 (12H, m), 2.74-2.56 (2H, m), 2.51 (1H, tt, J=7.8, 4.9 Hz), 2.42-2.32 (2H, m), 2.20-2.07 (2H, m), 1.78 (2H, q, J=7.3 Hz), 1.05-0.85 (4H, m), 0.88 (3H, t, J=7.3 Hz).

Example 9

N-(3-{(1R,5S,6r)-3-[3-(3,3-difluoropyrrolidin-1-yl)propyl]-6-ethyl-3-azabicyclo[3.1.0]hexan-6-yl}-4-fluorophenyl)cyclopropanesulfonamide

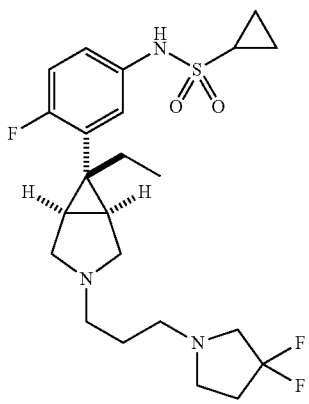

Example 9-(a)

N-(3-{(1R,5S,6r)-3-[3-(3,3-difluoropyrrolidin-1-yl)propyl]-6-ethyl-3-azabicyclo[3.1.0]hexan-6-yl}-4-fluorophenyl)cyclopropanesulfonamide (free form)

290 μl (2.1 mmol) of triethylamine was added to a solution of 185 mg (0.760 mmol) of 3-(3,3-difluoropyrrolidin-1-yl)propyl methanesulfonate, which was obtained in a similar method to that of Reference Example 8-(b), and 250 mg (0.693 mmol) of N-{3-[(1R,5S,6r)-6-ethyl-3-azabicyclo[3.1.0]hexan-6-yl]-4-fluorophenyl}cyclopropane sulfonamide hydrochloride, which was obtained in a similar method to that of Reference Example 3-(d), in 3.0 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 270 mg of the titled compound as a colorless oil. (Yield 83%)

¹H-NMR spectrum (400 MHz, CDCl₃) δppm: 7.15 (1H, dd, J=6.3, 2.8 Hz), 7.07 (1H, ddd, J=8.9, 4.3, 2.8 Hz), 6.96 (1H, dd, J=9.2, 8.9 Hz), 6.17 (0.6H, br s), 3.04 (2H, d, J=9.5 Hz), 2.88 (2H, t, J=13.4 Hz), 2.81-2.71 (2H, m), 2.72 (2H, t, J=7.1 Hz), 2.53-2.45 (4H, m), 2.41 (1H, tt, J=8.0, 4.8 Hz), 2.27 (2H, tt, J=14.6, 7.1 Hz), 1.93 (2H, q, J=7.4 Hz), 1.78-1.71 (2H, m), 1.68-1.57 (2H, m), 1.15-1.09 (2H, m), 0.99-0.91 (2H, m), 0.81 (3H, t, J=7.4 Hz).

Example 9-(b)

N-(3-{(1R,5S,6r)-3-[3-(3,3-difluoropyrrolidin-1-yl)propyl]-6-ethyl-3-azabicyclo[3.1.0]hexan-6-yl}-4-fluorophenyl)cyclopropanesulfonamide hydrochloride 513 μl (2.05 mmol) of a 4 N hydrogen chloride/ethyl acetate solution was added to a solution of 330 mg (0.700 mmol) of N-(3-{(1R,5S,6r)-3-[3-(3,3-difluoropyrrolidin-1-yl)propyl]-6-ethyl-3-azabicyclo[3.1.0]hexan-6-yl}-4-fluorophenyl)cyclopropanesulfonamide, which was obtained in Example 9-(a), in 2.0 ml of ethyl acetate, and the resultant was stirred at room temperature for 10 minutes. After the reaction was completed, the reaction solution was then concentrated under a reduced pressure. 2.0 ml of ethanol was added to the residue, and the resultant was concentrated under a reduced pressure. 2.0 ml of diethyl ether was added to the residue, and the precipitated solid was collected by filtration to give 268 mg of the titled compound as a white foam substance. (Yield 70%, calculated as a dihydrochloride)

Mass spectrum (TOF, m/z): 472[M⁺+1].

¹H-NMR spectrum (400 MHz, CD₃OD) δppm: 7.23 (1H, dd, J=6.4, 2.7 Hz), 7.19 (1H, ddd, J=9.3, 4.4, 2.7 Hz), 7.07 (1H, dd, J=9.3, 8.8 Hz), 4.30-3.50 (6I-1, m), 3.41-3.30 (6H, m), 2.68 (2H, tt, J=7.1, 13.9 Hz), 2.49 (1H, tt, J=7.7, 5.0 Hz), 2.42-2.31 (2H, m), 2.25-2.11 (2H, m), 1.77 (2H, q, J=7.3 Hz), 1.01-0.91 (4H, m), 0.91 (3H, t, J=7.3 Hz).

Example 10

N-(3-{(1R,5S,6r)-6-ethyl-3-[(2-hydroxy-2,3-dihydro-1H-inden-2-yl)methyl]-3-azabicyclo[3.1.0]hexan-6-yl}-5-fluorophenyl)cyclopropanesulfonamide

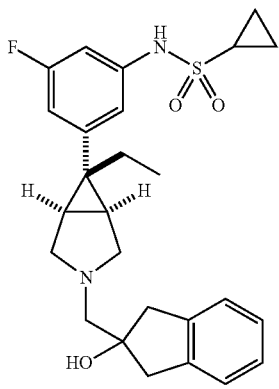

Example 10-(a)

N-(3-{(1R,5S,6r)-6-ethyl-3-[(2-hydroxy-2,3-dihydro-1H-inden-2-yl)methyl]-3-azabicyclo[3.1.0]hexan-6-yl}-5-fluorophenyl)cyclopropanesulfonamide (free form)

83 μl (0.82 mmol) of cyclopropanesulfonyl chloride was added to a solution of 230 mg (0.628 mmol) of 3-{(1R,5S,6r)-6-ethyl-3-[(2-hydroxy-2,3-dihydro-1H-inden-2-yl)methyl]-3-azabicyclo[3.1.0]hexan-6-yl}-5-fluoroaniline, which was obtained in a similar method to that of Reference Example 9-(e), in 3.1 ml of pyridine, under stirring at room temperature, and the resultant was stirred in a microwave reaction apparatus at 80° C. for 0.5 hour under heating. After the reaction was completed, a saturated aqueous ammonium chloride solution was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=40:60→10:90 (V/V)), the fraction containing the objective product was concentrated under a reduced pressure, the obtained residue was further subjected to silica gel column chromatography (DNH type (manufactured by Fuji Silycia Chemical Ltd.), elution solvent; methylene chloride:methanol=100:0→90:10 (V/V)), and the fraction containing the objective product was concentrated under a reduced pressure to give 140 mg of the titled compound as a slight yellow oil.

(Yield 47%)

Mass spectrum (CI, m/z): 471[M$^+$+1].

$^1$H-NMR spectrum (400 MHz, CD$_2$Cl$_2$) δppm: 7.23-7.17 (2H, m), 7.16-7.11 (2H, m), 6.91 (1H, dd, J=1.7, 1.7 Hz), 6.88-6.80 (2H, m), 6.43 (0.7H, br s), 3.25 (2H, d, J=9.7 Hz), 3.10-3.03 (2H, m), 3.00 (2H, d, J=16.1 Hz), 2.91 (2H, d, J=16.1 Hz), 2.81 (2H, s), 2.49 (1H, tt, J=8.0, 4.8 Hz), 1.94 (2H, q, J=7.4 Hz), 1.87-1.82 (2H, m), 1.17-1.11 (2H, m), 1.02-0.95 (2H, m), 0.87 (3H, t, J=7.4 Hz).

Example 10-(b)

N-(3-{(1R,5S,6r)-6-ethyl-3-[(2-hydroxy-2,3-dihydro-1H-inden-2-yl)methyl]-3-azabicyclo[3.1.0]hexan-6-yl}-5-fluorophenyl)cyclopropanesulfonamide hydrochloride 100 μl (0.400 mmol) of a 4 N hydrogen chloride/1,4-dioxane solution was added to a solution of 140 mg (0.297 mmol) of N-(3-{(1R,5S,6r)-6-ethyl-3-[(2-hydroxy-2,3-dihydro-1H-inden-2-yl)methyl]-3-azabicyclo[3.1.0]hexan-6-yl}-5-fluorophenyl)cyclopropanesulfonamide, which was obtained in a similar method to that of Example 10-(a), in 1.5 ml of 1,4-dioxane, under stirring at room temperature, and the resultant was stirred for 1 hour. The precipitated solid was collected by filtration, washed with 1,4-dioxane and dried to give 130 mg of the titled compound as a white solid. (Yield 86%, calculated as a monohydrochloride)

Mass spectrum (CI, m/z): 471[M$^+$+1].

$^1$H-NMR spectrum (400 MHz, CD$_3$OD) δppm: 7.27-7.21 (2H, m), 7.20-7.15 (2H, m), 7.05 (1H, dd, J=1.9, 1.6 Hz), 6.90 (1H, ddd, J=10.2, 2.1, 1.9 Hz), 6.87-6.82 (1H, m), 4.64-3.96 (2H, m), 3.62-3.42 (2H, m), 3.20 (2H, d, J=16.1 Hz), 3.20-3.09 (2H, m), 3.06 (2H, d, J=16.1 Hz), 2.58 (1H, tt, J=7.9, 4.9 Hz), 2.42-2.25 (2H, m), 1.84 (2H, q, J=7.4 Hz), 1.08-1.02 (2H, m), 1.02-0.94 (2H, m), 0.90 (3H, t, J=7.4 Hz).

Example 11

N-(3-{(1R,5S,6r)-6-ethyl-3-[(2-methoxy-2,3-dihydro-1H-inden-2-yl)methyl]-3-azabicyclo[3.1.0]hexan-6-yl}-4-fluorophenyl)cyclopropanesulfonamide

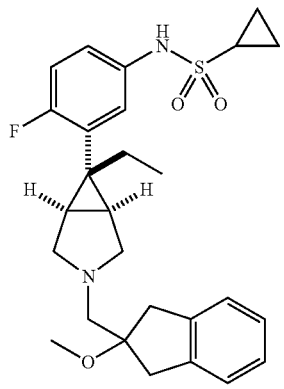

Example 11-(a)

N-(3-{(1R,5S,6r)-6-ethyl-3-[(2-methoxy-2,3-dihydro-1H-inden-2-yl)methyl]-3-azabicyclo[3.1.0]hexan-6-yl}-4-fluorophenyl)cyclopropanesulfonamide (free form)

Under an argon airflow, under stirring, 303 mg (0.840 mmol) of N-{3-[(1R,5S,6r)-6-ethyl-3-azabicyclo[3.1.0]hexan-6-yl]-4-fluorophenyl}cyclopropane sulfonamide hydrochloride, which was obtained in a similar method to that of Reference Example 3-(d), 174 μl (1.25 mmol) of triethylamine and 422 mg (1.99 mmol) of sodium triacetoxyborohydride were added to a solution of 163 mg (0.925 mmol) of 2-methoxy-2,3-dihydro-1H-inden-2-carboaldehyde, which was obtained in a similar method to that of Reference Example 4-(b), in 4 ml of 1,2-dichloroethane, and the resultant was stirred at room temperature for 4 hours. After the reaction was completed, methanol and 1 N hydrochloric acid were added to the reaction solution, and the resultant was stirred at room temperature for 40 minutes. The resultant was extracted three times with ethyl acetate, and the organic layer was washed twice with water, washed with a saturated aqueous sodium chloride solution, dried over anhydrous sodium sulfate and concentrated under a reduced pressure. The residue was subjected to silica gel column chromatography (elution solvent; hexane:ethyl acetate=50:50→0:100 (V/V)), and the fraction containing the objective product was concentrated under a reduced pressure. The obtained residue was further subjected to silica gel column chromatography (DNH type (manufactured by Fuji Silycia Chemical Ltd.) elution solvent; hexane:ethyl acetate=70:30→20:80 (V/V)), and the fraction containing the objective product was concentrated under a reduced pressure. The obtained residue was further subjected to silica gel column chromatography (elution solvent; hexane:ethyl acetate=80:20→30:70 (V/V)), and the fraction containing the objective product was concentrated under a reduced pressure to give 225 mg of the titled compound as a colorless oil. (Yield 55%)

Mass spectrum (CI, m/z): 485[M$^+$+1].

$^1$H-NMR spectrum (400 MHz, CD$_2$Cl$_2$) δppm: 7.20-7.05 (6H, m), 6.97 (1H, dd, J=9.7, 8.8 Hz), 6.25 (1H, br s), 3.25 (2H, d, J=9.5 Hz), 3.20 (3H, s), 3.07 (2H, d, J=16.5 Hz), 2.97 (2H, d, J=16.5 Hz), 2.94-2.86 (2H, m), 2.72 (2H, s), 2.40 (1H, tt, J=8.0, 4.9 Hz), 1.97 (2H, q, J=7.8 Hz), 1.75-1.69 (2H, m), 1.08-1.02 (2H, m), 0.97-0.90 (2H, m), 0.86-0.80 (3H, m).

Example 11-(b)

N-(3-{(1R,5S,6r)-6-ethyl-3-[(2-methoxy-2,3-dihydro-1H-inden-2-yl)methyl]-3-azabicyclo[3.1.0]hexan-6-yl}-4-fluorophenyl)cyclopropanesulfonamide hydrochloride Under an argon airflow, 130 μl (0.520 mmol) of a 4 N hydrogen chloride/ethyl acetate solution was added to a solution of 196 mg (0.404 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}-4-fluorophenyl)cyclopropanesulfonamide, which was obtained in Example 11-(a), in 2 ml of methylene chloride, under stirring, and the resultant was stirred at room temperature for 1 hour and concentrated under a reduced pressure. Methylene chloride and diisopropyl ether were added in small amounts to form a homogeneous solution, and the solution was stirred at room temperature for 15 hours. 3 ml of diisopropyl ether was added, and the resultant was stirred at room temperature for 1 hour. The precipitated solid was collected by filtration, washed with a small amount of a mixed solvent of methylene chloride and diisopropyl ether, and dried under a reduced pressure to give 205 mg of the titled compound as a white solid. (Yield 97%, calculated as a monohydrochloride)

Mass spectrum (CI, m/z): 485[M$^+$+1].

$^1$H-NMR spectrum (400 MHz, CD$_3$OD) δppm: 7.30-7.22 (3H, m), 7.22-7.14 (3H, m), 7.07 (1H, dd, J=9.3, 9.3 Hz), 4.48-3.93 (2H, m), 3.77-3.51 (2H, m), 3.35-3.10 (9H, m), 2.49 (1H, tt, J=7.7, 5.0 Hz), 2.42-2.26 (2H, m), 1.82 (2H, q, J=7.3 Hz), 1.02-0.85 (4H, m), 0.90 (3H, t, J=7.3 Hz).

Example 12

N-(3-{(1R,5S,6r)-6-ethyl-3-[(2-methoxy-2,3-dihydro-1H-inden-2-yl)methyl]-3-azabicyclo[3.1.0]hexan-6-yl}-5-fluorophenyl)cyclopropanesulfonamide

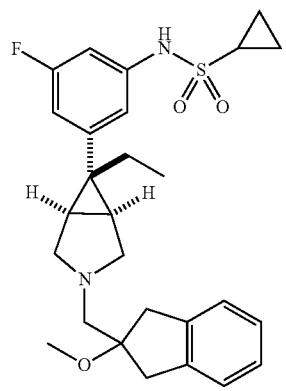 [SMILES: CC[C@]1(c2cc(F)cc(NS(=O)(=O)C3CC3)c2)[C@@H]2CN(CC3(OC)Cc4ccccc4C3)C[C@@H]21]

Example 12-(a)

N-(3-{(1R,5S,6r)-6-ethyl-3-[(2-methoxy-2,3-dihydro-1H-inden-2-yl)methyl]-3-azabicyclo[3.1.0]hexan-6-yl}-5-fluorophenyl)cyclopropanesulfonamide (free form)

0.112 ml (1.10 mmol) of cyclopropanesulfonyl chloride was added to a solution of 140 mg (0.368 mmol) of 3-{(1R,5S,6r)-6-ethyl-3-[(2-methoxy-2,3-dihydro-1H-inden-2-yl)methyl]-3-azabicyclo[3.1.0]hexan-6-yl}-5-fluoroaniline, which was obtained in Reference Example 10-(a), in 1.5 ml of pyridine, at room temperature, and the resultant was stirred in a microwave reaction apparatus at 80° C. for 0.5 hour. After the reaction was completed, toluene was added to the reaction solution, and the resultant was concentrated under a reduced pressure. Ethyl acetate and a saturated sodium hydrogen carbonate solution were added to the residue, and the resultant was extracted with ethyl acetate. The organic layer was dried over anhydrous sodium sulfate, and then concentrated under a reduced pressure. The residue was subjected to silica gel column chromatography (elution solvent; hexane:ethyl acetate=75:25→67:33 (V/V)), the fraction containing the objective product was concentrated under a reduced pressure, the residue was further subjected to silica gel column chromatography (elution solvent; hexane:ethyl acetate=75:25→67:33 (V/V)), and the fraction containing the objective product was concentrated under a reduced pressure to give 105 mg of the titled compound as a brown oil. (Yield 59%)

$^1$H-NMR spectrum (400 MHz, CDCl$_3$) δppm: 7.21-7.11 (4H, m), 6.87 (1H, dd, J=2.0, 1.9 Hz), 6.83 (1H, ddd, J=9.5, 1.9, 1.8 Hz), 6.78 (1H, ddd, J=9.7, 2.0, 1.8 Hz), 6.28 (1H, br s), 3.23 (3H, s), 3.17 (2H, d, J=9.5 Hz), 3.11 (2H, d, J=16.5 Hz), 2.99 (2H, d, J=16.5 Hz), 2.96-2.89 (2H, m), 2.72 (2H, s), 2.48 (1H, tt, J=8.0, 4.8 Hz), 1.96 (2H, q, J=7.4 Hz), 1.75-1.68 (2H, m), 1.23-1.16 (2H, m), 1.02-0.95 (2H, m), 0.83 (3H, t, J 7.4 Hz).

Example 12-(b)

N-(3-{(1R,5S,6r)-6-ethyl-3-[(2-methoxy-2,3-di-hydro-1H-inden-2-yl)methyl]-3-azabicyclo[3.1.0]hexan-6-yl}-5-fluorophenyl)cyclopropanesulfonamide hydrochloride Under an argon airflow, 63 μl (0.25 mmol) of a 4 N hydrogen chloride/1,4-dioxane solution was added to a solution of 78 mg (0.16 mmol) of N-(3-{(1R,5S,6r)-6-ethyl-3-[(2-methoxy-2,3-dihydro-1H-inden-2-yl)methyl]-3-azabicyclo[3.1.0]hexan-6-yl}-5-fluorophenyl)cyclopropanesulfonamide, which was obtained in a similar method to that of Example 12-(a), in 1 ml of 1,4-dioxane, under stirring. The reaction solution was concentrated under a reduced pressure, a mixed solvent of 1 ml of ethanol and 1 ml of diethyl ether was then added thereto, and an ultrasonic treatment was performed. The resultant was stirred for 30 minutes under ice cooling, and the precipitated solid was collected by filtration, washed with diethyl ether and dried at 50° C. under a reduced pressure to give 55 mg of the titled compound as a white solid.
(Yield 66%, calculated as a monohydrochloride)
Mass spectrum (APCI, m/z): 485[M$^+$+1].
$^1$H-NMR spectrum (400 MHz, CD$_3$OD) δppm: 7.30-7.16 (4H, m), 7.05 (1H, dd, J=1.9, 1.6 Hz), 6.90 (1H, ddd, J=10.2, 2.2, 1.9 Hz), 6.87-6.82 (1H, m), 4.41-3.91 (2H, m), 3.75-3.49 (2H, m), 3.28-3.06 (6H, m), 3.14 (3H, s), 2.58 (1H, tt, J=7.9, 4.9 Hz), 2.43-2.24 (2H, m), 1.84 (2H, q, J=7.3 Hz), 1.09-0.94 (4H, m), 0.89 (3H, t, J=7.3 Hz).

Example 13

N-(3-{(1R,5S,6r)-3-[(2-ethoxy-2,3-dihydro-1H-inden-2-yl)methyl]-6-ethyl-3-azabicyclo[3.1.0]hexan-6-yl}phenyl)cyclopropanesulfonamide

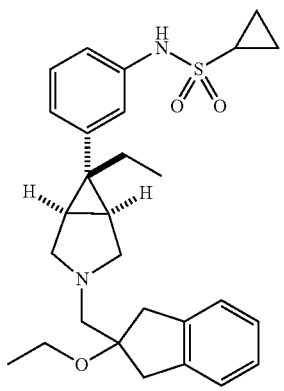 [SMILES: CCOC1(CN2C[C@@H]3[C@H](C2)[C@@]3(CC)c2cccc(NS(=O)(=O)C3CC3)c2)Cc2ccccc2C1]

Example 13-(a)

N-(3-{(1R,5S,6r)-3-[(2-ethoxy-2,3-dihydro-1H-inden-2-yl)methyl]-6-ethyl-3-azabicyclo[3.1.0]hexan-6-yl}phenyl)cyclopropanesulfonamide (free form)

196 mg (0.572 mmol) of N-{3-[(1R,5S,6r)-6-ethyl-3-azabicyclo[3.1.0]hexan-6-yl]phenyl}cyclopropanesulfonamide hydrochloride, which was obtained in Reference Example 1-(d), and 228 μl (1.64 mmol) of triethylamine were added to a solution of 156 mg (0.820 mmol) of 2-ethoxy-2,3-dihydro-1H-indene-2-carboaldehyde, which was obtained in a similar method to that of Reference Example 11-(b), in 0.5 ml of methylene chloride, and the resultant was stirred at room temperature for 10 minutes. 203 mg (0.958 mmol) of sodium triacetoxyborohydride was then added, and the resultant was stirred at room temperature for 2 hours. After the reaction was completed, ethyl acetate and an aqueous sodium hydrogen carbonate solution were added to the reaction solution, and the resultant was extracted with ethyl acetate. The organic layer was dried over anhydrous magnesium sulfate and concentrated under a reduced pressure. The residue was subjected to silica gel column chromatography (elution solvent; hexane:ethyl acetate=87:13→67:33 (V/V)), and the fraction containing the objective product was concentrated under a reduced pressure to give 230 mg of the titled compound as a colorless oil. (Yield 84%)
$^1$H-NMR spectrum (400 MHz, CDCl$_3$) δppm: 7.23 (1H, dd, J=7.9, 7.8 Hz), 7.19-7.07 (6H, m), 7.04 (1H, ddd, J=7.9, 2.3, 1.0 Hz), 6.22 (1H, br s), 3.41 (2H, q, J=7.0 Hz), 3.18 (2H, d, J=9.5 Hz), 3.10 (2H, d, J=16.5 Hz), 3.01 (2H, d, J=16.5 Hz), 2.97-2.89 (2H, m), 2.71 (2H, s), 2.45 (1H, tt, J=8.0, 4.8 Hz), 1.96 (2H, q, J=7.4 Hz), 1.76-1.68 (2H, m), 1.19-1.13 (2H, m), 1.16 (3H, t, J=7.0 Hz), 0.98-0.91 (2H, m), 0.82 (3H, t, J=7.4 Hz).

Example 13-(b)

N-(3-{(1R,5S,6r)-3-[(2-ethoxy-2,3-dihydro-1H-inden-2-yl)methyl]-6-ethyl-3-azabicyclo[3.1.0]hexan-6-yl}phenyl)cyclopropanesulfonamide hydrochloride 123 μl (0.492 mmol) of a 4 N hydrogen chloride/1,4-dioxane solution was added to a solution of 185 mg (0.385 mmol) of N-(3-{(1R,5S,6r)-3-[(2-ethoxy-2,3-dihydro-1H-inden-2-yl)methyl]-6-ethyl-3-azabicyclo[3.1.0]hexan-6-yl}phenyl)cyclopropanesulfonamide, which was obtained in a similar method to that of Example 13-(a), in 1 ml of 1,4-dioxane, under stirring. The reaction solution was concentrated under a reduced pressure, ethanol was added thereto, and the precipitated solid was collected by filtration to give 190 mg of a white solid.
171 mg of the obtained white solid was recrystallized from a mixed solvent of ethanol/water, and the obtained solid was collected by filtration to give 102 mg of the titled compound as a white solid. (Yield 57%, calculated as a monohydrochloride)
Mass spectrum (APCI, m/z): 481[M$^+$+1].
$^1$H-NMR spectrum (400 MHz, CD$_3$OD) δppm: 7.29 (1H, dd, J=7.8, 7.8 Hz), 7.27-7.16 (5H, m), 7.15-7.07 (2H, m), 4.31-3.99 (2H, m), 3.68-3.54 (2H, m), 3.34-3.26 (2H, m), 3.27 (2H, d, J=17.1 Hz), 3.22-3.08 (2H, m), 3.15 (2H, d, J=17.1 Hz), 2.52 (1H, tt, J=7.9, 4.9 Hz), 2.41-2.24 (2H, m), 1.84 (2H, q, J=7.3 Hz), 1.14 (3H, t, J=6.9 Hz), 1.04-0.91 (4H, m), 0.88 (3H, t, J=7.3 Hz).

Example 14

N-(3-{(1R,5S,6r)-3-[3-(1-ethoxy-4,4-difluorocyclohexyl)propyl]-6-ethyl-3-azabicyclo[3.1.0]hexan-6-yl}phenyl)cyclopropanesulfonamide

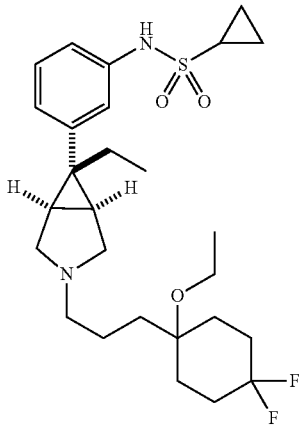 [SMILES: CCOC1(CCCN2C[C@@H]3[C@H](C2)[C@@]3(CC)c2cccc(NS(=O)(=O)C3CC3)c2)CCC(F)(F)CC1]

Example 14-(a)

N-(3-{(1R,5S,6r)-3-[3-(1-ethoxy-4,4-difluorocyclohexyl)propyl]-6-ethyl-3-azabicyclo[3.1.0]hexan-6-yl}phenyl)cyclopropanesulfonamide (free form)

Under an argon airflow, 101 μl (0.727 mmol) of trimethylamine was added to a solution of 177 mg (0.804 mmol) of 3-(4,4-difluoro-1-ethoxycyclohexyl)propanal, which was obtained in a similar method to that of Reference Example 12-(c), and 250 mg (0.729 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), in 10 ml of methylene chloride, under stirring, and the resultant was stirred at room temperature for 15 minutes. 386 mg (1.82 mmol) of sodium triacetoxyborohydride was then added, and the resultant was stirred at room temperature for 3 hours. After the reaction was completed, water was added to the reaction solution, and the resultant was extracted with ethyl acetate. The organic layer was washed with a saturated aqueous sodium chloride solution, then dried over anhydrous magnesium sulfate, and concentrated under a reduced pressure. The residue was subjected to silica gel column chromatography (DNH type (manufactured by Fuji Silycia Chemical Ltd.), elution solvent; hexane:ethyl acetate), and the fraction containing the objective product was concentrated under a reduced pressure to give 309 mg of the titled compound as a colorless oil. (Yield 83%)

Mass spectrum (DUIS, m/z): 511[M$^+$+1].

$^1$H-NMR spectrum (400 MHz, CDCl$_3$) δppm: 7.23 (1H, dd, J=7.9, 7.8 Hz), 7.17-7.14 (1H, m), 7.09 (1H, ddd, J=7.8, 1.3, 1.1 Hz), 7.04 (1H, ddd, J=7.9, 2.2, 1.1 Hz), 6.24 (0.8H, br s), 3.31 (2H, q, J=7.0 Hz), 2.99 (2H, d, J=9.7 Hz), 2.82-2.72 (2H, m), 2.49-2.40 (3H, m), 2.04-1.82 (6H, m), 1.96 (2H, q, J=7.4 Hz), 1.82-1.71 (2H, m), 1.54-1.39 (6H, m), 1.20 (3H, t, J=7.0 Hz), 1.19-1.12 (2H, m), 0.99-0.90 (2H, m), 0.81 (3H, t, J=7.4 Hz).

Example 14-(b)

N-(3-{(1R,5S,6r)-3-[3-(1-ethoxy-4,4-difluorocyclohexyl)propyl]-6-ethyl-3-azabicyclo[3.1.0]hexan-6-yl}phenyl)cyclopropanesulfonamide hydrochloride 0.30 ml (1.20 mmol) of a 4 N hydrogen chloride/ethyl acetate solution was added to a solution of 302 mg (0.591 mmol) of N-(3-{(1R,5S,6r)-3-[3-(1-ethoxy-4,4-difluorocyclohexyl)propyl]-6-ethyl-3-azabicyclo[3.1.0]hexan-6-yl}phenyl)cyclopropanesulfonamide, which was obtained in Example 14-(a), in 4 ml of ethyl acetate, at room temperature. The reaction solution was concentrated under a reduced pressure, and dried at 50° C. under a reduced pressure to give 260 mg of the titled compound as a foam substance. (Yield 80%, calculated as a monohydrochloride)

Mass spectrum (CI, m/z): 511[M$^+$+1].

$^1$H-NMR spectrum (400 MHz, CD$_3$OD) δppm: 7.28 (1H, dd, J=8.0, 8.0 Hz), 7.24 (1H, dd, J=2.0, 1.9 Hz), 7.12 (1H, ddd, J=8.0, 2.0, 1.0 Hz), 7.10-7.07 (1H, m), 4.08-3.78 (2H, m), 3.37 (2H, q, J=7.0 Hz), 3.27-2.84 (4H, m), 2.51 (1H, tt, J=7.9, 4.9 Hz), 2.38-2.28 (2H, m), 2.11-1.61 (10H, m), 1.59-1.46 (4H, m), 1.20 (3H, t, J=7.0 Hz), 1.03-0.90 (4H, m), 0.88 (3H, t, J=7.0 Hz).

Example 15

N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide

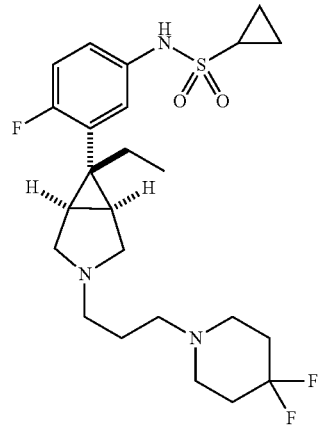 [SMILES: CC[C@]1(c2cc(NS(=O)(=O)C3CC3)ccc2F)[C@@H]2CN(CCCN3CCC(F)(F)CC3)C[C@@H]21]

Example 15-(a)

N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide (free form)

Under a nitrogen airflow, 204 mg (0.565 mmol) of N-{3-[(1R,5S,6r)-6-ethyl-3-azabicyclo[3.1.0]hexan-6-yl]-4-fluorophenyl}cyclopropane sulfonamide hydrochloride, which was obtained in Reference Example 3-(d), and 150 μl (1.08 mmol) of triethylamine were added to a solution of 139 mg (0.574 mmol) of 1-(3-bromopropyl)-4,4-difluoropiperidine, which was obtained in a similar method to that of Reference Example 7-(a), in 2 ml of ethanol, and the resultant was stirred in a microwave reaction apparatus at 120° C. for 1.5 hours. After the reaction was completed, ethyl acetate and water were added to the reaction solution, and the resultant was extracted twice with ethyl acetate. The organic layer was dried over anhydrous magnesium sulfate and concentrated under a reduced pressure. The residue was subjected to silica gel column chromatography (Diol type (manufactured by Fuji Silycia Chemical Ltd.), elution solvent; hexane:ethyl acetate=70:30→30:70 (V/V)), and the fraction containing the objective product was concentrated under a reduced pressure to give 244 mg of the titled compound as a colorless oil. (Yield 89%)

$^1$H-NMR spectrum (400 MHz, CDCl$_3$) δppm: 7.16 (1H, dd, J=6.3, 2.8 Hz), 7.07 (1H, ddd, J=8.9, 4.3, 2.8 Hz), 6.96 (1H, dd, J=9.2, 8.9 Hz), 6.10 (0.6H, br s), 3.04 (2H, d, J=9.5 Hz), 2.83-2.70 (2H, m), 2.61-2.36 (9H, m), 2.06-1.94 (4H, m), 1.93 (2H, q, J=7.4 Hz), 1.78-1.70 (2H, m), 1.70-1.55 (2H, m), 1.16-1.08 (2H, m), 0.98-0.91 (2H, m), 0.81 (3H, t, J=7.4 Hz).

Example 15-(b)

N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide hydrochloride Under a nitrogen airflow, 0.50 ml (2.0 mmol) of a 4 N hydrogen chloride/ethyl acetate solution was added to a solution of 241 mg (0.496 mmol) of N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide, which was obtained in Example 15-(a), under stirring at room temperature, and the resultant was stirred for 20 minutes. The reaction solution was concentrated under a reduced pressure, ethanol was added to the residue, and the resultant was concentrated under a reduced pressure. Ethyl acetate was added thereto, an ultrasonic treatment was performed, and the generated solid was collected by filtration to give 240 mg of the titled compound as a white solid. (Yield 87%, calculated as a dihydrochloride)

Mass spectrum (TOF, m/z): 486[M$^+$+1].

$^1$H-NMR spectrum (400 MHz, CD$_3$OD) δppm: 7.23 (1H, dd, J=6.4, 2.7 Hz), 7.18 (1H, ddd, J=8.8, 4.4, 2.7 Hz), 7.07 (1H, dd, J=9.9, 8.8 Hz), 4.29-3.44 (4H, m), 3.48-2.88 (8H, m), 2.56-2.11 (8H, m), 2.49 (1H, U, J=7.7, 5.0 Hz), 1.85-1.68 (2H, m), 1.03-0.87 (7H, m).

Example 16

N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide

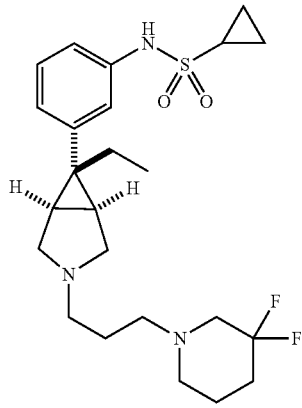 [SMILES: CC[C@]1(c2cccc(NS(=O)(=O)C3CC3)c2)[C@@H]2CN(CCCN3CCCC(F)(F)C3)C[C@@H]21]

Example 16-(a)

N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide (free form)

244 μl (1.75 mmol) of triethylamine was added to a solution of 150 mg (0.583 mmol) of 3-(3,3-difluoropiperidin-1-yl)propyl methanesulfonate, which was obtained in a similar method to that of Reference Example 13-(a), and 211 mg (0.615 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), in 3 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, then dried over anhydrous magnesium sulfate and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 238 mg of the titled compound as a white solid. (Yield 87%)

Mass spectrum (DUIS, m/z): 468[M$^+$+1].

$^1$H-NMR spectrum (400 MHz, CDCl$_3$) δppm: 7.23 (1H, dd, J=7.8, 7.7 Hz), 7.15 (1H, dd, J=2.0, 1.6 Hz), 7.09 (1H, ddd, J=7.7, 1.6, 1.2 Hz), 7.04 (1H, ddd, J=7.8, 2.0, 1.2 Hz), 6.20 (0.8H, br s), 3.00 (2H, d, J=9.5 Hz), 2.80-2.73 (2H, m), 2.63 (2H, t, J=11.4 Hz), 2.53-2.39 (7H, m), 1.95 (2H, q, J=7.4 Hz), 1.92-1.73 (6H, m), 1.70-1.60 (2H, m), 1.19-1.12 (2H, m), 0.99-0.90 (2H, m), 0.81 (3H, t, J=7.4 Hz).

Example 16-(b)

N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide hydrochloride 0.3 ml (1.2 mmol) of a 4 N hydrogen chloride/ethyl acetate solution was added at room temperature to a solution of 180 mg (0.385 mmol) of N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide, which was obtained in a similar method to that of Example 16-(a), in 0.771 ml of ethyl acetate, under stirring. The reaction solution was concentrated under a reduced pressure, ethyl acetate was added to the residue, and the resultant was heated at 40° C. for 1 hour under stirring. The generated solid was collected by filtration to give 175 mg of the titled compound as a white solid.

(Yield 84%, calculated as a dihydrochloride)

Mass spectrum (CI, m/z): 468[M$^+$+1].

$^1$H-NMR spectrum (400 MHz, CD$_3$OD) δppm: 7.29 (1H, dd, J=7.9, 7.8 Hz), 7.25 (1H, dd, J=2.0, 1.7 Hz), 7.12 (1H, ddd, J=7.9, 2.0, 1.1 Hz), 7.09 (1H, ddd, J=7.8, 1.7, 1.1 Hz), 4.23-2.92 (12H, m), 2.51 (1H, tt, J=7.8, 4.9 Hz), 2.33-2.41

(2H, m), 2.02-2.28 (6H, m), 1.79 (2H, q, J=7.3 Hz), 0.91-1.03 (4H, m), 0.89 (3H, t, J=7.3 Hz).

Example 17

N-(3-{(1R,5S,6r)-3-[(2-hydroxy-2,3-dihydro-1H-inden-2-yl)methyl]-6-methyl-3-azabicyclo[3.1.0]hexan-6-yl}phenyl)cyclopropanesulfonamide

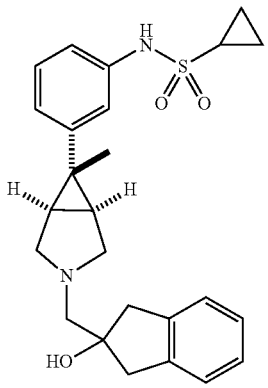 [SMILES: C[C@]1(c2cccc(NS(=O)(=O)C3CC3)c2)[C@@H]2CN(CC3(O)Cc4ccccc4C3)C[C@@H]21]

Example 17-(a)

N-(3-{(1R,5S,6r)-3-[(2-hydroxy-2,3-dihydro-1H-inden-2-yl)methyl]-6-methyl-3-azabicyclo[3.1.0]hexan-6-yl}phenyl)cyclopropanesulfonamide (free form)

259 µl (1.86 mmol) of triethylamine was added to a solution of 244 mg (0.742 mmol) of N-{3-[(1R,5S,6r)-6-methyl-3-azabicyclo[3.1.0]hexan-6-yl]phenyl}cyclopropanesulfonamide hydrochloride, which was obtained in a similar method to that of Reference Example 14-(e), and 180 mg (0.743 mmol) of (2-hydroxy-2,3-dihydro-1H-inden-2-yl)methyl methanesulfonate, which was obtained in a similar method to that of Reference Example 2-(b), in 4 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, then dried over anhydrous magnesium sulfate and concentrated under a reduced pressure. The residue was subjected to silica gel column chromatography (elution solvent; hexane:ethyl acetate=57:43→0:100 (V/V)), and the fraction containing the objective product was concentrated under a reduced pressure to give 261 mg of the titled compound as a white solid. (Yield 80%)

Mass spectrum (DUIS, m/z): 439 [M$^+$+1].

$^1$H-NMR spectrum (400 MHz, CDCl$_3$) δppm: 7.24 (1H, dd, J=7.8, 7.7 Hz), 7.22-7.12 (5H, m), 7.11-7.07 (1H, m), 7.03 (1H, ddd, J=7.8, 2.2, 0.9 Hz), 6.22 (0.9H, br s), 3.22 (2H, d, J=9.7 Hz), 3.14-3.07 (2H, m), 3.02 (2H, d, J=16.5 Hz), 2.97 (2H, d, J=16.5 Hz), 2.83 (2H, s), 2.47 (1H, tt, J=8.0, 4.8 Hz), 1.86-1.81 (2H, m), 1.49 (3H, s), 1.21-1.14 (2H, m), 1.04-0.90 (2H, m).

Example 17-(b)

N-(3-{(1R,5S,6r)-3-[(2-hydroxy-2,3-dihydro-1H-inden-2-yl)methyl]-6-methyl-3-azabicyclo[3.1.0]hexan-6-yl}phenyl)cyclopropanesulfonamide hydrochloride 213 µl (0.852 mmol) of a 4 N hydrogen chloride/1,4-dioxane solution was added to a solution of 257 mg (0.586 mmol) of N-(3-{(1R,5S,6r)-3-[(2-hydroxy-2,3-dihydro-1H-inden-2-yl)methyl]-6-methyl-3-azabicyclo[3.1.0]hexan-6-yl}phenyl)cyclopropanesulfonamide, which was obtained in a similar method to that of Example 17-(a), in 1 ml of 1,4-dioxane. The reaction solution was concentrated under a reduced pressure, ethanol was added to the residue, and the resultant was concentrated under a reduced pressure and dried under a reduced pressure. 1 ml of diethyl ether and 1 ml of ethanol were added to the obtained residue, and the resultant was subjected to an ultrasonic treatment and ice-cooled for 0.5 hour. The generated solid was collected by filtration, washed with diethyl ether and then dried at 50° C. under a reduced pressure to give 226 mg of the titled compound as a white solid.

(Yield 81%, calculated as a monohydrochloride)

Mass spectrum (APCI, m/z): 439[M$^+$+1].

$^1$H-NMR spectrum (400 MHz, CD$_3$OD) δppm: 7.30-7.15 (6H, m), 7.15-7.08 (2H, m), 4.33-4.01 (2H, m), 3.58-3.49 (2H, m), 3.26-3.15 (2H, m), 3.21 (2H, d, J=16.2 Hz), 3.07 (2H, d, J=16.2 Hz), 2.53 (1H, tt, J=7.9, 4.9 Hz), 2.43-2.24 (2H, m), 1.51 (3H, s), 1.06-0.90 (4H, m).

Example 18

N-(3-{(1R,5S,6r)-3-[(2-methoxy-2,3-dihydro-1H-inden-2-yl)methyl]-6-methyl-3-azabicyclo[3.1.0]hexan-6-yl}phenyl)cyclopropanesulfonamide

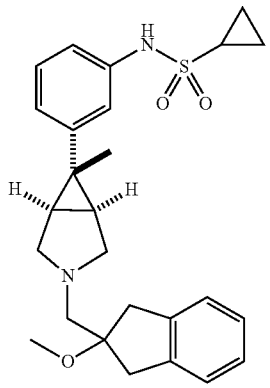 [SMILES: COC1(CN2C[C@@H]3[C@H](C2)[C@@]3(C)c2cccc(NS(=O)(=O)C3CC3)c2)Cc2ccccc2C1]

Example 18-(a)

N-(3-{(1R,5S,6r)-3-[(2-methoxy-2,3-dihydro-1H-inden-2-yl)methyl]-6-methyl-3-azabicyclo[3.1.0]hexan-6-yl}phenyl)cyclopropanesulfonamide (free form)

150 mg (0.456 mmol) of N-{3-[(1R,5S,6r)-6-methyl-3-azabicyclo[3.1.0]hexan-6-yl]phenyl}cyclopropanesulfonamide hydrochloride, which was obtained in a similar method to that of Reference Example 14-(e), and 61 μl (0.44 mmol) of triethylamine were added to a solution of 123 mg (0.698 mmol) of 2-methoxy-2,3-dihydro-1H-indene-2-carboaldehyde, which was obtained in a similar method to that of Reference Example 4-(b), in 2 ml of methylene chloride, and the resultant was stirred at room temperature for 10 minutes. 222 mg (1.05 mmol) of sodium triacetoxyborohydride was then added, and the resultant was stirred at room temperature for 3 hours. After the reaction was completed, an aqueous sodium hydrogen carbonate solution was added to the reaction solution, and the resultant was extracted three times with methylene chloride. The organic layer was dried over anhydrous magnesium sulfate and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 130 mg of the titled compound as a colorless oil. (Yield 63%)

$^1$H-NMR spectrum (400 MHz, CDCl$_3$) δppm: 7.23 (1H, dd, J=7.9, 7.8 Hz), 7.20-7.09 (5H, m), 7.09-7.04 (1H, m), 7.02 (1H, ddd, J=7.9, 2.3, 1.0 Hz), 6.23 (0.8H, br s), 3.23 (3H, s), 3.16 (2H, d, J=9.5 Hz), 3.10 (2H, d, J=16.5 Hz), 3.04-2.95 (2H, m), 2.99 (2H, d, J=16.5 Hz), 2.74 (2H, s), 2.46 (1H, tt, J=8.0, 4.8 Hz), 1.74-1.69 (2H, m), 1.51 (3H, s), 1.21-1.11 (2H, m), 1.02-0.89 (2H, m).

Example 18-(b)

N-(3-{(1R,5S,6r)-3-[(2-methoxy-2,3-dihydro-1H-inden-2-yl)methyl]-6-methyl-3-azabicyclo[3.1.0]hexan-6-yl}phenyl)cyclopropanesulfonamide hydrochloride 104 μl (0.416 mmol) of a 4 N hydrogen chloride/1,4-dioxane solution was added to a solution of 125 mg (0.276 mmol) of N-(3-{(1R,5S,6r)-3-[(2-methoxy-2,3-dihydro-1H-inden-2-yl)methyl]-6-methyl-3-azabicyclo[3.1.0]hexan-6-yl}phenyl)cyclopropanesulfonamide, which was obtained in a similar method to that of Example 18-(a), in 1 ml of 1,4-dioxane. The reaction solution was concentrated under a reduced pressure, ethanol was added to the residue, and the resultant was concentrated under a reduced pressure and dried under a reduced pressure. 1 ml of diethyl ether and 1 ml of ethanol were added to the obtained residue, and the resultant was subjected to an ultrasonic treatment and ice-cooled for 0.5 hours. The generated solid was collected by filtration, washed with diethyl ether and then dried at 50° C. under a reduced pressure to give 97 mg of the titled compound as a white solid.

(Yield 72%, calculated as a monohydrochloride)

Mass spectrum (APCI, m/z): 453[M$^+$+1].

$^1$H-NMR spectrum (400 MHz, CD$_3$OD) δppm: 7.32-7.17 (6H, m), 7.15-7.08 (2H, m), 4.66-4.00 (2H, m), 3.72-3.51 (2H, m), 3.29-3.12 (6H, m), 3.14 (3H, s), 2.53 (1H, tt, J=7.9, 4.9 Hz), 2.41-2.26 (2H, m), 1.51 (3H, s), 1.06-0.90 (4H, m).

Example 19

N-(3-{(1R,5S,6r)-3-[(2-hydroxy-2,3-dihydro-1H-inden-2-yl)methyl]-6-vinyl-3-azabicyclo[3.1.0]hexan-6-yl}phenyl)cyclopropanesulfonamide

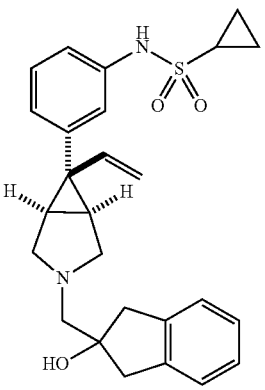 [SMILES: C=C[C@]1(c2cccc(NS(=O)(=O)C3CC3)c2)[C@@H]2CN(CC3(O)Cc4ccccc4C3)C[C@@H]21]

Example 19-(a)

N-(3-{(1R,5S,6r)-3-[(2-hydroxy-2,3-dihydro-1H-inden-2-yl)methyl]-6-vinyl-3-azabicyclo[3.1.0]hexan-6-yl}phenyl)cyclopropanesulfonamide (free form)

224 μl (1.61 mmol) of triethylamine were added to a solution of 184 mg (0.540 mmol) of N-{3-[(1R,5S,6r)-6-vinyl-3-azabicyclo[3.1.0]hexan-6-yl]phenyl}cyclopropanesulfonamide hydrochloride, which was obtained in a similar method to that of Reference Example 15-(g), and 150 mg (0.619 mmol) of (2-hydroxy-2,3-dihydro-1H-inden-2-yl)methyl methanesulfonate, which was obtained in a similar method to that of Reference Example 2-(b), in 3 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 155 mg of the titled compound as a white solid. (Yield 64%)

$^1$H-NMR spectrum (400 MHz, CDCl$_3$) δppm: 7.25 (1H, dd, J=7.9, 7.8 Hz), 7.22-7.12 (5H, m), 7.12-7.08 (1H, m), 7.06 (1H, ddd, J=7.9, 2.2, 0.9 Hz), 6.34-6.22 (1H, m), 6.28 (1H, dd, J=17.5, 10.5 Hz), 5.23 (1H, dd, J=10.5, 1.6 Hz), 4.96 (1H, dd, J=17.5, 1.6 Hz), 3.31 (2H, d, J=9.4 Hz), 3.06-2.91 (6H, m), 2.81 (2H, s), 2.46 (1H, tt, J=8.0, 4.8 Hz), 2.03-1.97 (2H, m), 1.20-1.12 (2H, m), 0.99-0.91 (2H, m).

Example 19-(b)

N-(3-{(1R,5S,6r)-3-[(2-hydroxy-2,3-dihydro-1H-inden-2-yl)methyl]-6-vinyl-3-azabicyclo[3.1.0]hexan-6-yl}phenyl)cyclopropanesulfonamide hydrochloride 255 μl (1.02 mmol) of a 4 N hydrogen chloride/1,4-dioxane solution was added to a solution of 153 mg (0.340 mmol) of N-(3-{(1R,5S,6r)-3-[(2-hydroxy-2,3-dihydro-1H-inden-2-yl)methyl]-6-vinyl-3-azabicyclo[3.1.0]hexan-6-yl}phenyl)cyclopropanesulfonamide, which was obtained in a similar method to that of Example 19-(a), in 2 ml of 1,4-dioxane, under stirring at room temperature. The reaction solution was concentrated under a reduced pressure, and dried under a reduced pressure. Ethanol was added to the residue, and the resultant was subjected to an ultrasonic treatment and then stirred for 2 hours under ice cooling. The precipitated solid was collected by filtration and washed with cold ethanol to give 129 mg of the titled compound as a white solid. (Yield 78%, calculated as a monohydrochloride)

Mass spectrum (APCI, m/z): 451[M$^+$+1].

$^1$H-NMR spectrum (400 MHz, CD$_3$OD) δppm: 7.37-7.06 (8H, m), 6.45-6.08 (1H, m), 5.77-5.05 (2H, m), 4.48-3.38 (6H, m), 3.20 (2H, d, J=16.3 Hz), 3.06 (2H, d, J=16.3 Hz), 2.60-2.47 (2H, m), 2.52 (1H, tt, J=7.9, 4.9 Hz), 1.07-0.88 (4H, m).

Example 20

N-(3-{(1R,5S,6r)-3-[(5,6-difluoro-2-hydroxy-2,3-dihydro-1H-inden-2-yl)methyl]-6-ethyl-3-azabicyclo[3.1.0]hexan-6-yl}phenyl)cyclopropanesulfonamide

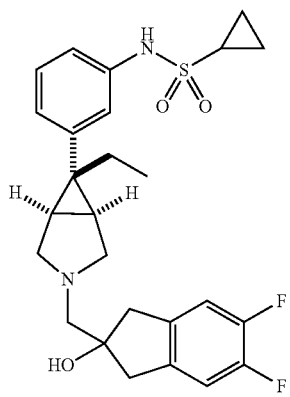 [SMILES: CC[C@]1(c2cccc(NS(=O)(=O)C3CC3)c2)[C@@H]2CN(CC3(O)Cc4cc(F)c(F)cc4C3)C[C@@H]21]

Example 20-(a)

N-(3-{(1R,5S,6r)-3-[(5,6-difluoro-2-hydroxy-2,3-dihydro-1H-inden-2-yl)methyl]-6-ethyl-3-azabicyclo[3.1.0]hexan-6-yl}phenyl)cyclopropanesulfonamide (free form)

Under an argon airflow, 35 μl (0.25 mmol) of triethylamine and 26 mg (0.093 mmol) of (5,6-difluoro-2-hydroxy-2,3-dihydro-1H-inden-2-yl)methyl methanesulfonate, which was obtained in a similar method to that of Reference Example 16-(g), were added to a suspension liquid of 42 mg (0.12 mmol) of N-{3-[(1R,5S,6r)-6-ethyl-3-azabicyclo[3.1.0]hexan-6-yl]phenyl}cyclopropanesulfonamide hydrochloride, which was obtained in a similar method to that of Reference Example 1-(d), in 1.0 ml of THF, with stirring under ice cooling, and the resultant was stirred at room temperature for 1.5 hours and then stirred under heating at 60° C. for 2 hours. The reaction solution was concentrated under a reduced pressure, 2 ml of ethanol was added to the residue, and the resultant was stirred under heating at 70° C. for 1 hour. 60 μl (0.43 mmol) of triethylamine was added to the reaction solution, and the resultant was stirred at room temperature for 15 hours. After the reaction was completed, 2 ml of water was added to the reaction solution, and the reaction solution was extracted twice with 5 ml of methylene chloride. The organic layer was washed with a saturated aqueous sodium chloride solution, dried over anhydrous sodium sulfate and concentrated under a reduced pressure. The residue was subjected to silica gel column chromatography (elution solvent; hexane:ethyl acetate=60:40→50:50 (V/V)), and the fraction containing the objective product was concentrated under a reduced pressure to give 32 mg of the titled compound as a yellow oil. (Yield 57%)

$^1$H-NMR spectrum (400 MHz, CD$_2$Cl$_2$) δppm: 7.26 (1H, dd, J=7.9, 7.8 Hz), 7.17 (1H, dd, J=2.1, 1.7 Hz), 7.12 (1H, ddd, J=7.8, 1.7, 1.0 Hz), 7.05 (1H, ddd, J=7.9, 2.1, 1.0 Hz), 7.01 (2H, dd, J=9.0, 9.0 Hz), 6.41 (0.8H, br s), 3.22 (2H, d, J=9.6 Hz), 3.12-3.03 (2H, m), 2.96 (2H, d, J=16.2 Hz), 2.87 (2H, d, J=16.2 Hz), 2.80 (2H, s), 2.45 (1H, tt, J=8.0, 4.9 Hz), 1.91 (2H, q, J=7.4 Hz), 1.94-1.83 (2H, m), 1.13-1.07 (2H, m), 0.98-0.91 (2H, m), 0.85 (3H, t, J=7.4 Hz).

Reference Example 1

Preparation of N-{3-[(1R,5S,6r)-6-ethyl-3-azabicyclo[3.1.0]hexan-6-yl]phenyl}cyclopropanesulfonamide hydrochloride Reference Example 1-(a)

(1R,5S,6r)-6-(3-bromophenyl)-6-ethyl-3-azabicyclo[3.1.0]hexane-2,4-dione 47.5 g (949 mmol) of hydrazine monohydrate was added dropwise to a solution of 50.5 g (237 mmol) of 3-bromopropiophenone in 500 ml of methanol at room temperature over 6 minutes. After the dropwise addition, the solution was stirred at 60° C. for 3 hours. After the reaction was completed, the reaction solution was cooled to room temperature, and liquid separation was performed by adding 1,000 ml of methylene chloride and 500 ml of water. After the organic layer was washed twice with 500 ml of water and dried over anhydrous sodium sulfate, 500 ml of 1,4-dioxane was added, and the resultant was concentrated under a reduced pressure at 39° C. to give about 440 g of a yellow solution. Under a nitrogen airflow, 192 g of manganese dioxide was added in three portions to the obtained solution under ice cooling, the resultant was stirred under ice cooling for 2 hours and filtered by Celite, and the Celite was washed with 350 ml of 1,4-dioxane. Under a nitrogen airflow, a solution of 23.0 g (237 mmol) of maleimide in 200 ml of 1,4-dioxane was added dropwise to the obtained solution over 8 minutes with stirring under ice cooling, and the resultant was stirred at room temperature for 1 hour. This solution was added dropwise to 700 ml of 1,4-dioxane of 100° C. over 64 minutes, and the resultant was stirred at 100° C. for 1 hour. After the reaction was completed, the resultant was cooled to room temperature and concentrated under a reduced pressure. 150 ml of ethanol was added to the residue, and the resultant was concentrated to about 125 g under a reduced pressure. The precipitated solid was collected by filtration and dried at 50° C. under a reduced pressure to give 32.1 g of the titled compound as a white solid. (Yield 46%)

The steric configuration was confirmed by measuring a $^1$H-NMR NOE difference spectrum of Reference Example 1-(a) obtained in a similar method.

Mass spectrum (CI, m/z): 294, 296[M$^+$+1].

¹H-NMR spectrum (400 MHz, DMSO-d₆) δppm: 10.96 (0.9H, br s), 7.54 (1H, dd, J=1.7, 1.6 Hz), 7.50 (1H, ddd, J=7.6, 1.7, 1.6 Hz), 7.37 (1H, ddd, J=7.7, 1.6, 1.6 Hz), 7.33 (1H, dd, J=7.7, 7.6 Hz), 2.90 (2H, s), 1.82 (2H, q, J=7.4 Hz), 0.78 (3H, t, J=7.4 Hz).

Reference Example 1-(b)

(1R,5S,6r)-tert-butyl 6-(3-bromophenyl)-6-ethyl-3-azabicyclo[3.1.0]hexane-3-carboxylate Under an argon airflow, 181 ml (163 mmol) of a 0.9 M boran-tetrahydrofuran complex/tetrahydrofuran solution was added dropwise at 0° C. to a solution of 12.0 g (40.8 mmol) of (1R,5S,6r)-6-(3-bromophenyl)-6-ethyl-3-azabicyclo[3.1.0]hexane-2,4-dione, which was obtained in Reference Example 1-(a), in 120 ml of tetrahydrofuran, and the resultant was stirred at 65° C. for 2.5 hours. 48.3 ml (290 mmol) of 6 N hydrochloric acid was then added dropwise under ice cooling, and the resultant was stirred at 65° C. for 1.5 hours. After the reaction was completed, the resultant was cooled to room temperature, 97.0 ml (485 mmol) of a 5 N aqueous sodium hydroxide solution and 8.46 g (38.8 mmol) of di-tert-butyl dicarbonate were added thereto, and the resultant was vigorously stirred at room temperature for 2 hours and 45 minutes. After the reaction was completed, the obtained reaction solution was subjected to liquid separation, and the aqueous layer was extracted with ethyl acetate. The organic layers were combined, washed with saturated aqueous sodium chloride solution, dried over anhydrous magnesium sulfate and concentrated under a reduced pressure. The residue was subjected to silica gel column chromatography (elution solvent; hexane:ethyl acetate=100:0→85:15 (V/V)), and the fraction containing the objective product was concentrated under a reduced pressure to give 8.55 g of the titled compound as a white solid. (Yield 57%)

Mass spectrum (CI, m/z): 366, 368[M⁺+1].

¹H-NMR spectrum (400 MHz, CDCl₃) δppm: 7.40 (1H, dd, J=1.8, 1.6 Hz), 7.33 (1H, ddd, J=7.3, 1.8, 1.8 Hz), 7.18 (1H, ddd, J=7.6, 1.8, 1.6 Hz), 7.15 (1H, dd, J=7.6, 7.3 Hz), 3.64 (1H, dd, J=11.4, 5.1 Hz), 3.59 (1H, dd, J=11.6, 5.2 Hz), 3.54 (1H, d, J=11.4 Hz), 3.47 (1H, d, J=11.6 Hz), 1.91 (1H, dd, J=8.1, 5.1 Hz), 1.87 (1H, dd, J=8.1, 5.2 Hz), 1.56 (2H, qd, J=7.4, 1.0 Hz), 1.47 (9H, s), 0.82 (3H, t, J=7.4 Hz).

Reference Example 1-(c)

(1R,5S,6r)-tert-butyl 6-[3-(cyclopropanesulfonamido)phenyl]-6-ethyl-3-azabicyclo[3.1.0]hexane-3-carboxylate 3.67 g (30.3 mmol) of cyclopropanesulfonamide, 4.51 g (32.6 mmol) of potassium carbonate, 0.170 g (0.465 mmol) of bis(η3-allyl-μ-chloropalladium) and 0.600 g (1.41 mmol) of tert-butyl XPhos were added to a solution of 8.54 g (23.3 mmol) of (1R,5S,6r)-tert-butyl 6-(3-bromophenyl)-6-ethyl-3-azabicyclo[3.1.0]hexane-3-carboxylate, which was obtained in Reference Example 1-(b), in 85 ml of toluene under an argon airflow, with stirring at room temperature and the resultant was stirred at 110° C. for 1 hour. The reaction was completed, then water was added to the reaction solution, and the resultant was extracted with toluene. The organic layer was dried over anhydrous magnesium sulfate and concentrated under a reduced pressure. The residue was subjected to silica gel column chromatography (elution solvent; hexane:ethyl acetate=80:20→70:30 (V/V)), the fraction containing the objective product was concentrated under a reduced pressure, and the precipitated solid was subjected to an ultrasonic treatment in a solution of hexane:ethyl acetate=1:1 (V/V) and stirred and collected by filtration to give 7.86 g of the titled compound as a white solid. (Yield 83%)

Mass spectrum (CI, m/z): 407[M⁺+1].

¹H-NMR spectrum (400 MHz, CDCl₃) δppm: 7.25 (1H, dd, J=7.8, 7.8 Hz), 7.16 (1H, dd, J=1.9, 1.9 Hz), 7.11-7.05 (2H, m), 6.37 (0.9H, s), 3.65 (1H, dd, J=11.4, 5.1 Hz), 3.60 (1H, dd, J=11.5, 5.1 Hz), 3.54 (1H, d, J=11.4 Hz), 3.48 (1H, d, J=11.5 Hz), 2.46 (1H, tt, J=8.0, 4.8 Hz), 1.91 (1H, dd, J=8.4, 5.1 Hz), 1.87 (1H, dd, J=8.4, 5.1 Hz), 1.57 (2H, qd, J=7.4, 2.0 Hz), 1.47 (9H, s), 1.19-1.13 (2H, m), 0.99-0.92 (2H, m), 0.82 (3H, t, J=7.4 Hz).

Reference Example 1-(d)

N-{3-[(1R,5S,6r)-6-ethyl-3-azabicyclo[3.1.0]hexan-6-yl]phenyl}cyclopropanesulfonamide hydrochloride Under an argon airflow, 62.8 ml (251 mmol) of a 4 N hydrogen chloride/1,4-dioxane solution was added to a solution of 7.80 g (19.2 mmol) of (1R,5S,6r)-tert-butyl 6-[3-(cyclopropanesulfonamido)phenyl]-6-ethyl-3-azabicyclo[3.1.0]hexane-3-carboxylate, which was obtained in Reference Example 1-(c), in 10 ml of 1,4-dioxane, with stirring, and the resultant was stirred at room temperature for 15 hours. After the reaction was completed, the reaction solution was concentrated under a reduced pressure. 50 ml of ethyl acetate was then added thereto, the resultant was subjected to a ultrasonic treatment and stirred at room temperature, and the precipitated solid was collected by filtration to give 6.64 g of the titled compound as a white solid quantitatively. (Calculated as a monohydrochloride)

Mass spectrum (CI, m/z): 307[M⁺+1].

¹H-NMR spectrum (400 MHz, DMSO-d₆) δppm: 9.95 (1H, br s), 9.69 (1H, s), 9.26 (1H, br s), 7.26 (1H, dd, J=7.9, 7.8 Hz), 7.15 (1H, dd, J=1.9, 1.5 Hz), 7.07 (1H, ddd, J=7.9, 1.9, 1.1 Hz), 7.00 (1H, ddd, J=7.8, 1.5, 1.1 Hz), 3.70-3.55 (2H, m), 3.24-3.13 (2H, m), 2.58 (1H, tt, J=7.6, 5.1 Hz), 2.18-2.12 (2H, m), 1.59 (2H, q, J=7.3 Hz), 0.94-0.85 (4H, m), 0.77 (3H, t, J=7.3 Hz).

Reference Example 2

Preparation of (2-hydroxy-2,3-dihydro-1H-inden-2-yl)methyl methanesulfonate

Reference Example 2-(a)

2-(hydroxymethyl)-2,3-dihydro-1H-inden-2-ol 7.13 g (40.0 mmol) of 2-hydroxy-2,3-dihydro-1H-indene-2-carboxylic acid (see Journal of Organic Chemistry, 56 (1991) 4129-4134) was added to a mixed solution of 40 ml (80 mmol) of a 2.0 M lithium aluminum hydride/tetrahydrofuran solution and 60 ml of tetrahydrofuran under ice cooling, and the resultant was stirred at room temperature for 1 hour. After the reaction was completed, 3.0 ml of water and 120 ml of a 2 N hydrochloric acid were added to the reaction solution, and the resultant was extracted with 100 ml of ethyl acetate. The organic layer was washed with 50 ml of 1 N hydrochloric acid and a saturated aqueous sodium chloride solution, dried over anhydrous magnesium sulfate and concentrated under a reduced pressure. Diisopropyl ether and a small amount of ethyl acetate were added, the resultant was stirred under room temperature for 15 hours, and the precipitated solid was collected by filtration to give 5.23 g of the titled compound as a white solid. (Yield 80%)

Mass spectrum (EI, m/z): 164[M$^+$].

$^1$H-NMR spectrum (400 MHz, CDCl$_3$) δppm: 7.24-7.14 (4H, m), 3.70 (2H, s), 3.11 (2H, d, J=16.4 Hz), 2.99 (2H, d, J=16.4 Hz), 2.70-1.50 (2H, m).

Reference Example 2-(b)

(2-hydroxy-2,3-dihydro-1H-inden-2-yl)methyl methanesulfonate

After 5.62 ml (40.3 mmol) of triethylamine was added to a solution of 4.41 g (26.9 mmol) of 2-(hydroxymethyl)-2,3-dihydro-1H-inden-2-ol, which was obtained in Reference Example 2-(a), in 50 ml of methylene chloride, 2.19 ml (28.3 mmol) of methanesulfonyl chloride was added dropwise at 0° C., and the resultant was stirred at the same temperature for 3 hours. After the reaction was completed, 100 ml of water was added to the reaction solution, and the resultant was extracted with 300 ml of ethyl acetate. The organic layer was dried over anhydrous magnesium sulfate and concentrated under a reduced pressure. The residue was subjected to silica gel column chromatography (elution solvent; hexane:ethyl acetate=90:10→33:67 (V/V)), and the fraction containing the objective product was concentrated under a reduced pressure to give the 5.45 g of the titled compound as a pale yellow solid. (Yield 84%)

Mass spectrum (EI, m/z): 242[M$^+$].

$^1$H-NMR spectrum (400 MHz, CDCl$_3$) δppm: 7.25-7.16 (4H, m), 4.34 (2H, s), 3.18 (2H, d, J=16.3 Hz), 3.10 (3H, s), 3.06 (2H, d, J=16.3 Hz), 2.36 (0.9H, s).

Reference Example 3

Preparation of N-{3-[(1R,5S,6r)-6-ethyl-3-azabicyclo[3.1.0]hexan-6-yl]-4-fluorophenyl}cyclopropane sulfonamide hydrochloride Reference Example 3-(a)

(1R,5S,6r)-6-(5-bromo-2-fluorophenyl)-6-ethyl-3-azabicyclo[3.1.0]hexane-2,4-dione 29.9 g (598 mmol) of hydrazine monohydrate was added dropwise to a solution of 34.5 g (149 mmol) of 1-(5-bromo-2-fluorophenyl)propan-1-one (see WO 2009/144554) in 350 ml of methanol at room temperature, and the resultant was stirred at 65° C. for 4 hours. After the reaction was completed, the resultant was cooled to room temperature and poured into a mixed solvent of 700 ml of methylene chloride and 350 ml of water, and the resultant was subjected to liquid separation. After the organic layer was washed twice with 350 ml of water and dried over anhydrous magnesium sulfate, 315 g of 1,4-dioxane was added thereto, and the resultant was concentrated under a reduced pressure to give about 330 g of a colorless transparent solution. Under a nitrogen airflow, 100 g of manganese dioxide was divided into two portions and added to the obtained solution under ice cooling, and the resultant was stirred at room temperature for 30 minutes. 25 g of manganese dioxide was further added, and the resultant was stirred at room temperature for 30 minutes. The reaction solution was filtered by Celite, and the Celite was washed with 250 ml of 1,4-dioxane. 14.5 g (149 mmol) of maleimide was then added with stirring to the obtained solution under a nitrogen airflow under ice cooling, and the resultant was stirred at room temperature for 15 hours. This solution was added dropwise to 500 ml of 1,4-dioxane at 100° C. over 100 minutes, and the resultant was stirred at 100° C. for 1 hours. After the reaction was completed, the reaction solution was cooled to room temperature and concentrated to about 69 g under a reduced pressure. 100 ml of ethanol was then added, and the resultant was concentrated to 88 g under a reduced pressure. The precipitated solid was collected by filtration, dried at 50° C. under a reduced pressure to give 18.2 g of the titled compound as a white solid. (Yield 39%)

The steric configuration was confirmed by measuring a $^1$H-NMR NOE difference spectrum of Reference Example 3-(a) obtained in a similar method.

$^1$H-NMR spectrum (400 MHz, DMSO-d$_6$) δppm: 11.01 (0.9H, br s), 7.61-7.55 (2H, m), 7.28-7.21 (1H, m), 2.92 (2H, s), 1.75 (2H, q, J=7.4 Hz), 0.80 (3H, t, J=7.4 Hz).

Reference Example 3-(b)

(1R,5S,6r)-tert-butyl 6-(5-bromo-2-fluorophenyl)-6-ethyl-3-azabicyclo[3.1.0]hexane-3-carboxylate Under an argon airflow, 258 ml (232 mmol) of 0.9 M boran-tetrahydrofuran complex/tetrahydrofuran solution was added dropwise at room temperature to a solution of 18.0 g (57.7 mmol) of (1R,5S,6r)-6-(5-bromo-2-fluorophenyl)-6-ethyl-3-azabicyclo[3.1.0]hexane-2,4-dione, which was obtained in Reference Example 3-(a), in 150 ml of tetrahydrofuran, and the resultant was stirred at 65° C. for 4 hours. 80 ml (480 mmol) of 6 N hydrochloric acid was then poured thereto at 49° C., and the resultant was stirred at 65° C. for 1.5 hours. After the reaction was completed, the reaction solution was cooled to room temperature, 160 ml of a 5 N aqueous sodium hydroxide solution and 12.7 g (58.2 mmol) of di-tert-butyl dicarbonate were added, and the resultant was vigorously stirred at room temperature. After the reaction was completed, the reaction solution was subjected to liquid separation, and the organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=90:10 (V/V)), and the fraction containing the objective product was concentrated under a reduced pressure to give 10.2 g of the titled compound as a colorless oil. (Yield 46%)

Mass spectrum (CI, m/z): 384, 386[M$^+$+1].

$^1$H-NMR spectrum (400 MHz, CDCl$_3$) δppm: 7.35 (1H, dd, J=6.5, 2.6 Hz), 7.31 (1H, ddd, J=8.6, 4.4, 2.6 Hz), 6.89 (1H, dd, J=9.8, 8.6 Hz), 3.65 (1H, dd, J=11.4, 5.3 Hz), 3.60 (1H, dd, J=11.4, 5.3 Hz), 3.56 (1H, d, J=11.4 Hz), 3.50 (1H, d, J=11.4 Hz), 1.90 (1H, dd, J=8.0, 5.3 Hz), 1.80 (1H, dd, J=8.0, 5.3 Hz), 1.60-1.42 (2H, m), 1.47 (9H, s), 0.80-0.86 (3H, m).

Reference Example 3-(c)

(1R,5S,6r)-tert-butyl 6-[5-(cyclopropanesulfonamido)-2-fluorophenyl]-6-ethyl-3-azabicyclo[3.1.0]hexane-3-carboxylate 1.70 g (14.0 mmol) of cyclopropanesulfonamide, 3.00 g (21.7 mmol) of potassium carbonate, 121 mg (0.331 mmol) of bis(η3-allyl-μ-chloropalladium) and 420 mg (0.989 mmol) of tert-butyl XPhos were added to a solution of 4.19 g (10.9 mmol) of (1R,5S,6r)-tert-butyl 6-(5-bromo-2-fluorophenyl)-6-ethyl-3-azabicyclo[3.1.0]hexane-3-carboxylate, which was obtained in Reference Example 3-(b), in 40 ml of toluene, and the resultant was stirred under an argon airflow at 100° C. for 30 minutes. After the reaction was completed, 40 ml of water was added to the reaction solution, and the precipitated solid was collected by filtration. This solid was dissolved in methylene chloride, and the resultant was washed with water. The organic layer was dried over anhydrous sodium sulfate and then concentrated under a reduced pressure. 20 ml of ethyl acetate was added to the obtained solid, and the resultant was stirred at 60° C. for 15 minutes. 20 ml of hexane was then added, and the precipitated solid was collected by filtration to give 3.45 g of the titled compound as a white solid. (Yield 75%)

Mass spectrum (CI, m/z): 425[M$^+$+1].

$^1$H-NMR spectrum (400 MHz, DMSO-d$_6$) δppm: 9.59 (0.8H, br s), 7.18-7.08 (3H, m), 3.62-3.50 (2H, m), 3.41 (1H, d, J=11.5 Hz), 3.40 (1H, d, J=11.5 Hz), 2.58-2.48 (1H, m), 1.91-1.83 (2H, m), 1.48-1.35 (11H, m), 0.95-0.81 (4H, m), 0.77 (3H, t, J=7.4 Hz).

Reference Example 3-(d)

N-{3-[(1R,5S,6r)-6-ethyl-3-azabicyclo[3.1.0]hexan-6-yl]-4-fluorophenyl}cyclopropane sulfonamide hydrochloride Under an argon airflow, 30 ml (120 mmol) of a 4 N hydrogen chloride/1,4-dioxane solution was added to a solution of 5.68 g (13.4 mmol) of (1R,5S,6r)-tert-butyl 6-[5-(cyclopropanesulfonamido)-2-fluorophenyl]-6-ethyl-3-azabicyclo[3.1.0]hexane-3-carboxylate, which was obtained in Reference Example 3-(c), in 20 ml of 1,4-dioxane, under stirring, and the resultant was stirred at room temperature for 15 hours. After the reaction was completed, the reaction solution was concentrated under a reduced pressure. 50 ml of ethyl acetate was then added, and concentration operations under a reduced pressure were performed twice. Furthermore, 50 ml of ethyl acetate was added, and the precipitated solid was collected by filtration and dried under a reduced pressure to give 4.74 g of the titled compound as a white solid. (Yield 98%, calculated as a monohydrochloride)

Mass spectrum (CI, m/z): 325[M$^+$+1].

$^1$H-NMR spectrum (400 MHz, DMSO-d$_6$) δppm: 9.63 (2.4H, br s), 7.20-7.09 (3H, m), 3.69-3.56 (2H, m), 3.20 (2H, d, J=12.8 Hz), 2.59-2.48 (1H, m), 2.19-2.12 (2H, m), 1.55 (211, q, J=7.3 Hz), 0.95-0.81 (4H, m), 0.78 (3H, t, J=7.3 Hz).

Reference Example 4

Preparation of 2-methoxy-2,3-dihydro-1H-indene-2-carboaldehyde

Reference Example 4-(a)

2-methoxy-2,3-dihydro-1H-indene-2-carbonitrile 40.0 mg (0.125 mmol) of zinc iodide was added with stirring to a mixture of 3.15 g (17.7 mmol) of 2,2-dimethoxy-2,3-dihydro-1H-indene (see Bioorganic and Medicinal Chemistry Letters, 19 (2009) 5927-5930) and 2.65 ml (21.2 mmol) of trimethylsilylcyanide under ice cooling, and the resultant was stirred under ice cooling for 10 minutes, and further stirred at room temperature for 1.5 hours. After the reaction was completed, water was added to the reaction solution, the resultant was extracted with ethyl acetate, and the organic layer was dried over anhydrous magnesium sulfate and concentrated under a reduced pressure. The residue was subjected to silica gel column chromatography (elution solvent; hexane:ethyl acetate=100:0→95:5 (V/V)), and the fraction containing the objective product was concentrated under a reduced pressure to give 1.14 g of the titled compound as a brown oil. (Yield 37%)

Mass spectrum (EI, m/z): 173[M$^+$].

$^1$H-NMR spectrum (400 MHz, CDCl$_3$) δppm: 7.30-6.98 (4H, m), 3.51 (3H, s), 3.50 (2H, d, J=16.3 Hz), 3.39 (2H, d, J=16.3 Hz).

Reference Example 4-(b)

2-methoxy-2,3-dihydro-1H-indene-2-carboaldehyde 3.4 ml (3.4 mmol) of a 1.0 M diisobutylaluminum hydride/toluene solution was added dropwise at −78° C. to a solution of 0.48 g (2.8 mmol) of 2-methoxy-2,3-dihydro-1H-indene-2-carbonitrile, which was obtained in Reference Example 4-(a), in 1.5 ml of toluene, and the resultant was stirred at room temperature for 30 minutes. After the reaction was completed, the reaction solution was ice-cooled, and 0.50 ml (0.50 mmol) of 1 N hydrochloric acid was added thereto. A saturated aqueous sodium hydrogen carbonate solution and water were then added thereto, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=100:0→85:15 (V/V)), and the fraction containing the objective product was concentrated under a reduced pressure to give 230 mg of the titled compound as a yellow oil. (Yield 47%)

Mass spectrum (CI, m/z): 177[M$^+$+1].

$^1$H-NMR spectrum (400 MHz, CDCl$_3$) δppm: 9.77 (1H, s), 7.23-7.14 (4H, m), 3.34 (2H, d, J=16.7 Hz), 3.33 (3H, s), 3.17 (2H, d, J=16.7 Hz).

Reference Example 5

Preparation of 3-(4,4-difluorocyclohexyl)propanal

Reference Example 5-(a)

(E)-ethyl 3-(4,4-difluorocyclohexyl)acrylate

Under an argon airflow, 1.50 g (37.5 mmol) of sodium hydride (a 60% mineral oil dispersion) was added to a solution of 8.40 g (37.5 mmol) of triethyl phosphonoacetate in 200 ml of tetrahydrofuran under ice cooling, and the resultant was stirred under ice cooling for 30 minutes. A solution of 5.00 g (33.7 mmol) of 4,4-difluorocyclohexane-1-carboaldehyde in 40 ml of tetrahydrofuran was then added dropwise under ice cooling over 20 minutes, and the resultant was stirred at room temperature for 2.5 hours. After the reaction was completed, 200 ml of a saturated aqueous ammonium chloride solution was added to the reaction solution, and the resultant was extracted with 200 ml and 100 ml of ethyl acetate. The combined organic layers were washed with a saturated aqueous sodium chloride solution, dried over anhydrous magnesium sulfate and concentrated under a reduced pressure to give 6.62 g of the titled compound as a colorless oil. (Yield 90%)

Mass spectrum (CI, m/z): 219[M$^+$+1].

$^1$H-NMR spectrum (400 MHz, CDCl$_3$) δppm: 6.90 (1H, dd, J=15.8, 6.7 Hz), 5.83 (1H, dd, J=15.8, 1.5 Hz), 4.20 (2H, q, J=7.1 Hz), 2.31-2.06 (3H, m), 1.91-1.67 (4H, m), 1.61-1.48 (2H, m), 1.29 (3H, t, J=7.1 Hz).

Reference Example 5-(b)

ethyl 3-(4,4-difluorocyclohexyl)propionate 330 mg of 5% palladium-active carbon (containing 50% water) was added to a solution of 6.60 g (30.2 mmol) of (E)-ethyl 3-(4,4-difluorocyclohexyl)acrylate, which was obtained in Reference Example 5-(a), in 65 ml of ethanol, and the resultant was stirred under a hydrogen atmosphere of 1 atm at room temperature for 2.5 hours. After the reaction was completed, the insoluble substance was filtered off, and the filtrate was concentrated under a reduced pressure to give 5.71 g of the titled compound as a colorless oil. (Yield 86%)

$^1$H-NMR spectrum (400 MHz, CDCl$_3$) δppm: 4.13 (2H, q, J=7.2 Hz), 2.33 (2H, t, J=7.5 Hz), 2.14-2.01 (2H, m), 1.82-1.56 (6H, m), 1.42-1.22 (3H, m), 1.26 (3H, t, J=7.2 Hz).

Reference Example 5-(c)

3-(4,4-difluorocyclohexyl)propan-1-ol

A solution of 8.40 g (38.1 mmol) of ethyl 3-(4,4-difluorocyclohexyl)propionate, which was obtained in Reference Example 5-(b), in 25 ml of tetrahydrofuran was added dropwise over 15 minutes to a mixed solution of 24.5 ml (58.8 mmol) of a 2.4 M lithium aluminum hydride/tetrahydrofuran solution and 140 ml of tetrahydrofuran with stirring under ice cooling, and the resultant was stirred at room temperature for 2 hours. After the reaction was completed, 140 ml of 2 N hydrochloric acid was added to the reaction solution, and the resultant was extracted with 280 ml of ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=80:20→50:50 (V/V)), and the fraction containing the objective product was concentrated under a reduced pressure to give 6.11 g of the titled compound as a yellow oil. (Yield 90%)

$^1$H-NMR spectrum (400 MHz, DMSO-d$_6$) δppm: 4.36 (1H, t, J=5.1 Hz), 3.41-3.31 (2H, m), 2.05-1.90 (2H, m), 1.86-1.65 (4H, m), 1.49-1.02 (7H, m).

Reference Example 5-(d)

3-(4,4-difluorocyclohexyl)propanal

Under an argon airflow, 540 mg (6.43 mmol) of sodium hydrogen carbonate and 2.70 g (6.37 mmol) of a Dess-Martin reagent were added to a solution of 1.08 g (6.06 mmol) of 3-(4,4-difluorocyclohexyl)propan-1-ol, which was obtained in Reference Example 5-(c), in 40 ml of methylene chloride, and the resultant was stirred at room temperature for 1 hour. 40 ml of a saturated aqueous sodium thiosulfate solution was then added, and the resultant was stirred at room temperature for 30 minutes. After the reaction was completed, the organic layer was subjected to liquid separation and subjected to silica gel column chromatography (elution solvent; hexane:ethyl acetate=80:20 (V/V)), and the fraction containing the objective product was concentrated under a reduced pressure to give 671 mg of the titled compound as a colorless oil. (Yield 63%)

$^1$H-NMR spectrum (400 MHz, CDCl$_3$) δppm: 9.78 (1H, t, J=1.7 Hz), 2.48 (2H, td, J=7.5, 1.7 Hz), 2.15-2.01 (2H, m), 1.82-1.54 (6H, m), 1.43-1.20 (3H, m).

Reference Example 6

Preparation of 3-(4,4-difluoro-1-methoxycyclohexyl)propanal

Reference Example 6-(a)

1-allyl-4,4-difluorocyclohexanol 217 ml (447 mmol) of a 2.06 M allylmagnesium chloride/tetrahydrofuran solution was added dropwise to a solution of 30.0 g (224 mmol) of 4,4-difluorocyclohexanone in 120 ml of tetrahydrofuran at from –68 to –60° C. over 70 minutes, and the resultant was stirred at from –74 to –64° C. for 1.5 hours. After the reaction was completed, 1,200 ml of a saturated aqueous ammonium chloride solution was added dropwise to the reaction solution over 24 minutes (the internal temperature raised from –71° C. to 13° C.), and the resultant was extracted twice with 1,200 ml of ethyl acetate. The organic layer was washed with 600 ml of a saturated aqueous sodium chloride solution, dried over anhydrous sodium sulfate and concentrated under a reduced pressure. The obtained residue was subjected to silica gel column chromatography (elution solvent; hexane:ethyl acetate=100:0→80:20 (V/V)), and the fraction containing the objective product was concentrated under a reduced pressure to give 18.4 g of the titled compound as a colorless oil. (Yield 46%)

$^1$H-NMR spectrum (400 MHz, CDCl$_3$) δppm: 5.86 (1H, ddt, J=17.0, 10.1, 7.6 Hz), 5.25-5.13 (2H, m), 2.25 (2H, d, J=7.6 Hz), 2.23-2.01 (2H, m), 2.00-1.86 (2H, m), 1.72-1.64 (4H, m).

Reference Example 6-(b)

1-allyl-4,4-difluoro-1-methoxycyclohexane

Under an argon airflow, under ice cooling, 4.09 g (102 mmol) of sodium hydride (a 60% mineral oil dispersion) was added to a solution of 6.00 g (34.1 mmol) of 1-allyl-4,4-difluorocyclohexanol, which was obtained in Reference Example 6-(a), in 110 ml of tetrahydrofuran, and the resultant was stirred at room temperature for 15 minutes. 6.36 ml (102 mmol) of methyl iodide was then added dropwise thereto at room temperature. The resultant was stirred at the same temperature for 1.5 hours, warmed to 55° C., and stirred again at room temperature for 40 minutes. After the reaction was completed, 100 ml of a saturated aqueous ammonium chloride solution and 20 ml of water were added to the reaction solution, and the resultant was extracted with 100 ml of ethyl acetate. The organic layer was washed with 600 ml of a saturated aqueous sodium chloride solution, dried over anhydrous magnesium sulfate and concentrated under a reduced pressure. The residue was subjected to silica gel column chromatography (elution solvent; hexane:ethyl acetate=100:0→70:30 (V/V)), and the fraction containing the objective product was concentrated under a reduced pressure to give 5.96 g of the titled compound as a slight yellow oil. (Yield 92%)

Mass spectrum (CI, m/z): 191[M$^+$+1].

$^1$H-NMR spectrum (400 MHz, CDCl$_3$) δppm: 5.79 (1H, ddt, J=16.9, 10.2, 7.3 Hz), 5.15-5.03 (2H, m), 3.20 (3H, s), 2.25 (2H, ddd, J=7.3, 1.2, 1.2 Hz), 2.10-1.80 (6H, m), 1.58-1.46 (2H, m).

Reference Example 6-(c)

3-(4,4-difluoro-1-methoxycyclohexyl)propan-1-ol

Under an argon airflow, 170 ml (85.0 mmol) of a 0.5 M 9-borabicyclo[3.3.1]nonane/tetrahydrofuran solution was added dropwise to a solution of 5.95 g (31.3 mmol) of 1-allyl-4,4-difluoro-1-methoxycyclohexane, which was obtained in Reference Example 6-(b), in 25 ml of tetrahydrofuran, under ice cooling, and the resultant was stirred at room temperature for 2 hours. 17.5 ml (87.5 mmol) of a 5 N aqueous sodium hydroxide solution and 29 ml (256 mmol) of 30% aqueous hydrogen peroxide were then added dropwise under ice cooling, and the resultant was stirred at room temperature for 1 hour. After the reaction was completed, 200 ml of water was added to the reaction solution, and the resultant was extracted with 100 ml of ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=50:50→0:100 (V/V)), and the fraction containing the objective product was concentrated under a reduced pressure to give 5.49 g of the titled compound as a colorless oil. (Yield 84%)

Mass spectrum (CI, m/z): 209[M$^+$+1].

$^1$H-NMR spectrum (400 MHz, CDCl$_3$) δppm: 3.70-3.62 (2H, m), 3.16 (3H, s), 2.07-1.45 (12H, m).

Reference Example 6-(d)

3-(4,4-difluoro-1-methoxycyclohexyl)propanal

Under an argon airflow, 1.49 g (17.7 mmol) of sodium hydrogen carbonate and 7.51 g (17.7 mmol) of a Dess-Martin reagent were added to a solution of 3.51 g (16.9 mmol) of 3-(4,4-difluoro-1-methoxycyclohexyl)propan-1-ol, which was obtained in Reference Example 6-(c), in 40 ml of methylene chloride, and the resultant was stirred at room temperature for 2 hours. 80 ml of a saturated aqueous sodium thiosulfate solution was then added, and the resultant was stirred at room temperature for 1 hour. After the reaction was completed, the reaction solution was subjected to liquid separation. The organic layer was dried over anhydrous magnesium sulfate and concentrated under a reduced pressure. The residue was subjected to silica gel column chromatography (elution solvent; hexane:ethyl acetate=90:10→70:30 (V/V)), and the fraction containing the objective product was concentrated under a reduced pressure. Ethyl acetate and a saturated aqueous solution of sodium hydrogen carbonate were added to the obtained oil, the resultant was subjected to liquid separation, and the organic layer was washed with a saturated aqueous sodium chloride solution, dried over anhydrous magnesium sulfate and concentrated under a reduced pressure to give 2.86 g of the titled compound as a colorless oil. (Yield 82%)

Mass spectrum (CI, m/z): 207[M$^+$+1].

$^1$H-NMR spectrum (400 MHz, CDCl$_3$) δppm: 9.83 (1H, t, J=1.3 Hz), 3.12 (3H, s), 2.54-2.47 (2H, m), 2.10-1.40 (10H, m).

Reference Example 7

Preparation of 1-(3-bromopropyl)-4,4-difluoropiperidine

Reference Example 7-(a)

1-(3-bromopropyl)-4,4-difluoropiperidine 3.98 ml (28.6 mmol) of triethylamine was added to a solution of 1.50 g (9.52 mmol) of 4,4-difluoropiperidine hydrochloride and 2.91 ml (28.6 mmol) of 1,3-dibromopropane in 7.5 ml of methylene chloride, and the resultant was stirred at room temperature for 5 hours. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=87:13→65:35 (V/V)), and the fraction containing the objective product was concentrated under a reduced pressure to give 1.26 g of the titled compound as a colorless oil. (Yield 55%)

Mass spectrum (CI, m/z): 242, 244[M$^+$+1].

$^1$H-NMR spectrum (400 MHz, CDCl$_3$) δppm: 3.47 (2H, t, J=6.6 Hz), 2.58-2.50 (4H, m), 2.53 (2H, t, J=6.8 Hz), 2.06-1.93 (6H, m).

Reference Example 8

Preparation of 3-(3,3-difluoropyrrolidin-1-yl)propyl methanesulfonate

Reference Example 8-(a)

3-(3,3-difluoropyrrolidin-1-yl)propan-1-ol 5.0 ml (36 mmol) of triethylamine and 1.93 g (13.9 mmol) of 3-bromopropanol were added at room temperature to a solution of 1.00 g (6.97 mmol) of 3,3-difluoropyrrolidine hydrochloride in 10 ml of tetrahydrofuran, and the resultant was reacted in a microwave reaction apparatus at 80° C. for 1 hour. After the reaction was completed, a saturated aqueous sodium chloride solution was added to the reaction solution, and the resultant was extracted with ethyl acetate. The organic layer was dried over anhydrous magnesium sulfate and concentrated under a reduced pressure. The residue was subjected to silica gel column chromatography (DIOL type (manufactured by Fuji Silycia Chemical Ltd.), elution solvent; hexane:ethyl acetate=90:10→70:30 (V/V)), and the fraction containing the objective product was concentrated under a reduced pressure to give 0.95 g of the titled compound as a white solid. (Yield 83%)

Mass spectrum (CI, m/z): 166[M$^+$+1].

$^1$H-NMR spectrum (400 MHz, CDCl$_3$) δppm: 3.92 (0.9H, br s), 3.79 (2H, t, J=5.4 Hz), 2.96 (2H, t, J=13.1 Hz), 2.80 (2H, t, J=7.1 Hz), 2.72 (2H, t, J=6.0 Hz), 2.27 (2H, tt, J=14.5, 7.1 Hz), 1.77-1.68 (2H, m).

Reference Example 8-(b)

3-(3,3-difluoropyrrolidin-1-yl)propyl methanesulfonate 1.2 ml (8.6 mmol) of triethylamine was added to a solution of 0.950 g (5.75 mmol) of 3-(3,3-difluoropyrrolidin-1-yl)propane-1-ol, which was obtained in Reference Example 8-(a), in 9.5 ml of methylene chloride, and 538 μl (6.90 mmol) of methanesulfonyl chloride was added dropwise with stirring at 0° C., and then the resultant was stirred at the same temperature for 2 hours. After the reaction was completed, a saturated aqueous ammonium chloride solution was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=50:50→30:70 (V/V)), and the fraction containing the objective product was concentrated under a reduced pressure to give 1.25 g of the titled compound as a pale yellow solid. (Yield 89%)

Mass spectrum (CI, m/z): 244[M$^+$+1].

$^1$H-NMR spectrum (400 MHz, CDCl$_3$) δppm: 4.31 (2H, t, J=6.4 Hz), 3.01 (3H, s), 2.88 (2H, t, J=13.2 Hz), 2.73 (2H, t, J=7.2 Hz), 2.59 (2H, t, J=6.8 Hz), 2.27 (2H, tt, J=14.5, 7.2 Hz), 1.92 (2H, tt, J=6.8, 6.4 Hz).

Reference Example 9

Preparation of 3-{(1R,5S,6r)-6-ethyl-3-[(2-hydroxy-2,3-dihydro-1H-inden-2-yl)methyl]-3-azabicyclo[3.1.0]hexan-6-yl}-5-fluoroaniline Reference Example 9-(a)

(1R,5S,6r)-6-(3-bromo-5-fluorophenyl)-6-ethyl-3-azabicyclo[3.1.0]hexane-2,4-dione 30 ml (620 mmol) of hydrazine monohydrate was added dropwise over 5 minutes to a solution of 35 g (150 mmol) of 1-(3-bromo-5-fluorophenyl)propan-1-one (see US 2013/0324516) in 350 ml of methanol at room temperature. After the dropwise addition was completed, the resultant was stirred at 50° C. for 2 hours, and then stirred at 60° C. for 1.5 hours. After the reaction was completed, the reaction solution was cooled to 45° C. and poured into a mixed solution of 700 ml of methylene chloride and 350 ml of water, and the resultant was subjected to liquid separation. The organic layer was washed twice with 350 ml of water and dried over anhydrous sodium sulfate, 300 ml of 1,4-dioxane was added thereto, and the resultant was concentrated under a reduced pressure at 39° C. to give about 309 g of a solution. Under an argon airflow, 140 g of manganese dioxide was divided into three portions and added to the obtained solution at 9 to 14° C., the resultant was stirred at 10° C. or less for 1.5 hours and filtered with Celite, and the Celite was washed with 250 ml of 1,4-dioxane. Under an argon airflow, a solution of 14.7 g (151 mmol) of maleimide in 100 ml of 1,4-dioxane was added dropwise to the obtained filtrate over 21 minutes with stirring at from 4 to 7° C., and the resultant was stirred at 18° C. or less for 1 hour to give a yellow solution. This solution was added dropwise to 500 ml of 1,4-dioxane of 97° C. over 1.5 hours, and after the dropwise addition was completed, the resultant was stirred at 100° C. for 1 hour. After the reaction was completed, the reactant was cooled to room temperature and concentrated under a reduced pressure. 140 ml of ethanol was added to the residue, and the resultant was concentrated under a reduced pressure until the total weight became about 85 g. The concentrate was stirred at room temperature, and the precipitated solid was collected by filtration, washed with ethanol and dried at 50° C. under a reduced pressure to give 26.2 g of the titled compound as a white solid. (Yield 55%)

The steric configuration was confirmed by measuring a $^1$H-NMR NOE difference spectrum of Reference Example 9-(a).

$^1$H-NMR spectrum (400 MHz, DMSO-d$_6$) δppm: 10.99 (1H, br s), 7.52-7.47 (1H, m), 7.43 (1H, dd, J=1.6, 1.5 Hz), 7.30 (1H, ddd, J=9.8, 2.2, 1.6 Hz), 2.96 (2H, s), 1.84 (2H, q, J=7.4 Hz), 0.78 (3H, t, J=7.4 Hz).

Reference Example 9-(b)

(1R,5S,6r)-tert-butyl 6-(3-bromo-5-fluorophenyl)-6-ethyl-3-azabicyclo[3.1.0]hexane-3-carboxylate Under an argon airflow, 340 ml (306 mmol) of a 0.9 M boran-tetrahydrofuran complex/tetrahydrofuran solution was added to a solution of 24 g (77 mmol) of (1R,5S,6r)-6-(3-bromo-5-fluorophenyl)-6-ethyl-3-azabicyclo[3.1.0]hexane-2,4-dione, which was obtained in Reference Example 9-(a), in 200 ml of tetrahydrofuran over 36 minutes at 12 to 15° C., and the resultant was stirred at room temperature for 30 minutes, then stirred at 65° C. for 4 hours. Under ice cooling, 100 ml (600 mmol) of 6 N hydrochloric acid was added dropwise thereto, and the resultant was stirred at 65° C. for 75 minutes. After the reaction was completed, the reactant was cooled to room temperature, 200 ml (1000 mmol) of a 5 N aqueous sodium hydroxide solution and 16.8 g (77.0 mmol) of di-tert-butyl dicarbonate were added, and the resultant was vigorously stirred at room temperature for 15 hours. After the reaction was completed, the obtained reaction solution was subjected to liquid separation, and the organic layer was washed twice with a saturated aqueous sodium chloride solution, dried over anhydrous magnesium sulfate and concentrated under a reduced pressure. The residue was subjected twice to silica gel column chromatography (elution solvent; hexane:ethyl acetate=90:10 (V/V)), and the fraction containing the objective product was concentrated under a reduced pressure to give 18.9 g of the titled compound as a colorless oil. (Yield 64%)

$^1$H-NMR spectrum (400 MHz, CDCl$_3$) δppm: 7.19 (1H, dd, J=1.6, 1.5 Hz), 7.08 (1H, ddd, J=8.0, 2.3, 1.6 Hz), 6.90 (1H, ddd, J=9.6, 2.3, 1.5 Hz), 3.64 (1H, dd, J=11.5, 5.3 Hz), 3.60 (1H, dd, J=11.5, 5.3 Hz), 3.53 (1H, d, J=11.5 Hz), 3.46 (1H, d, J=11.5 Hz), 1.94-1.84 (2H, m), 1.61-1.53 (2H, m), 1.47 (9H, s), 0.83 (3H, t, J=7.4 Hz).

Reference Example 9-(c)

(1R,5S,6r)-tert-butyl 6-{3-[(diphenylmethylene)amino]-5-fluorophenyl}-6-ethyl-3-azabicyclo[3.1.0]hexane-3-carboxylate 1.24 g (6.84 mmol) of benzophenoneimine, 760 mg (7.91 mmol) of sodium tert-butoxide, 532 mg (0.854 mmol) of 2,2'-bis(diphenylphosphino)-1,1'-binaphthyl (hereinafter abbreviated as BINAP) and 66 mg (0.294 mmol) of palladium acetate were added to a solution of 2.2 g (5.7 mmol) of (1R,5S,6r)-tert-butyl 6-(3-bromo-5-fluorophenyl)-6-ethyl-3-azabicyclo[3.1.0]hexane-3-carboxylate, which was obtained in Reference Example 9-(b), in 15 ml of toluene, and the resultant was stirred in a microwave reaction apparatus at 150° C. for 20 minutes. After the reaction was completed, ethyl acetate and water were added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate), and the fraction containing the objective product was concentrated under a reduced pressure to give 2.36 g of the titled compound as an oil. (Yield 85%)

Mass spectrum (CI, m/z): 485[M$^+$+1].

$^1$H-NMR spectrum (400 MHz, CDCl$_3$) δ: 7.76-7.71 (2H, m), 7.52-7.45 (1H, m), 7.44-7.38 (2H, m), 7.29-7.24 (3H, m), 7.13-7.07 (2H, m), 6.51 (1H, ddd, J=9.8, 2.2, 1.6 Hz), 6.42 (1H, ddd, J=9.8, 2.2, 1.9 Hz), 6.24 (1H, dd, J=1.9, 1.6 Hz), 3.56 (1H, dd, J=11.5, 5.2 Hz), 3.51 (1H, dd, J=11.5, 5.3 Hz), 3.42 (1H, d, J=11.5 Hz), 3.35 (1H, d, J=11.5 Hz), 1.67 (2H, m), 1.45 (9H, s), 1.35 (2H, q, J=7.3 Hz), 0.57 (3H, t, J=7.3 Hz).

Reference Example 9-(d)

3-[(1R,5S,6r)-6-ethyl-3-azabicyclo[3.1.0]hexan-6-yl]-5-fluoroaniline hydrochloride Under an argon airflow, 20 ml (80 mmol) of a 4 N hydrogen chloride/1,4-dioxane solution was added to 2.3 g (4.7 mmol) of (1R,5S,6r)-tert-butyl 6-{3-[(diphenylmethylene)amino]-5-fluorophenyl}-6-ethyl-3-azabicyclo[3.1.0] hexane-3-carboxylate, which was obtained in Reference Example 9-(c), with stirring, and the resultant was stirred at room temperature for 15 hours. After the reaction was completed, the reaction solution was concentrated under a reduced pressure. Ethanol and diisopropyl ether were then added, and the precipitated solid was collected by filtration, washed with a mixed solvent of ethanol and diisopropyl ether to give 1.5 g of the titled compound as a white solid quantitatively. (calculated as a dihydrochloride)

$^1$H-NMR spectrum (400 MHz, DMSO-d$_6$) δppm: 9.97 (1H, br s), 9.31 (1H, br s), 6.67-6.54 (3H, m), 3.66-3.51 (2H, m), 3.20-3.10 (2H, m), 2.19-2.11 (2H, m), 1.59 (2H, q, J=7.3 Hz), 0.77 (3H, t, J=7.3 Hz).

Reference Example 9-(e)

3-{(1R,5S,6r)-6-ethyl-3-[(2-hydroxy-2,3-dihydro-1H-inden-2-yl)methyl]-3-azabicyclo[3.1.0]hexan-6-yl}-5-fluoroaniline 190 μl (1.4 mmol) of triethylamine was added to a solution of 96 mg (0.37 mmol) of 3-[(1R,5S,6r)-6-ethyl-3-azabicyclo[3.1.0]hexan-6-yl]-5-fluoroaniline hydrochloride, which was obtained in a similar method to that of Reference Example 9-(d), and 82 mg (0.34 mmol) of (2-hydroxy-2,3-dihydro-1H-inden-2-yl)methyl methanesulfonate, which was obtained in a similar method to that of Reference Example 2-(b), in 3 ml of ethanol, and the resultant was refluxed for 8 hours under heating. After the reaction was completed, water was added to the reaction solution, and the resultant was extracted with ethyl acetate. The organic layer was washed with a saturated aqueous sodium chloride solution, then dried over anhydrous magnesium sulfate, and concentrated under a reduced pressure. The residue was subjected to silica gel column chromatography (elution solvent; hexane:ethyl acetate=79:21→58:42 (V/V)), and the fraction containing the objective product was concentrated under a reduced pressure to give 87.4 mg of the titled compound as a white solid. (Yield 64%)

Mass spectrum (CI, m/z): 367[M$^+$+1].

$^1$H-NMR spectrum (400 MHz, CDCl$_3$) δppm: 7.24-7.12 (4H, m), 6.39-6.33 (2H, m), 6.21 (1H, ddd, J=10.4, 2.2, 2.2 Hz), 3.70 (2H, br s), 3.19 (2H, d, J=9.5 Hz), 3.10-3.04 (2H, m), 3.03-2.94 (4H, m), 2.81 (2H, s), 1.90-1.79 (4H, m), 0.87 (3H, t, J=7.4 Hz).

Reference Example 10

Preparation of 3-{(1R,5S,6r)-6-ethyl-3-[(2-methoxy-2,3-dihydro-1H-inden-2-yl)methyl]-3-azabicyclo[3.1.0]hexan-6-yl}-5-fluoroaniline Reference Example 10-(a)

3-{(1R,5S,6r)-6-ethyl-3-[(2-methoxy-2,3-dihydro-1H-inden-2-yl)methyl]-3-azabicyclo[3.1.0]hexan-6-yl}-5-fluoroaniline Under an argon airflow, 293 mg (1.00 mmol) of 3-[(1R,5S,6r)-6-ethyl-3-azabicyclo[3.1.0]hexan-6-yl]-5-fluoroaniline hydrochloride, which was obtained in Reference Example 9-(d), and 420 μl (3.0 mmol) of triethylamine were added to a solution of 190 mg (1.10 mmol) of 2-methoxy-2,3-dihydro-1H-indene-2-carboaldehyde, which was obtained in a similar method to that of Reference Example 4-(b), in 3 ml of methylene chloride. 1.05 g (4.95 mmol) of sodium triacetoxyborohydride was then added, and the resultant was stirred at room temperature for 3 hours. After the reaction was completed, a saturated aqueous solution of sodium hydrogen carbonate was added to the reaction solution, and the resultant was extracted with methylene chloride. The organic layer was dried over anhydrous sodium sulfate and concentrated under a reduced pressure. The residue was subjected to silica gel column chromatography (elution solvent; hexane:ethyl acetate), and the fraction containing the objective product was concentrated under a reduced pressure to give 129 mg of the titled compound as a colorless oil. (Yield 34%)

Mass spectrum (CI, m/z): 381[M$^+$+1].

$^1$H-NMR spectrum (400 MHz, DMSO-d$_6$) δppm: 7.22-7.12 (4H, m), 6.39-6.33 (2H, m), 6.20 (1H, ddd, J=10.4, 2.2, 2.2 Hz), 3.75-3.64 (2H, m), 3.24 (3H, s), 3.13 (2H, d, J=9.5 Hz), 3.11 (2H, d, J=16.5 Hz), 3.00 (2H, d, J=16.5 Hz), 2.97-2.91 (2H, m), 2.73 (2H, s), 1.91 (2H, q, J=7.4 Hz), 1.76-1.66 (2H, m), 0.85 (3H, t, J=7.4 Hz).

Reference Example 11

Preparation of 2-ethoxy-2,3-dihydro-1H-indene-2-carboaldehyde

Reference Example 11-(a)

2-ethoxy-2,3-dihydro-1H-indene-2-carbonitrile 15 mg (0.047 mmol) of zinc iodide was added to a mixture of 3.15 g (15.3 mmol) of 2,2-diethoxy-2,3-dihydro-1H-indene (see Journal of Organic Chemistry, 22, 1473 (1957)) and 2.65 ml (21.2 mmol) of trimethylsilylcyanide with stirring under ice cooling, and the resultant was stirred under ice cooling for 10 minutes and further stirred at room temperature for 1.5 hours. After the reaction was completed, water was added to the reaction solution, the resultant was extracted with ethyl acetate, and the organic layer was dried over anhydrous magnesium sulfate and concentrated under a reduced pressure. The residue was subjected to silica gel column chromatography (elution solvent; hexane:ethyl acetate=70:30→50:50 (V/V)), and the fraction containing the objective product was concentrated under a reduced pressure to give 2.2 g of the titled compound as a brown oil. (Yield 77%)

Mass spectrum (EI, m/z): 187[M$^+$].

$^1$H-NMR spectrum (400 MHz, CDCl$_3$) δppm: 7.25-7.18 (4H, m), 3.74 (2H, q, J=7.0 Hz), 3.51 (2H, d, J=16.2 Hz), 3.38 (2H, d, J=16.2 Hz), 1.25 (3H, t, J=7.0 Hz).

Reference Example 11-(b)

2-ethoxy-2,3-dihydro-1H-indene-2-carboaldehyde 21.2 ml (21.2 mmol) of a 1.0 M diisobutylaluminum hydride/toluene solution was added dropwise to a solution of 2.2 g (11.75 mmol) of 2-ethoxy-2,3-dihydro-1H-indene-2-carbonitrile, which was obtained in a similar method to that of Reference Example 11-(a), in 7 ml of toluene at −78° C., and the resultant was stirred at room temperature for 30 minutes. After the reaction was completed, the reaction solution was ice-cooled, and 3.4 ml (3.4 mmol) of 1 N hydrochloric acid was added. A saturated aqueous sodium hydrogen carbonate solution and water were then added, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=100:0→85:15 (V/V)), and the fraction containing the objective product was concentrated under a reduced pressure to give 0.57 g of the titled compound as a yellow oil. (Yield 26%)

Mass spectrum (CI, m/z): 191[M$^+$+1].

$^1$H-NMR spectrum (400 MHz, CDCl$_3$) δppm: 9.76 (1H, s), 7.22-7.15 (4H, m), 3.47 (2H, q, J=7.0 Hz), 3.35 (2H, d, J=16.6 Hz), 3.16 (2H, d, J=16.6 Hz), 1.24 (3H, t, J=7.0 Hz).

Reference Example 12

Preparation of
3-(1-ethoxy-4,4-difluorocyclohexyl)propanal

Reference Example 12-(a)

1-allyl-1-ethoxy-4,4-difluorocyclohexane

Under an argon airflow, 2.53 g (58.0 mmol) of sodium hydride (a 55% mineral oil dispersion) was added to a solution of 3.41 g (19.4 mmol) of 1-allyl-4,4-difluorocyclohexanol, which was obtained in a similar method to that of Reference Example 6-(a), in 30 ml of N,N-dimethylformamide under stirring at room temperature, and the resultant was stirred at 50° C. for 30 minutes. 4.68 ml (58.1 mmol) of ethyl iodide was then added dropwise at room temperature, and the resultant was stirred at 70° C. for 15 minutes. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=100:0→95:5 (V/V)), and the fraction containing the objective product was concentrated under a reduced pressure to give 2.95 g of the titled compound as a colorless oil. (Yield 75%)

$^1$H-NMR spectrum (400 MHz, CDCl$_3$) δppm: 5.79 (1H, ddt, J=17.1, 10.1, 7.0 Hz), 5.13-5.02 (2H, m), 3.37 (2H, q, J=7.0 Hz), 2.25 (2H, ddd, J=7.0, 1.5, 0.9 Hz), 2.15-1.80 (6H, m), 1.56-1.44 (2H, m), 1.18 (3H, t, J=7.0 Hz).

Reference Example 12-(b)

3-(1-ethoxy-4,4-difluorocyclohexyl)propan-1-ol

Under an argon airflow, 14.4 ml (28.8 mmol) of a 2 M boran-dimethylsulfide complex/tetrahydrofuran solution was added dropwise to a solution of 2.94 g (14.4 mmol) of 1-allyl-1-ethoxy-4,4-difluorocyclohexane, which was obtained in a similar method to that of Reference Example 12-(a), in 15 ml of tetrahydrofuran with stirring at room temperature, and the resultant was stirred at room temperature for 1 hour. 7.0 ml (35.0 mmol) of a 5 N aqueous sodium hydroxide solution and 2.0 ml (17.6 mmol) of 30% aqueous hydrogen peroxide were then added dropwise under ice cooling, and the resultant was stirred at room temperature for 2 hours. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate), and the fraction containing the objective product was concentrated under a reduced pressure to give 936 mg of the titled compound as a colorless oil. (Yield 29%)

$^1$H-NMR spectrum (400 MHz, CDCl$_3$) δppm: 3.65 (2H, dt, J=5.7, 5.7 Hz), 3.32 (2H, q, J=7.0 Hz), 2.10-1.80 (6H, m), 1.67-1.41 (6H, m), 1.26 (1H, t, J=7.2 Hz), 1.19 (3H, t, J=7.0 Hz).

Reference Example 12-(c)

3-(1-ethoxy-4,4-difluorocyclohexyl)propanal

Under an argon airflow, 224 mg (2.67 mmol) of sodium hydrogen carbonate and 1.13 g (2.66 mmol) of a Dess-Martin reagent were added to a solution of 565 mg (2.54 mmol) of 3-(1-ethoxy-4,4-difluorocyclohexyl)propan-1-ol, which was obtained in a similar method to that of Reference Example 12-(b), in 4 ml of methylene chloride, and the resultant was stirred at room temperature for 2 hours. After the reaction was completed, 20 ml of a saturated aqueous sodium thiosulfate solution was added, and the resultant was stirred at room temperature and extracted with methylene chloride. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate), and the fraction containing the objective product was concentrated under a reduced pressure to give 324 mg of the titled compound as a colorless oil. (Yield 58%)

$^1$H-NMR spectrum (400 MHz, CDCl$_3$) δppm: 9.82 (1H, t, J=1.4 Hz), 3.27 (2H, q, J=7.0 Hz), 2.55-2.46 (2H, m), 2.09-1.76 (8H, m), 1.53-1.42 (2H, m), 1.17 (3H, t, J=7.0 Hz).

Reference Example 13

Preparation of 3-(3,3-difluoropiperidin-1-yl)propyl methanesulfonate

Reference Example 13-(a)

3-(3,3-difluoropiperidin-1-yl)propyl methanesulfonate

618 µl (4.43 mmol) of triethylamine was added to a solution of 265 mg (1.48 mmol) of 3-(3,3-difluoropiperidin- 1-yl)propane-1-ol (see WO 2013/074386) and 172 μl (2.22 mmol) of methanesulfonyl chloride in 2 ml of methylene chloride with stirring, and the resultant was stirred at room temperature for 14 hours. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=77:23→56:44 (V/V)), and the fraction containing the objective product was concentrated under a reduced pressure to give 238 mg of the titled compound as a slight yellow oil. (Yield 42%)

Mass spectrum (CI, m/z): 258[M$^+$+1].

$^1$H-NMR spectrum (400 MHz, CDCl$_3$) δppm: 4.31 (2H, t, J=6.1 Hz), 3.02 (3H, s), 2.62 (2H, dd, J=11.3, 11.3 Hz), 2.54 (2H, t, J=6.8 Hz), 2.47-2.40 (2H, m), 1.99-1.82 (4H, m), 1.80-1.71 (2H, m).

Reference Example 14

Preparation of N-{3-[(1R,5S,6r)-6-methyl-3-azabicyclo[3.1.0]hexan-6-yl]phenyl}cyclopropanesulfonamide hydrochloride Reference Example 14-(a)

(1R,5S,6r)-6-methyl-6-(3-nitrophenyl)-3-azabicyclo[3.1.0]hexane-2,4-dione 22.8 g of manganese dioxide was added to a solution of 9.4 g (53 mmol) of [1-(3-nitrophenyl)ethylidene]hydradine (see WO 2000/039089) in 100 ml of 1,4-dioxane under ice cooling, and the resultant was stirred at room temperature. 22.8 g of manganese dioxide was then added. The reaction solution was filtered by Celite, and 5.34 g (55.0 mmol) of maleimide was added to the obtained solution under stirring. This reaction solution was added dropwise to 100 ml of 1,4-dioxane with heating under reflux, and the resultant was stirred at the same temperature for 1 hours. After the reaction was completed, the resultant was cooled to room temperature and concentrated under a reduced pressure. Ethanol was added to the residue, and the resultant was subjected to an ultrasonic treatment. The product was stirred under ice cooling, and the precipitated solid was collected by filtration to give 5.02 g of the titled compound as a white solid. (Yield 39%)

The steric configuration was confirmed by measuring a $^1$H-NMR NOE difference spectrum of Reference Example 14-(a).

$^1$H-NMR spectrum (400 MHz, CDCl$_3$) δppm: 8.22 (1H, dd, J=2.1, 1.9 Hz), 8.18 (1H, ddd, J=7.9, 2.1, 1.1 Hz), 7.69 (1H, ddd, J=7.9, 1.9, 1.1 Hz), 7.57 (1H, dd, J=7.9, 7.9 Hz), 2.84 (2H, dd, J=1.4 Hz), 1.71 (3H, s).

Reference Example 14-(b)

(1R,5S,6r)-tert-butyl 6-methyl-6-(3-nitrophenyl)-3-azabicyclo[3.1.0]hexane-3-carboxylate Under an argon airflow, 90 ml (81 mmol) of a 0.9 M boran-tetrahydrofuran complex/tetrahydrofuran solution was added to a solution of 5.0 g (20 mmol) of (1R,5S,6r)-6-methyl-6-(3-nitrophenyl)-3-azabicyclo[3.1.0]hexane-2,4-dione, which was obtained in a similar method to that of Reference Example 14-(a), in 40 ml of tetrahydrofuran, and the resultant was stirred at 70° C. for 3 hours. Under ice cooling, 24 ml (144 mmol) of 6 N hydrochloric acid was then added thereto, and the resultant was stirred at 70° C. After cooling to room temperature, 46 ml (184 mmol) of a 4 N aqueous sodium hydroxide solution and 4.87 g (22.3 mmol) of di-tert-butyl dicarbonate were added, and the resultant was vigorously stirred at room temperature for 15 hours. After the reaction was completed, the obtained reaction solution was subjected to liquid separation, and the organic layer was washed twice with a saturated aqueous sodium chloride solution, dried over anhydrous magnesium sulfate and concentrated under a reduced pressure. The residue was subjected to silica gel column chromatography (elution solvent; hexane:ethyl acetate=100:0→80:20 (V/V)) twice, and the fraction containing the objective product was concentrated under a reduced pressure to give 5.06 g of the titled compound as a slight yellow white solid. (Yield 78%)

Mass spectrum (CI, m/z): 319[M$^+$+1].

$^1$H-NMR spectrum (400 MHz, CDCl$_3$) δppm: 8.09 (1H, dd, J=2.1, 1.9 Hz), 8.05 (1H, ddd, J=8.0, 2.1, 1.1 Hz), 7.57 (1H, ddd, J=7.9, 1.9, 1.1 Hz), 7.46 (1H, dd, J=8.0, 7.9 Hz), 3.72-3.62 (2H, m), 3.58 (1H, d, J=11.6 Hz), 3.51 (1H, d, J=11.6 Hz), 1.98-1.89 (2H, m), 1.47 (9H, s), 1.31 (3H, s).

Reference Example 14-(c)

(1R,5S,6r)-tert-butyl 6-(3-aminophenyl)-6-methyl-3-azabicyclo[3.1.0]hexane-3-carboxylate 2.33 g (39.9 mmol) of reduced iron and 2.14 g (40.0 mmol) of ammonium chloride were added to a mixed solution of 2.55 g (8.01 mmol) of (1R,5S,6r)-tert-butyl 6-(3-nitrophenyl)-6-methyl-3-azabicyclo[3.1.0]hexane-3-carboxylate, which was obtained in a similar method to that of Reference Example 14-(b), in 70 ml of ethanol and 70 ml of water, and reflux under heating was performed for 1 hour. After the reaction was completed, the reaction solution was filtered by Celite, water was added to the filtrate, and the resultant was extracted with ethyl acetate. The organic layer was washed with a saturated aqueous sodium chloride solution, dried over anhydrous magnesium sulfate and concentrated under a reduced pressure to give 2.10 g of the titled compound as an oil. (Yield 91%)

Mass spectrum (CI, m/z): 289[M$^+$+1].

$^1$H-NMR spectrum (400 MHz, CDCl$_3$) δppm: 7.06 (1H, dd, J=7.8, 7.8 Hz), 6.63 (1H, ddd, J=7.8, 1.8, 0.9 Hz), 6.58 (1H, dd, J=2.2, 1.8 Hz), 6.51 (1H, ddd, J=7.8, 2.2, 0.9 Hz), 3.67-3.56 (4H, m), 3.52 (1H, d, J=11.4 Hz), 3.45 (1H, d, J=11.4 Hz), 1.87-1.81 (2H, m), 1.46 (9H, s), 1.22 (3H, s).

Reference Example 14-(d)

(1R,5S,6r)-tert-butyl 6-[3-(cyclopropanesulfonamido)phenyl]-6-methyl-3-azabicyclo[3.1.0]hexane-3-carboxy late 2.01 g (14.3 mmol) of cyclopropanesulfonyl chloride was added to a solution of 2.06 g (7.14 mmol) of (1R,5S,6r)-tert-butyl 6-(3-aminophenyl)-6-methyl-3-azabicyclo[3.1.0]hexane-3-carboxylate, which was obtained in a similar method to that of Reference Example 14-(c), in 15 ml of pyridine, and the resultant was heated in a microwave reaction apparatus at 80° C. for 0.5 hour. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=80:20→70:30 (V/V)), and the fraction containing the objective product was concentrated under a reduced pressure to give 2.48 g of the titled compound as a colorless oil. (Yield 88%)

Mass spectrum (CI, m/z): 393[M$^+$+1].

$^1$H-NMR spectrum (400 MHz, CDCl$_3$) δppm: 7.25 (1H, dd, J=7.8, 7.8 Hz), 7.13 (1H, dd, J=1.9, 1.9 Hz), 7.09-7.03 (2H, m), 6.27 (1H, br s), 3.69-3.58 (2H, m), 3.55 (1H, d, J=11.5 Hz), 3.48 (1H, d, J=11.5 Hz), 2.47 (1H, tt, J=8.0, 4.8 Hz), 1.91-1.82 (2H, m), 1.47 (9H, s), 1.25 (3H, s), 1.21-1.15 (2H, m), 1.00-0.93 (2H, m).

Reference Example 14-(e)

N-{3-[(1R,5S,6r)-6-methyl-3-azabicyclo[3.1.0] hexan-6-yl]phenyl}cyclopropanesulfonamide hydrochloride 23.5 ml (94 mmol) of a 4 N hydrogen chloride/1,4-dioxane solution was added to 2.46 g (6.27 mmol) of (1R,5S,6r)-tert-butyl 6-[3-(cyclopropanesulfonamido)phenyl]-6-methyl-3-azabicyclo[3.1.0]hexane-3-carboxy late, which was obtained in a similar method to that of Reference Example 14-(d), and the resultant was stirred at room temperature for 15 hours. After the reaction was completed, the reaction solution was concentrated under a reduced pressure and dried under a reduced pressure. Ethanol was added, the resultant was concentrated under a reduced pressure, a mixed solvent of ethanol and diethyl ether was added, and the obtained solid was collected by filtration to give 1.83 g of the titled compound as a white solid. (Yield 89%)

Mass spectrum (CI, m/z): 293[M$^+$+1].

$^1$H-NMR spectrum (400 MHz, DMSO-d$_6$) δppm: 10.01-8.67 (3H, m), 7.25 (1H, dd, J=8.0. 7.9 Hz), 7.14 (1H, dd, J=2.0, 1.9 Hz), 7.06 (1H, ddd, J=8.0, 2.0, 1.0 Hz), 7.02-6.98 (1H, m), 3.68-3.57 (2H, m), 3.22 (2H, d, J=12.9 Hz), 2.64-2.55 (1H, m), 2.17-2.11 (2H, m), 1.29 (3H, s), 0.95-0.88 (4H, m).

Reference Example 15

Preparation of N-{3-[(1R,5S,6r)-6-vinyl-3-azabicyclo[3.1.0]hexan-6-yl] phenyl}cyclopropanesulfonamide hydrochloride Reference Example 15-(a)

(1R,5S,6r)-6-methoxycarbonyl-6-(3-nitrophenyl)-3-azabicyclo[3.1.0]hexane-2,4-dione Under an argon airflow, 43.1 g (179 mmol) of 4-acetamidebenzenesulfonylazide was added to a solution of 33.3 g (171 mmol) of methyl 2-(3-nitrophenyl)acetate (see WO 2005/014552) in 60 ml of 1,4-dioxane with stirring at room temperature. 20 ml of 1,4-dioxane was added, and 28.3 ml (188 mmol) of DBU was added dropwise over 13 minutes under ice cooling. After the dropwise addition was completed, the resultant was stirred at room temperature for 40 minutes. After the reaction was completed, 100 ml of a saturated aqueous ammonium chloride solution and 250 ml of toluene were added, and the resultant was filtered by Celite. The filtrate was separated, the aqueous phase was extracted with 200 ml of toluene, the organic layers were combined and washed with a saturated aqueous sodium chloride solution, dried over anhydrous magnesium sulfate, and concentrated under a reduced pressure until the total weight became 263 g. 53 g of this solution was added dropwise to a solution of 18.2 g (187 mmol) of maleimide in 500 ml of toluene, which had been heated to 100° C., and the resultant was stirred at the same temperature for 20 minutes. The temperature was then raised to reflux. The remaining solution was added, 18.2 g (187 mmol) of maleimide was further added, and the resultant was refluxed under heating for 5 hours. The resultant was allowed to cool, the generated insoluble substance was filtered, the filtrate was concentrated under a reduced pressure, the residue was subjected to silica gel column chromatography (elution solvent; toluene:ethyl acetate=80:20 (V/V)), and the fraction containing the objective product was concentrated under a reduced pressure and crystallized with a mixed solvent of ethyl acetate and heptane, and the crystal was washed with diethyl ether to give 7.11 g of the titled compound as a white solid. (Yield 14%)

The steric configuration was confirmed by measuring a $^1$H-NMR NOE difference spectrum of Example 19-(a).

Mass spectrum (CI, m/z): 291[M$^+$+1].

$^1$H-NMR spectrum (400 MHz, CDCl$_3$) δppm: 8.35 (1H, dd, J=2.1, 1.8 Hz), 8.25 (1H, ddd, J=8.1, 2.1, 1.0 Hz), 7.84 (1H, ddd, J=7.9, 1.8, 1.0 Hz), 7.61 (1H, dd, J=8.1, 7.9 Hz), 7.49 (1H, br s), 3.74 (3H, s), 3.05 (2H, d, J=1.3 Hz).

Reference Example 15-(b)

(1R,5S,6s)-tert-butyl 6-hydroxymethyl-6-(3-nitrophenyl)-3-azabicyclo[3.1.0]hexane-3-carboxylate Under an argon airflow, 136 ml (122 mmol) of a 0.9 M boran-tetrahydrofuran complex/tetrahydrofuran solution was added to a solution of 7.10 g (24.5 mmol) of (1R,5S,6s)-6-methoxycarbonyl-6-(3-nitrophenyl)-3-azabicyclo[3.1.0]hexane-2,4-dione, which was obtained in a similar method to that of Reference Example 15-(a) in 50 ml of tetrahydrofuran under ice cooling, and the resultant was stirred at 75° C. for 1.5 hours. 31.3 ml (188 mmol) of a 6 N hydrochloric acid was then added under ice cooling, and the resultant was stirred at 70° C. for 1.5 hours. After cooling to room temperature, 62.5 ml (313 mmol) of a 5 N aqueous sodium hydroxide solution and 5.87 g (26.9 mmol) of di-tert-butyl dicarbonate were added, and the resultant was vigorously stirred at room temperature for 18 hours. After the reaction was completed, ethyl acetate and water were added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=94:6→73:27 (V/V)), and the fraction containing the objective product was concentrated under a reduced pressure to give 6.59 g of the titled compound as a slight yellow white solid. (Yield 81%)

Mass spectrum (CI, m/z): 335[M$^+$+1].

$^1$H-NMR spectrum (400 MHz, CD$_3$OD) δppm: 8.22 (1H, dd, J=2.1, 1.8 Hz), 8.11 (1H, ddd, J=8.1, 2.1, 1.1 Hz), 7.72 (1H, ddd, J=7.9, 1.8, 1.1 Hz), 7.51 (1H, dd, J=8.1, 7.9 Hz), 4.00-3.87 (2H, m), 3.79-3.63 (4H, m), 2.13-2.06 (2H, m), 1.48 (9H, s).

Reference Example 15-(c)

(1R,5S,6s)-tert-butyl 6-formyl-6-(3-nitrophenyl)-3-azabicyclo[3.1.0]hexane-3-carboxylate Under an argon airflow, 951 mg (2.24 mmol) of a Dess-Martin reagent was added to a solution of 0.500 g (1.50 mmol) of (1R,5S,6s)-tert-butyl 6-hydroxymethyl-6-(3-nitrophenyl)-3-azabicyclo[3.1.0]hexane-3-carboxylate, which was obtained in a similar method to that of Reference Example 15-(b), in 7.5 ml of methylene chloride at room temperature with stirring, and the resultant was stirred at the same temperature for 1 hour. After the reaction was completed, water was added to the reaction solution, and the resultant was extracted with a mixed solvent of methylene chloride and methanol. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=76:24→55:45 (V/V)), and the fraction containing the objective product was concentrated under a reduced pressure to give 491 mg of the titled compound as a slight yellow solid. (Yield 99%)

Mass spectrum (CI, m/z): 333[M$^+$+1].
$^1$H-NMR spectrum (400 MHz, CDCl$_3$) δppm: 9.57 (1H, s), 8.17 (1H, ddd, J=8.0, 2.1, 1.1 Hz), 8.12 (1H, dd, J=2.1, 1.9 Hz), 7.64-7.59 (1H, m), 7.53 (1H, dd, J=8.0, 7.9 Hz), 4.20-3.93 (2H, m), 3.92-3.74 (2H, m), 2.59-2.46 (2H, m), 1.48 (9H, s).

Reference Example 15-(d)

(1R,5S,6r)-tert-butyl 6-(3-nitrophenyl)-6-vinyl-3-azabicyclo[3.1.0]hexane-3-carboxylate Under an argon airflow, 1.82 ml (2.95 mmol) of a 1.62 M n-butyllithium/n-hexane solution was added dropwise to 1.05 g (2.94 mmol) of methyltriphenylphosphonium bromide in 10 ml of tetrahydrofuran at 0° C. with stirring, and the resultant was stirred at the same temperature for 0.5 hour. A solution of 489 mg (1.47 mmol) of (1R,5S,6s)-tert-butyl 6-formyl-6-(3-nitrophenyl)-3-azabicyclo[3.1.0]hexane-3-carboxylate, which was obtained in a similar method to that of Reference Example 15-(c), in 5 ml of tetrahydrofuran was then added dropwise under stirring at 0° C., and the resultant was stirred at 50° C. for 1 hour. After the reaction was completed, a saturated aqueous ammonium chloride solution was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=88:12→67:33 (V/V)), and the fraction containing the objective product was concentrated under a reduced pressure to give 410 mg of the titled compound as a pale yellow solid. (Yield 84%)

Mass spectrum (CI, m/z): 331[M$^+$+1].
$^1$H-NMR spectrum (400 MHz, CDCl$_3$) δppm: 8.13 (1H, dd, J=2.1, 1.8 Hz), 8.09 (1H, ddd, J=8.0, 2.1, 1.1 Hz), 7.61 (1H, ddd, J=7.8, 1.8, 1.1 Hz), 7.48 (1H, dd, J=8.0, 7.8 Hz), 5.82 (1H, dd, J=17.3, 10.7 Hz), 5.31 (1H, dd, J=10.7, 1.3 Hz), 4.84 (1H, dd, J=17.3, 1.3 Hz), 3.74 (1H, d, J=11.7 Hz), 3.70-3.59 (3H, m), 2.17-2.10 (2H, m), 1.47 (9H, s).

Reference Example 15-(e)

(1R,5S,6r)-tert-butyl 6-(3-aminophenyl)-6-vinyl-3-azabicyclo[3.1.0]hexane-3-carboxylate 347 mg (6.21 mmol) of reduced iron and 332 mg (6.21 mmol) of ammonium chloride were added to 410 mg (1.24 mmol) of (1R,5S,6r)-tert-butyl 6-(3-nitrophenyl)-6-vinyl-3-azabicyclo[3.1.0]hexane-3-carboxylate, which was obtained in a similar method to that of Reference Example 15-(d), in a mixed solution of 6 ml of ethanol and 6 ml of water, and the resultant was refluxed for 0.5 hour under heating. After the reaction was completed, ethyl acetate and water were added to the reaction solution, and the resultant was extracted with ethyl acetate. The organic layer was washed with a saturated aqueous sodium chloride solution, dried over anhydrous magnesium sulfate and concentrated under a reduced pressure to give 0.36 g of the titled compound as an oil. (Yield 97%)

Mass spectrum (CI, m/z): 301[M$^+$+1].
$^1$H-NMR spectrum (400 MHz, CDCl$_3$) δppm: 7.08 (1H, dd, J=7.8, 7.7 Hz), 6.67-6.63 (1H, m), 6.61 (1H, dd, J=2.1, 1.9 Hz), 6.54 (1H, ddd, J=7.8, 2.1, 0.9 Hz), 5.77 (1H, dd, J=17.2, 10.6 Hz), 5.22 (1H, dd, J=10.6, 1.9 Hz), 4.91 (1H, dd, J=17.2, 1.9 Hz), 3.70-3.53 (6H, m), 2.12-2.01 (2H, m), 1.46 (9H, s).

Reference Example 15-(f)

(1R,5S,6r)-tert-butyl 6-[3-(cyclopropanesulfonamido)phenyl]-6-vinyl-3-azabicyclo[3.1.0]hexane-3-carboxylate 340 mg (2.40 mmol) of cyclopropanesulfonyl chloride was added to a solution of 360 mg (1.20 mmol) of (1R,5S,6r)-tert-butyl 6-(3-aminophenyl)-6-vinyl-3-azabicyclo[3.1.0]hexane-3-carboxylate, which was obtained in a similar method to that of Reference Example 15-(e), in 5 ml of pyridine, and the resultant was heated in a microwave reaction apparatus at 80° C. for 0.5 hour. After the reaction was completed, water was added to the reaction solution, and the resultant was extracted with ethyl acetate. The organic layer was washed with a saturated aqueous sodium chloride solution, dried over anhydrous magnesium sulfate and concentrated under a reduced pressure. The residue was subjected to silica gel column chromatography (elution solvent; hexane:ethyl acetate=77:23→56:44 (V/V)), and the fraction containing the objective product was concentrated under a reduced pressure to give 445 mg of the titled compound as a slight yellow foam substance. (Yield 92%)

Mass spectrum (CI, m/z): 405[M$^+$+1].
$^1$H-NMR spectrum (400 MHz, CDCl$_3$) δppm: 7.27 (1H, dd, J=7.8, 7.8 Hz), 7.17 (1H, dd, J=1.9, 1.9 Hz), 7.12-7.07 (2H, m), 6.30 (1H, br s), 5.79 (1H, dd, J=17.3, 10.6 Hz), 5.25 (1H, dd, J=10.6, 1.7 Hz), 4.84 (1H, dd, J=17.3, 1.7 Hz), 3.70 (1H, d, J=11.5 Hz), 3.67-3.55 (3H, m), 2.46 (1H, tt, J=8.0, 4.8 Hz), 2.12-2.05 (2H, m), 1.47 (9H, s), 1.20-1.13 (2H, m), 0.99-0.92 (2H, m).

Reference Example 15-(g)

N-{3-[(1R,5S,6r)-6-vinyl-3-azabicyclo[3.1.0]hexan-6-yl]phenyl}cyclopropanesulfonamide hydrochloride 4.12 ml (16.5 mmol) of a 4 N hydrogen chloride/1,4-dioxane solution was added to 444 mg (1.10 mmol) of (1R,5S,6r)-tert-butyl 6-[3-(cyclopropanesulfonamido)phenyl]-6-vinyl-3-azabicyclo[3.1.0]hexane-3-carboxylate, which was obtained in a similar method to that of Reference Example 15-(f), and the resultant was stirred at room temperature for 18 hours. After the reaction was completed, the reaction solution was concentrated under a reduced pressure and dried under a reduced pressure. Diethyl ether was added, and the obtained solid was collected by filtration to give 355 mg of the titled compound as a white solid. (Yield 95%)

Mass spectrum (CI, m/z): 305[M$^+$+1].

$^1$H-NMR spectrum (400 MHz, DMSO-d$_6$) δppm: 10.53-8.26 (3H, m), 7.27 (1H, dd, J=7.8, 7.8 Hz), 7.16 (1H, dd, J=1.8, 1.8 Hz), 7.12-7.07 (1H, m), 7.02-6.95 (1H, m), 6.01 (1H, dd, J=17.1, 10.5 Hz), 5.41 (1H, dd, J=10.5, 1.6 Hz), 5.02 (1H, dd, J=17.1, 1.6 Hz), 3.64-3.55 (2H, m), 3.36 (2H, d, J=12.7 Hz), 2.58 (1H, tt, J=7.5, 5.2 Hz), 2.40-2.32 (2H, m), 0.95-0.86 (4H, m).

Reference Example 16

Preparation of (5,6-difluoro-2-hydroxy-2,3-dihydro-1H-inden-2-yl)methyl methanesulfonate Reference Example 16-(a)

ethyl 5,6-difluoro-1-oxo-2,3-dihydro-1H-indene-2-carboxylate 10 ml of tetrahydrofuran was added to 18 ml (23 mmol) of a 1.3 M hexamethyldisilazane lithium/tetrahydrofuran solution, a solution of 2.65 g (15.8 mmol) of 5,6-difluoro-2,3-dihydro-1H-inden-1-one (see WO 2008/142454) in 15 ml of tetrahydrofuran was added dropwise within 15 minutes under cooling at from −63° C. to −70° C., and the resultant was stirred at the same temperature for 55 minutes. A solution of 1.7 ml (18 mmol) of ethyl chloroformate/3 ml of tetrahydrofuran was then added dropwise over 15 minutes at the same temperature, and the resultant was stirred at 0° C. or less for 5 hours. Water and 1 N hydrochloric acid were added, the resultant was extracted twice with ethyl acetate, and the organic layer was washed with a saturated aqueous sodium chloride solution, dried over anhydrous sodium sulfate and concentrated under a reduced pressure. The residue was subjected to silica gel column chromatography (elution solvent; hexane:ethyl acetate=91:9→89:11 (V/V)), and the fraction containing the objective product was concentrated under a reduced pressure to give 1.56 g of the titled compound as a keto-enol equilibrium mixture as a yellow solid. (Yield 41%)

$^1$H-NMR spectrum (400 MHz, CDCl$_3$) δppm: (keto body) 7.55 (114, dd, J=8.0, 8.0 Hz), 7.33-7.27 (1H, m), 4.29-4.20 (2H, m), 3.75 (1H, dd, J=8.2, 3.8 Hz), 3.59-3.46 (1H, m), 3.39-3.29 (1H, m), 1.31 (3H, t, J=7.2 Hz)(enol body) 10.36 (0.22H, br s) 7.41 (0.25H, dd, J=9.5, 7.4 Hz), 7.33-7.23 (0.2514, m), 4.33 (0.50H, q, J=7.1 Hz), 3.52 (0.50H, s), 1.36 (0.75H, t, J=7.1 Hz).

Reference Example 16-(b)

ethyl 5,6-difluoro-2-hydroxy-1-oxo-2,3-dihydro-1H-indene-2-carboxylate

A solution of 1.01 g (4.21 mmol) of ethyl 5,6-difluoro-1-oxo-2,3-dihydro-1H-indene-2-carboxylate, which was obtained in Reference Example 16-(a), in 15 ml of methylene chloride, was added to a solution of 1.64 g (6.65 mmol) of metachloroperbenzoate in 20 ml of methylene chloride at 0° C., and the resultant was stirred at room temperature for 17 hours. After the reaction was completed, an aqueous sodium thiosulfate solution and an aqueous sodium hydrogen carbonate solution were added, and the resultant was extracted twice with methylene chloride. The organic layer was washed with a saturated aqueous sodium chloride solution, dried over anhydrous sodium sulfate and concentrated under a reduced pressure. The residue was subjected to silica gel column chromatography (elution solvent; hexane:ethyl acetate=89:11→80:20 (V/V)), and the fraction containing the objective product was concentrated under a reduced pressure to give 889 mg of the titled compound as a yellow solid. (Yield 82%)

$^1$H-NMR spectrum (400 MHz, CDCl$_3$) δppm: 7.58 (1H, dd, J=8.0, 8.0 Hz), 7.33-7.27 (1H, m), 4.27-4.18 (2H, m), 3.67 (1H, d, J=17.3 Hz), 3.21 (1H, d, J=17.3 Hz), 1.20 (3H, t, J=7.2 Hz).

Reference Example 16-(c)

ethyl 5,6-difluoro-1,2-dihydroxy-2,3-dihydro-1H-indene-2-carboxylate 893 mg of 5% palladium-active carbon (containing 50% water) was added to a solution of 732 mg (2.86 mmol) of ethyl 5,6-difluoro-2-hydroxy-1-oxo-2,3-dihydro-1H-indene-2-carboxylate, which was obtained in Reference Example 16-(b), in 10 ml of ethyl acetate, and the resultant was stirred under a hydrogen atmosphere at room temperature for 1 hour and then stirred at 55° C. for 6 hours. After cooling to room temperature, the reaction solution was filtered by Celite and washed with ethyl acetate. The obtained filtrate was concentrated under a reduced pressure. The residue was subjected to silica gel column chromatography (elution solvent; hexane:ethyl acetate=67:33 (V/V)), and the fraction containing the objective product was concentrated under a reduced pressure to give 713 mg of the titled compound as a diastereomer mixture as a white solid. (Yield 97%)

$^1$H-NMR spectrum (400 MHz, CDCl$_3$) δ: (isomer A) 7.16 (1H, dd, J=9.4, 7.8 Hz), 7.04-6.95 (1H, m), 5.17 (1H, d, J=8.1 Hz), 4.24 (2H, q, J=7.1 Hz), 3.64 (1H, s), 3.46 (1H, d, J=16.6 Hz), 3.07 (1H, d, J=16.6 Hz), 2.44 (1H, d, J=8.1 Hz), 1.21 (3H, t, J=7.1 Hz), (isomer B) 7.24-7.18 (0.05H, m), 7.04-6.95 (0.05H, m), 5.28 (0.05H, d, J=10.9 Hz), 4.35 (0.10H, q, J=7.2 Hz), 3.81-3.79 (0.05H, m), 3.42 (0.05H, d, J=14.6 Hz), 3.05 (0.05H, d, J=14.6 Hz), 2.89 (0.05H, d, J=10.9 Hz), 1.34 (0.15H, t, J=7.2 Hz).

Reference Example 16-(d)

ethyl 1-bromo-5,6-difluoro-2-hydroxy-2,3-dihydro-1H-indene-2-carboxylate

900 μl (3.62 mmol) of a 25 wt % hydrogen bromide/acetic acid solution was added to 150 mg (0.581 mmol) of ethyl 5,6-difluoro-2,3-dihydroxy-2,3-dihydro-1H-indene-2-carboxylate, which was obtained in Reference Example 16-(c), and the resultant was stirred with heating at 45° C. for 1.5 hours. The resultant was cooled to room temperature, 4 ml of water and diethyl ether were sequentially added, the pH in the system was adjusted to 5 with sodium hydrogen carbonate, and the system was extracted with diethyl ether. The organic layer was washed with a saturated aqueous sodium chloride solution and an aqueous sodium hydrogen carbonate solution, dried over anhydrous sodium sulfate and concentrated under a reduced pressure. The residue was subjected to silica gel column chromatography (elution solvent; hexane:ethyl acetate=91:9→80:20 (V/V)), and the fraction containing the objective product was concentrated under a reduced pressure to give 120 mg of the titled compound as a colorless oil. (Yield 64%)

$^1$H-NMR spectrum (400 MHz, CDCl$_3$) δppm: 7.23-7.14 (1H, m), 7.06-6.99 (1H, m), 5.64 (1H, s), 4.32 (2H, q, J=7.1

Hz), 3.51 (1H, d, J=16.1 Hz), 3.48-3.46 (1H, m), 3.18 (1H, d, J=16.1 Hz), 1.33 (3H, t, J=7.1 Hz).

Reference Example 16-(e)

ethyl 5,6-difluoro-2-hydroxy-2,3-dihydro-1H-indene-2-carboxylate 162 mg of 5% palladium-active carbon (containing 50% water) was added to a solution of 119 mg (0.371 mmol) of ethyl 1-bromo-5,6-difluoro-2-hydroxy-2,3-dihydro-1H-indene-2-carboxylate, which was obtained in a similar method to that of Reference Example 16-(d), in 3 ml of ethyl acetate, and the resultant was stirred under a hydrogen atmosphere at 50° C. for 1.5 hours. 110 mg of 5% palladium-active carbon (containing 50% water) was then added, and the resultant was stirred under a hydrogen atmosphere at 50° C. for 7 hours. After the reaction was completed, the reaction solution was cooled to room temperature, and the reaction solution was filtered by Celite and washed with ethyl acetate. The obtained filtrate was concentrated under a reduced pressure, and the residue was subjected to silica gel column chromatography (elution solvent; hexane:ethyl acetate=92:8→50:50 (V/V)), and the fraction containing the objective product was concentrated under a reduced pressure to give 57 mg of the titled compound as a colorless oil. (Yield 64%)

$^1$H-NMR spectrum (400 MHz, CDCl$_3$) δppm: 7.00 (2H, dd, J=8.7, 8.7 Hz), 4.29 (2H, q, J=7.1 Hz), 3.48 (2H, d, J=16.4 Hz), 3.40 (1H, s), 3.07 (2H, d, J=16.4 Hz), 1.30 (3H, t, J=7.1 Hz).

Reference Example 16-(f)

5,6-difluoro-2-(hydroxymethyl)-2,3-dihydro-1H-inden-2-ol

300 μl (0.300 mmol) of a 1 M lithium aluminum hydride/tetrahydrofuran solution was added to 2 ml of tetrahydrofuran, 52 mg (0.22 mmol) of ethyl 5,6-difluoro-2-hydroxy-2,3-dihydro-1H-indene-2-carboxylate, which was obtained in a similar method to that of Reference Example 16-(e), in 1.5 ml of tetrahydrofuran, was then added dropwise at 0° C. over 5 minutes, and the resultant was stirred at room temperature for 85 minutes. The resultant was cooled to 0° C., 400 μl (0.400 mmol) of a 1 M lithium aluminum hydride/tetrahydrofuran solution was added dropwise, and the resultant was stirred at room temperature for 1 hour. After the reaction was completed, an aqueous anhydrous sodium sulfate solution was added to the reaction solution, and the resultant was stirred for 20 minutes. Tetrahydrofuran and ethyl acetate were added, and the resultant was dried over anhydrous sodium sulfate and concentrated under a reduced pressure. The residue was subjected to silica gel column chromatography (elution solvent; hexane:ethyl acetate=67:33→50:50 (V/V)), and the fraction containing the objective product was concentrated under a reduced pressure to give 27 mg of the titled compound as a colorless oil. (Yield 63%)

$^1$H-NMR spectrum (400 MHz, CDCl$_3$) δppm: 6.99 (2H, dd, J=8.8, 8.8 Hz), 3.69 (2H, s), 3.05 (2H, d, J=16.4 Hz), 2.93 (2H, d, J=16.4 Hz), 2.70-1.50 (2H, m).

Reference Example 16-(g)

(5,6-difluoro-2-hydroxy-2,3-dihydro-1H-inden-2-yl) methyl methanesulfonate

24 μl (0.17 mmol) of triethylamine was added to a solution of 25 mg (0.13 mmol) of 5,6-difluoro-2-(hydroxymethyl)-2,3-dihydro-1H-inden-2-ol, which was obtained in a similar method to that of Reference Example 16-(f), in 2 ml of methylene chloride, and the resultant was stirred at 0° C. for 15 minutes. 13 μl (0.17 mmol) of methanesulfonyl chloride was further added, and the resultant was stirred at room temperature for 3.5 hours. After the reaction was completed, water was added, and the resultant was extracted with methylene chloride. The organic layer was washed with a saturated aqueous sodium chloride solution, dried over anhydrous sodium sulfate and concentrated under a reduced pressure. The residue was subjected to silica gel column chromatography (elution solvent; hexane:ethyl acetate=80:20→67:33 (V/V)), and the fraction containing the objective product was concentrated under a reduced pressure to give 27 mg of the titled compound as a colorless oil. (Yield 75%)

$^1$H-NMR spectrum (400 MHz, CDCl$_3$) δppm: 7.01 (2H, dd, J=8.8, 8.8 Hz), 4.32 (2H, s), 3.12 (2H, d, J=16.6 Hz), 3.11 (3H, s), 3.00 (2H, d, J=16.6 Hz), 2.43 (1H, s).

Pharmacological Test Example 1

(1) Preparation of Human μ-Opioid Receptor Expression Cell Membrane

Cells in which a human μ-opioid receptor had been highly expressed was purchased from ChanTest (Cleveland). The cells were cultured in a carbon dioxide gas culturing apparatus by using a Ham's F12 culture medium (Invitrogen) containing 10% of fetal bovine blood serum, 1% of non-essential amino acids, 0.4 mg/ml of G418, 100 U/ml of penicillin and 100 μg/ml of streptomycin. The cultured cells were suspended by using a 0.25% trypsin 1 mM EDTA solution, the suspension was collected by using phosphate-buffered saline and centrifuged at 4° C. and 1,000 rpm for 10 minute to remove the supernatant, whereby a cell mass was obtained. The weight of the obtained cell mass was measured, a homogenized buffer (a 10 mM KCl, 1 mM MgCl$_2$-containing 50 mM tris buffer to which a protease inhibitor (Complete EDTA free, Roche) had been added, pH 7.4) in a 5.5-fold amount was added, and the resultant was homogenized repeatedly three times in a Polytron homogenizer (SMT Multi Disperser PB95) under ice cooling at 13,000 rpm for 30 seconds, the product was then centrifuged at 4° C. and 20,000 rpm for 20 minutes, and the supernatant was removed to give a sediment. Similar homogenization and centrifugation operations were repeated on the sediment, a homogenized buffer was added again to the obtained sediment, and the resultant was similarly homogenized to give a membrane fraction solution. The obtained membrane fraction solution was dispensed, rapidly frozen and stored under freezing at −70° C. or less until use. Furthermore, the protein concentration of the obtained membrane fraction solution was measured by using a BCA protein Assay Kit (Cat. 23227, Pierce) according to the protocol attached to the kit.

(2) Antagonist Activity Test Using [$^{35}$S]-GTPγS Bond as Index Using Human μ-Opioid Receptor-Expressing Cell Membrane The cell membrane fraction solution in which the human μ-opioid receptor had expressed, which had been stored under freezing, was melted, a GTP assay buffer (100 mM NaCl, 5 mM MgCl$_2$, 1 mM EDTA-containing 50 mM Hepes (pH 7.4)) was added thereto, and the resultant was homogenized repeatedly twice by using a Polytron homogenizer (SMT Multi Disperser PB95) under ice cooling at 12,000 rpm for 20 seconds to give a homogeneous solution, and the homogeneous solution was diluted to 0.036 mg/ml with a GTP assay buffer containing 18.2 µM of GDP (final concentration: 4 µg/ml). The dilution was incubated for 15 minutes or more under ice cooling until the reaction was initiated. Example Compounds and Comparative Compound 1, which are test substances, were each dissolved in DMSO, diluted with DMSO up to a concentration of 100-fold of the test concentration, and the dilution was subjected to two-fold dilution with a GTP assay buffer to set the DMSO concentration to 50% (final concentration: 1% DMSO). [$^{35}$S]-GTPγS (NEG030X, Perkinelmer) was diluted with a GTP assay buffer so as to be 0.616 nM (final concentration: 0.08 nM). The resultant was diluted with a GTP assay buffer so as to be 200 nM (final concentration: 10 nM) by using [D-Ala$^2$, N-Me-Phe$^4$, Gly$^5$-ol]-enkephalinacetate (DAMGO, Sigma) as a µ-opioid receptor agonist. WGA Coated PVT SPA Beads (RPNQ0001, Perkinelmer) were added so as to be 20 mg/ml with a GTP assay buffer, and the resultant was suspended (final concentration: 1 mg/well). 4 µL/well of a test substance solution, 10 µL/well of a DAMGO solution, 26 µL/well of a [$^{35}$S]-GTPγS solution, 504/well of a suspension liquid of WGA Coated PVT SPA Beads, and 110 µL/well of the membrane fraction solution were added to a 96 well plate (1450-401, Perkinelmer), the top part of the plate was sealed, and a reaction was performed at 30° C. for 60 minutes under stirring with a plate shaker. For each measurement plate, a well to which DMSO had been added instead of the test substance, and a well to which DMSO had been added instead of the test substance and a GTP assay buffer had been added instead of the DAMGO solution were prepared. Furthermore, after the reaction was completed, the reactant was centrifuged at room temperature and 1,000 rpm for 3 minutes, and the radioactivity was measured by a microplate scintillation luminescence counter (Perkinelmer).

Comparative Compound 1 is the compound described in WO 2003/035622, N-(3-{(1R,5S,6r)-6-ethyl-3-[(2-hydroxy-2,3-dihydro-1H-inden-2-yl)methyl]-3-azabicyclo[3.1.0]hexan-6-yl}phenyl)methanesulfonamide methanesulfonate (this is the same in the following all test examples).

(3) Calculation of IC$_{50}$ Value

The IC$_{50}$ value of the test substance was calculated by using Graphpad Prism 5. The inhibition ratio of the test substance at the respective concentrations were calculated with setting the reaction value of the well to which DMSO had been added instead of the test substance to be 0%, and the reaction value of the well to which DMSO had been added instead of the test substance and a GTP assay buffer had been added instead of the DAMGO solution to be 100%, and a value that represented 50% inhibition was deemed as IC$_{50}$ from the concentration-reaction curve, and the obtained value is described in Table 1. As a result, it was found that all of the Example Compounds that were tested at this time had a µ-opioid receptor antagonistic activity.

TABLE 1

| Example | IC$_{50}$ (nM) |
| --- | --- |
| 1-(b) | 1.5 |
| 2-(b) | 2.0 |
| 3-(b) | 3.6 |
| 4-(b) | 1.5 |

TABLE 1-continued

| Example | IC$_{50}$ (nM) |
| --- | --- |
| 5-(b) | 1.6 |
| 6-(b) | 1.3 |
| 7-(b) | 1.4 |
| 8-(b) | 2.9 |
| 9-(b) | 2.5 |
| 10-(b) | 3.2 |
| 11-(b) | 2.8 |
| 12-(b) | 12 |
| 13-(b) | 4.1 |
| 14-(b) | 1.3 |
| 15-(b) | 1.7 |
| 16-(b) | 3.1 |
| 17-(b) | 5.4 |
| 18-(b) | 16 |
| 19-(b) | 4.5 |
| 20-(a) | 4.1 |
| Comparative compound 1 | 1.3 |

Pharmacological Test Example 2

(1) Evaluation of Anti-Pruritic Effect by Using Pruritus Mice Model to which Morphine Had been Intracisternally Administered The anti-pruritic effects of the compounds of the present invention were evaluated by using pruritus mice model to which morphine had been intracisternally administered.

As experimental animals, male ICR (Cr1j: CD1 (ICR): Charles River Japan) mice were used at 5 to 6-week old. The mice were placed in an acrylic cage (colorless and transparent, W 13.5 cm×D 9.5 cm×H 40 cm) for observing scratching behavior for 30 minutes or more to thereby allow the mice to get used to the observation environment, and the test substance solutions were forcedly orally administered to the test substance-administered groups. In addition, an administration vehicle was forcedly orally administered to the normal control group and the pathological control group. A necessary amount of the test substance was weighed and formed into a micropowder in an agate mortar, an administration vehicle, a 0.5 w/v % methyl cellulose 400 solution (Wako Pure Chemical Industries Ltd.) was added little by little, and preparation was performed by suspending or dissolving so as to give an intended concentration (from 0.025 to 3 mg/ml). The test doses were preset to suitable doses in the range in which the maximum dose is 30 mg/10 ml/kg.

The morphine solution, which induces pruritus, was prepared by dissolving morphine hydrochloride hydrate "Shionogi" (Shionogi & Co., Ltd.) in saline so as to be 0.3 nmol/5 µL. The morphine solutions were intracisternally administered at 5 µL/site to the test substance-administered groups at after 30-120 minutes of the administration of the test substance solutions, whereby a scratching behavior was induced. Based on 30 minutes after the forced oral administration of the test substance as a criterion, the time for the intracisternal administration of morphine was suitably set up to 120 minutes after at the maximum, with consideration for the times of maximum plasma concentration of the respective test substances, in the case when the in vivo pharmacokinetics of the test substance had been confirmed in advance. Furthermore, saline was intracisternally administered to the normal control group, and the above-mentioned morphine solution was intracisternally administered to the pathogenic control group, so as to be 5 µL/site at the same time as that of the test substance group after the forced oral administration of the administration vehicle in either case.

The behavior of each mouse within 60 minutes from the intracisternal administration of the morphine solution or saline was recorded by a digital video camera that was installed immediately above the acrylic cage, the images were stored in a digital video recorder, and the number of frequency of the scratching behavior was measured. The number of frequency of the scratching behavior was measured with deeming a behavior in which the mouse raised its hindlimb, scratched the facial surface and the peripheral sites thereof, and got the hindlimb off from the body within 30 minutes from after the intracisternal administration of the morphine or saline as one time.

(2) Calculation of Anti-Pruritic Effect

The anti-pruritic effect of each test substance was obtained as follows. As an inhibition ratio against the number of frequency of the scratching behavior on the pathological control group, the inhibition ratio (%) of the respective individuals and the average value thereof were calculated from the following formula, and an $ED_{50}$ value was calculated based on the obtained inhibition ratio.

Inhibition ratio of each individual (%)={1−(A−Vehicle)/(Morphine−Vehicle)}×100

Morphine: the average of the scratching number of the pathological control group
Vehicle: the average of the scratching number of the normal control group
A: the scratching number of each individual in the test substance-administered group (3) Calculation of $ED_{50}$ Value An $ED_{50}$ value was obtained as a value of 50% inhibition, which was performed by nonlinear regression analysis from a reaction curve of the dose-scratching behavior inhibition ratio using biostatic analysis software GraphPad Prism 5 (GraphPad Software), and the obtained value was described in Table 2. As a result, it was found that the compounds of all of the Examples for which tests were performed at this time had an anti-pruritic effect in the pruritus mice model to which morphine had been intracisternally administered.

TABLE 2

| Example | $ED_{50}$ (mg/kg) |
|---|---|
| 1-(a) | 3.5 |
| 2-(b) | 0.83 |
| 3-(b) | 4.2 |
| 4-(b) | 0.50 |
| 5-(b) | 1.7 |
| 6-(b) | 0.42 |
| 7-(b) | 2.4 |
| 8-(b) | 2.0 |
| 9-(b) | — |
| 10-(b) | 1.8 |
| 11-(b) | — |
| 12-(b) | 3.2 |
| 13-(b) | 2.4 |
| 14-(b) | — |
| 15-(b) | 3.1 |
| 16-(b) | 5.7 |
| 17-(b) | 1.5 |
| 18-(b) | — |
| 19-(b) | — |
| 20-(a) | — |
| Comparative compound 1 | 2.6 |

(—: not performed)

Pharmacological Test Example 3

(1) Collection of Sample for Calculation of Concentration in Plasma

The concentration of the test substances in blood plasma was confirmed by using mice of the same week-old for the same dose as that used in the evaluation of the anti-pruritic effect. The test substance was administered by forced oral administration of an administration vehicle prepared in a similar manner to that in the evaluation of the anti-pruritic effect under a non-fasting condition. The blood samples were collected from the orbital venous plexus, within from 15 minutes after the administration of the test substance to after 180 minutes at the maximum, for multiple times including the timing at which the morphine solution was intracisternally administered, under inhalation anesthesia with diethyl ether or isoflurane using a heparin-treated hematocrit tubes. The collected blood samples were immediately ice-cooled and centrifuged at 1,800 g for 15 minutes at 4° C., and the plasma fractions were transferred and stored under freezing at −30° C. or less until measurement.

(2) Measurement of Plasma Concentrations

The concentrations of the test substances in plasma were measured using LC/MS/MS. Furthermore, as the measurement samples for LC/MS/MS, the supernatants obtained by adding an internal standard substance and acetonitrile in an amount within a range from 5-fold to 10-fold of the amount of the plasma to the collected plasma samples, and removing proteins therefrom, was used.

(3) Calculation of Plasma Concentration of Test Substance at $ED_{50}$ Value

The plasma concentrations of test substances at the $ED_{50}$ values were calculated by deriving a linear regression formula from the administered doses and the plasma concentrations of test substances, by using, among the doses that were actually administered, the values at the time when morphine was administered at the immediate two doses in which the $ED_{50}$ value calculated in Pharmacological Test Example 2 was interposed, and the obtained values were described in Table 3.

TABLE 3

| Example | Plasma concentration of test substance (nM) |
|---|---|
| 1-(a) | 70.8 |
| 2-(b) | 21.4 |
| 3-(b) | 48.8 |
| 4-(b) | 31.6 |
| 5-(b) | 116 |
| 6-(b) | 7.94 |
| 7-(b) | 21.5 |
| 8-(b) | 10.9 |
| 9-(b) | — |
| 10-(b) | 129 |
| 11-(b) | — |
| 12-(b) | 193 |
| 13-(b) | 71.9 |
| 14-(b) | — |
| 15-(b) | 71.5 |
| 16-(b) | 44.5 |
| 17-(b) | 68.2 |
| 18-(b) | — |
| 19-(b) | — |
| 20-(a) | — |
| Comparative compound 1 | 157 |

(—: not performed)

Pharmacological Test Example 4

(1) hERG Inhibition Assay

Using hERG (human ether-a-go-go related gene)-transfected HEK293 cells, under a fixed potential, the hERG-derived potassium currents (hereinafter hERG currents) that had passed through the entirety of the cell membrane were measured by the whole-cell patch-clamp method. The effects on the hERG currents were confirmed by the changes in the maximum tail current value that were induced by repolarization pulse. The test conditions were as shown in Table 4.

The suppressive effect on the hERG current in each cell was calculated by a change rate after 10 minutes of application on the maximum tail current at 1 minute after the initiation of the application of the test substances. The hERG inhibition rate was calculated according to the following formula by correcting the suppression rate in each cell with the average suppression rate in a vehicle control (0.1% (v/v) DMSO) group.

hERG inhibition rate (%)=$(A-B)/(100-B) \times 100$

A: the suppression rate (%) of the test substance in each cell
B: the average suppression rate (%) of the vehicle control group the hERG inhibition rate at the respective doses, and the obtained values were described in Table 5.

TABLE 5

| Example | patch IC$_{50}$ (μM) |
|---|---|
| 1-(a) | 0.11 |
| 2-(b) | 0.16 |
| 3-(b) | 0.58 |
| 4-(b) | 0.094 |
| 5-(b) | 0.089 |
| 6-(b) | 0.66 |
| 7-(b) | 1.2 |
| 8-(b) | 0.34 |
| 9-(b) | — |
| 10-(b) | 0.062 |
| 11-(b) | — |
| 12-(b) | — |
| 13-(b) | — |
| 14-(b) | — |
| 15-(b) | 1.3 |
| 16-(b) | 0.64 |
| 17-(b) | 0.13 |
| 18-(b) | 0.4 |
| 19-(b) | — |
| 20-(a) | — |
| Comparative compound 1 | 0.30 |

(—: not performed)

TABLE 4

| | |
|---|---|
| Cell line | hERG-transfected HEK293 cells (Wisconsin Alumni Research Foundation) |
| Culture medium | Dulbecco's Modified Eagle's Medium containing 10% of fetal bovine blood serum, 100 U/ml of penicillin, 100 μg/ml of streptomycin and 400 μg/ml of G418 |
| Cells used in tests | The cells were seeded on a collagen-coated cover glass and used within 72 hours. The cells were changed in every application. |
| Application method | Perfusion method |
| Application condition | Perfusion rate: 5 mL/min, temperature: 37.0 ± 1.0° C., application time: 11 min |
| Perfusion solution | 137 mM NaCl, 4 mM KCl, 1.8 mM CaCl$_2$, 1 mM MgCl$_2$, 10 mM D(+)-Glucose, 10 mM HEPES, pH 7.4 |
| Test substance | The DMSO solutions in which the test substances had been dissolved were diluted by 1,000-fold with the perfusion solution (hereinafter referred to as the application solution). Perfusion of the application solution was initiated after the electric current after the depolarization pulse had been provided was stabilized. The concentrations of the test substances were suitably set to be from 4 to 6 doses, and the effects on the hERG currents were evaluated by using two cells per dose. |
| Glass electrode | The glass electrodes having a resistance value of from 2 to 5 MΩ when filled with a glass electrode internal solution were used. |
| Glass electrode internal solution | 130 mM KCl, 1 mM MgCl$_2$•6H$_2$O, 5 mM EGTA, 5 mM MgATP, 10 mM HEPES, pH 7.2 |
| Patch clamp method | The membrane potential was kept at −80 mV, and a depolarization pulse at +20 mV for 0.5 seconds, and a subsequent repolarization pulse at −50 mV for 0.5 seconds were provided at a frequency of once every 15 seconds. |
| Measurement | The hERG current was measured by using an amplifier for patch clamping (Axopatch-200B, Molecular Devices Corporation), and the obtained electrical signal was recorded via recording-analyzing software for patch clamping (pCLAMP 9, Molecular Devices Corporation). |

(2) Calculation of IC$_{50}$ Value

The 50% inhibitory concentration (IC$_{50}$) against the hERG current was calculated by curve fitting program to which Hill equation is applied (KaleidaGraph 3.6, Synergy Software, Pennsylvania, USA) based on the average value of Pharmacological Test Example 5

(1) Mice Serum Protein Binding Assay

The protein binding rate was determined by equilibrium dialysis method using the RED Device (8K MWCO, Rapid Equilibrium Dialysis Device, Thermo Scientific). The test substances that had been dissolved in DMSO were added to the serum that was collected from Crl: CD-1 (ICR) mice fasted overnight, so that the final concentration of DMSO became 1% (v/v). The serum to which the test substance had been added was added to the inner side of the dialysis membrane of the RED Device, and PBS (phosphate buffer saline, pH 7.4) containing 0.01% (v/v) Tween 80 was added to the outside in accordance with the method for using the RED Device and incubated at 37° C. for 5 to 6 hours with ellipsoidal shaking at 100 rpm so that the concentration of the unbound test substance in the serum and the concentration of the test substance in the PBS reached equilibrium. After the incubation was completed, the respective solutions were collected and stored under freezing at −60° C. or less as measurement samples. The proteins were removed from the measurement sample by adding acetonitrile in an amount of 5-fold or more of the amount of the internal standard substance and the serum sample, and the supernatants were measured by LC/MS/MS (liquid chromatograph—triple quadrupole mass spectrometer). The serum samples were measured after suitably diluting with distilled water as necessary. The protein binding rate was calculated by the following formula by using the ratio of the peak area of the obtained test substance and the peak area of the internal standard substance by LC/MS/MS measurement, and the obtained values were described in Table 6.

Protein binding rate in murine serum (%)=100−(A/B)×100

A: the peak area of the test substance in the PBS sample/the peak area of the internal standard substance
B: the peak area of the test substance in the serum sample/the peak area of the internal standard substance However, in the case when the concentration in the sample was calculated by using a calibration curve, A and B were as follows.

A: the concentration of the test substance in the PBS sample
B: the concentration of the test substance in the serum sample

TABLE 6

| Example | Protein binding rate (%) |
|---|---|
| 1-(a) | 98.1 |
| 2-(b) | 99.4 |
| 3-(b) | 99.4 |
| 4-(b) | 98.1 |
| 5-(b) | 99.5 |
| 6-(b) | 96.1 |
| 7-(b) | 85.1 |
| 8-(b) | 68.4 |
| 9-(b) | 82.7 |
| 10-(b) | 89.8 |
| 11-(b) | >99.9 |
| 12-(b) | 99.8 |
| 13-(b) | >99.9 |
| 14-(b) | — |
| 15-(b) | 90.0 |
| 16-(b) | 75.4 |
| 17-(b) | 96.0 |
| 18-(b) | 99.3 |
| 19-(b) | 99.1 |
| 20-(a) | 99.4 |
| Comparative compound 1 | 93.2 |

(—: not performed)

Pharmacological Test Example 6

(1) Safety Margin Against hERG Inhibitory Activity

In order to compare the risks of extension of QT interval prolongation in the electrocardiogram among the test substances, the safety margins against the hERG inhibitory effect were calculated. The safety margin was the gap between the $IC_{50}$ value against the hERG current, which was obtained in Pharmacological Test Example 4, and the unbound drug concentration in plasma at the $ED_{50}$ value in the evaluation of the anti-pruritic effect of the morphine model, which was obtained in Pharmacological Test Example 3. Therefore, the following formula was used for calculating the safety margin, and the obtained values were described in Table 7.

Safety margin against hERG inhibitory effect=$IC_{50}$×1000/{concentration in plasma×(1−protein binding rate/100)}

$IC_{50}$: the $IC_{50}$ value in a hERG inhibition assay (μM)

Plasma concentration: the plasma concentration of test substance (nM) at the $ED_{50}$ value in the test for evaluating the anti-pruritic effect in the morphine model Protein binding rate: the protein binding rate (%) in the protein binding assay in murine serum As a result, it was found that most of the compounds of the Examples which were tested at this time had a broad safety margin.

TABLE 7

| Example | Safety margin |
|---|---|
| 1-(a) | 82 |
| 2-(b) | 1250 |
| 3-(b) | 1980 |
| 4-(b) | 157 |
| 5-(b) | 153 |
| 6-(b) | 2130 |
| 7-(b) | 375 |
| 8-(b) | 99 |
| 9-(b) | — |
| 10-(b) | 5 |
| 11-(b) | — |
| 12-(b) | — |
| 13-(b) | — |
| 14-(b) | — |
| 15-(b) | 182 |
| 16-(b) | 58 |
| 17-(b) | 48 |
| 18-(b) | — |
| 19-(b) | — |
| 20-(a) | — |
| Comparative compound 1 | 28 |

(—: not performed)

INDUSTRIAL APPLICABILITY

The compound of the present invention has a μ-opioid receptor antagonistic activity, and thus is useful as an agent for preventing or treating pruritus and the like.

The invention claimed is:

1. A compound represented by the general formula (I), or a pharmacologically acceptable salt thereof:

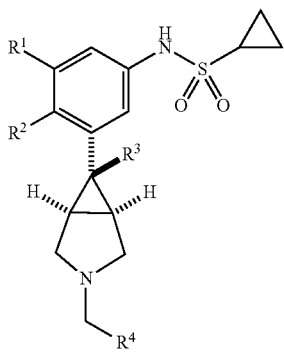

wherein
R¹ represents a hydrogen atom, and
R² represents a hydrogen atom or a halogen atom, and
R³ represents a $C_1$-$C_3$ alkyl group, and
R⁴ represents the formula (II):

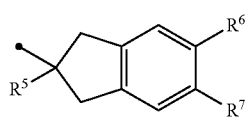

wherein R⁵ represents a hydroxy group or a $C_1$-$C_3$ alkoxy group, and R⁶ and R⁷ represent a hydrogen atom provided that R⁵ represents a hydroxy group when R² represents a halogen atom, and R⁵ represents a $C_1$-$C_3$ alkoxy group when R² represents a hydrogen atom;
or the formula (III):

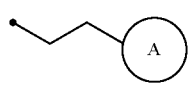

wherein Ring A represents a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group.

2. The compound or a pharmacologically acceptable salt thereof according to claim 1, wherein R³ is an ethyl group in the general formula (I).

3. The compound or a pharmacologically acceptable salt thereof according to claim 1, wherein R⁴ is the formula (II) in the general formula (I):

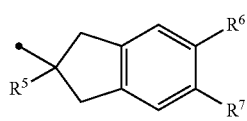

wherein R⁵ represents a hydroxy group or a $C_1$-$C_3$ alkoxy group, and R⁶ and R⁷ represent a hydrogen atom provided the R⁵ represents a hydroxy group when R² represents a halogen atom, and R⁵ represents a $C_1$-$C_3$ alkoxy group when R² represents a hydrogen atom.

4. The compound or a pharmacologically acceptable salt thereof according to claim 1, wherein R² is a hydrogen atom or a fluorine atom, and R³ is an ethyl group in the general formula (I).

5. The compound or a pharmacologically acceptable salt thereof according to claim 1, wherein R⁴ is the formula (III):

wherein Ring A is a halogen atom(s)-substituted $C_5$-$C_7$ cycloalkyl group which is optionally substituted by a $C_1$-$C_3$ alkoxy group, or a halogen atom(s)-substituted 5- to 7-membered saturated heterocyclic group in the general formula (I).

6. The compound or a pharmacologically acceptable salt thereof according to claim 5, wherein Ring A is a fluorine atom(s)-substituted cyclohexyl group which is optionally substituted by a $C_1$-$C_3$ alkoxy group, or a fluorine atom(s)-substituted 5- to 6-membered nitrogen-containing saturated heterocyclic group in the formula (III).

7. The compound or a pharmacologically acceptable salt thereof according to claim 6, wherein Ring A is any group selected from the following group:

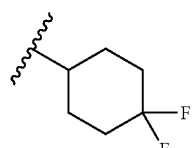
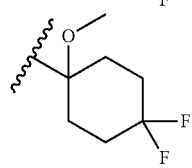
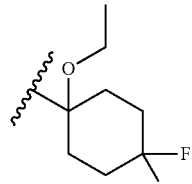
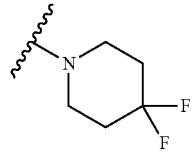
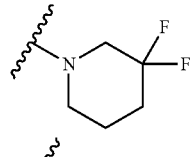
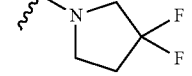

in the formula (III).

8. The compound or a pharmacologically acceptable salt thereof according to claim 3, wherein the compound is selected from the group consisting of:
   N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide, and
   N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide.

9. The compound or a pharmacologically acceptable salt thereof according to claim 5, wherein the compound is selected from the group consisting of:
   N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide,
   N-(3-{(1R,5S,6r)-3-[3-(4,4-difluorocyclohexyl)propyl]-6-ethyl-3-azabicyclo[3.1.0]hexan-6-yl}-4-fluorophenyl)cyclopropanesulfonamide,
   N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide,
   N-(3-{(1R,5S,6r)-3-[3-(4,4-difluoropiperidin-1-yl)propyl]-6-ethyl-3-azabicyclo[3.1.0]hexan-6-yl}phenyl)cyclopropanesulfonamide,
   N-(3-{(1R,5S,6r)-3-[3-(3,3-difluoropyrrolidin-1-yl)propyl]-6-ethyl-3-azabicyclo[3.1.0]hexan-6-yl}phenyl)cyclopropanesulfonamide,
   N-(3-{(1R,5S,6r)-3-[3-(4,4-difluoropiperidin-1-yl)propyl]-6-ethyl-3-azabicyclo[3.1.0]hexan-6-yl}-4-fluorophenyl)cyclopropanesulfonamide, and
   N-(3-{(1R,5S,6r)-3-[3-(3,3-difluoropiperidin-1-yl)propyl]-6-ethyl-3-azabicyclo[3.1.0]hexan-6-yl}phenyl)cyclopropanesulfonamide.

10. A medicament comprising the compound or a pharmacologically acceptable salt thereof according to claim 1 as an active ingredient.

11. A process for treating pruritus comprising administering the medicament according to claim 10 to a subject in need thereof.

12. The compound or a pharmacologically acceptable salt thereof according to claim 3, wherein the compound is
   N-(3-{(1R,5S,6r)-6-ethyl-3-[(2-hydroxy-2,3-dihydro-1H-inden-2-yl)methyl]-3-azabicyclo[3.1.0]hexan-6-yl}-4-fluorophenyl)cyclopropanesulfonamide.

13. The compound or a pharmacologically acceptable salt thereof according to claim 3, wherein the compound is
   N-(3-{(1R,5S,6r)-6-ethyl-3-[(2-methoxy-2,3-dihydro-1H-inden-2-yl)methyl]-3-azabicyclo[3.1.0]hexan-6-yl}phenyl)cyclopropanesulfonamide.

14. The compound or a pharmacologically acceptable salt thereof according to claim 5, wherein the compound is
   N-(3-{(1R,5S,6r)-3-[3-(4,4-difluorocyclohexyl)propyl]-6-ethyl-3-azabicyclo[3.1.0]hexan-6-yl}phenyl)cyclopropanesulfonamide.

15. The compound or a pharmacologically acceptable salt thereof according to claim 5, wherein the compound is
   N-(3-{(1R,5S,6r)-3-[3-(4,4-difluoro-1-methoxycyclohexyl)propyl]-6-ethyl-3-azabicyclo[3.1.0]hexan-6-yl}phenyl)cyclopropanesulfonamide.

\* \* \* \* \*